(12) United States Patent
Harris et al.

(10) Patent No.: US 8,236,011 B2
(45) Date of Patent: Aug. 7, 2012

(54) METHOD FOR DEPLOYING FASTENERS FOR USE IN A GASTRIC VOLUME REDUCTION PROCEDURE

(75) Inventors: Jason L. Harris, Mason, OH (US); Matthew D. Holcomb, Lebanon, OH (US); Mark S. Zeiner, Mason, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 364 days.

(21) Appl. No.: 12/573,907

(22) Filed: Oct. 6, 2009

(65) Prior Publication Data
US 2011/0082472 A1   Apr. 7, 2011

(51) Int. Cl.
*A61B 17/10* (2006.01)
*A61B 17/04* (2006.01)

(52) U.S. Cl. ......................................... 606/142; 606/232
(58) Field of Classification Search .................. 606/75, 606/139, 142, 219, 232; 227/175.1
See application file for complete search history.

(56) References Cited

U.S. PATENT DOCUMENTS

| | | | |
|---|---|---|---|
| 2,185,518 A | 1/1940 | Posnack | |
| 4,407,286 A | 10/1983 | Noiles et al. | |
| 4,489,875 A | 12/1984 | Crawford et al. | |
| 4,505,273 A | 3/1985 | Braun et al. | |
| 4,669,647 A | 6/1987 | Storace | |
| 5,413,584 A | 5/1995 | Schulze | |
| 5,439,468 A | 8/1995 | Schulze | |
| 5,544,802 A | 8/1996 | Crainich | |
| 5,645,567 A | 7/1997 | Crainich | |
| 5,715,987 A | 2/1998 | Kelley et al. | |
| 6,228,098 B1 | 5/2001 | Kayan et al. | |
| 6,245,080 B1 | 6/2001 | Levinson | |
| 6,330,964 B1 | 12/2001 | Kayan et al. | |
| 6,450,391 B1 | 9/2002 | Kayan et al. | |
| 6,695,854 B1 | 2/2004 | Kayan et al. | |
| 6,767,356 B2 | 7/2004 | Kanner et al. | |
| 6,915,937 B2 | 7/2005 | Lat et al. | |
| 6,957,756 B2 | 10/2005 | Lat et al. | |
| 7,056,330 B2 | 6/2006 | Gayton | |
| 7,059,509 B2 | 6/2006 | Brown | |
| 7,112,214 B2 | 9/2006 | Peterson et al. | |
| 7,320,692 B1 | 1/2008 | Bender et al. | |
| 7,344,544 B2 | 3/2008 | Bender et al. | |
| 2005/0251177 A1 | 11/2005 | Saadat et al. | |
| 2006/0206063 A1 | 9/2006 | Kagan et al. | |

(Continued)

FOREIGN PATENT DOCUMENTS

EP    1762185 B1   12/2008

(Continued)

OTHER PUBLICATIONS

International Preliminary Report dated Dec. 3, 2009; International Application No. PCT/US2009/051509.

(Continued)

*Primary Examiner* — Julian Woo

(57) ABSTRACT

A method for deploying fasteners including the steps of providing a device having a handle and at least one actuator. The handle is connected to an elongated hollow housing having distal and proximal ends. The device has a first cartridge containing at least one fastener releasably connectable to the handle and an elongated pusher movable through the hollow housing from the distal to the proximal end for deploying the fastener from the distal end. The method includes increasing the stiffness of the pusher at a distal end thereof and advancing the pusher through the elongated housing to deploy the fasteners.

7 Claims, 67 Drawing Sheets

U.S. PATENT DOCUMENTS

| | | |
|---|---|---|
| 2007/0049929 A1 | 3/2007 | Catanese, III et al. |
| 2008/0065120 A1 | 3/2008 | Zannis et al. |
| 2008/0091220 A1 | 4/2008 | Chu |
| 2008/0217376 A1 | 9/2008 | Clauson et al. |
| 2009/0024144 A1 | 1/2009 | Zeiner et al. |
| 2009/0024163 A1 | 1/2009 | Zeiner et al. |

FOREIGN PATENT DOCUMENTS

| | | |
|---|---|---|
| EP | 2016910 A2 | 1/2009 |
| EP | 2055241 A2 | 5/2009 |
| EP | 1690502 B1 | 3/2011 |
| WO | WO 2008/112942 | 9/2008 |
| WO | WO 2010/011832 A1 | 1/2010 |

OTHER PUBLICATIONS

International Preliminary Report dated Nov. 25, 2009; International Application No. PCT/US2009/051518.

International Search Report dated Dec. 20, 2010; International Application No. PCT/US2010/049738.

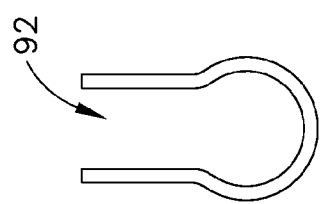
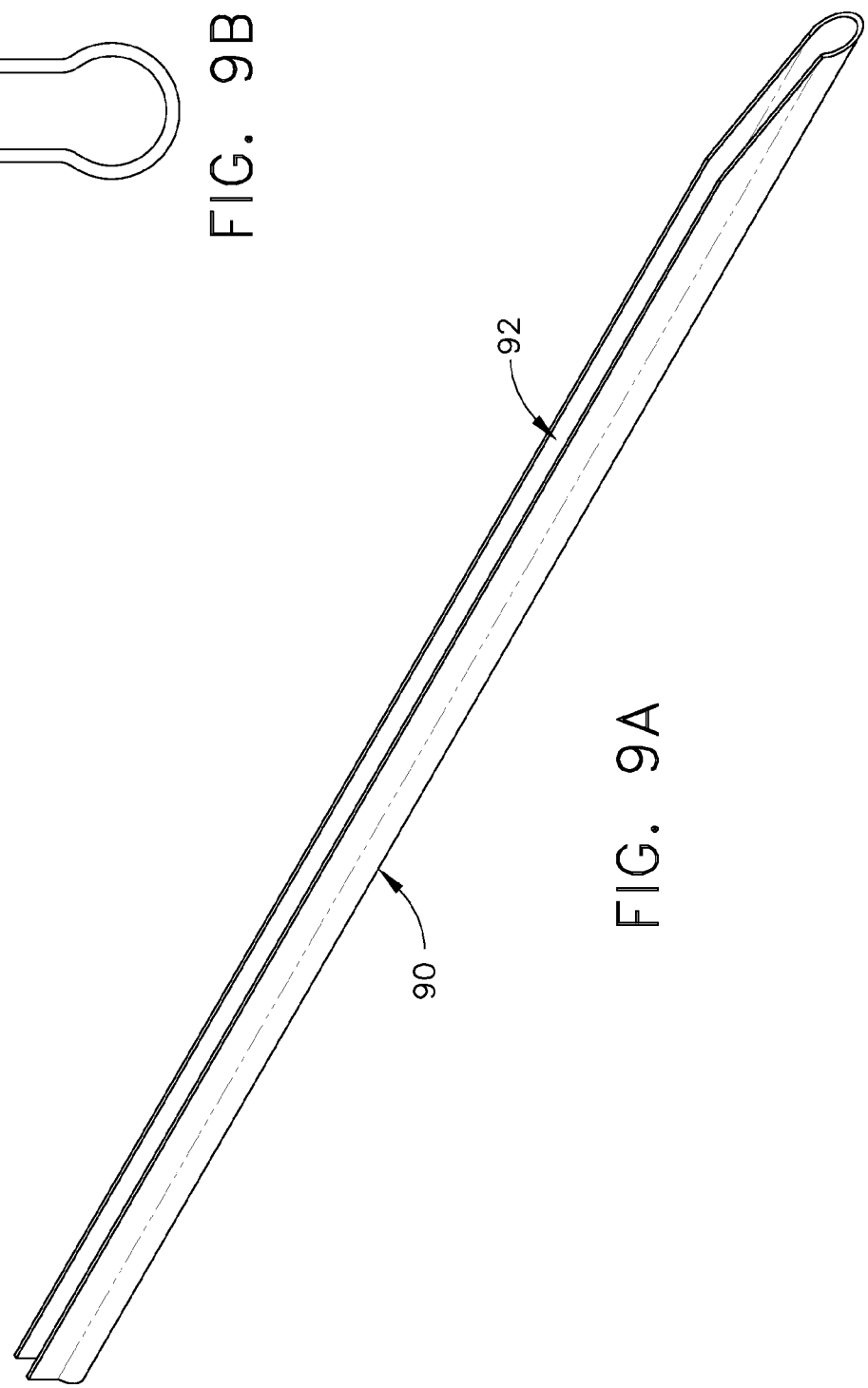

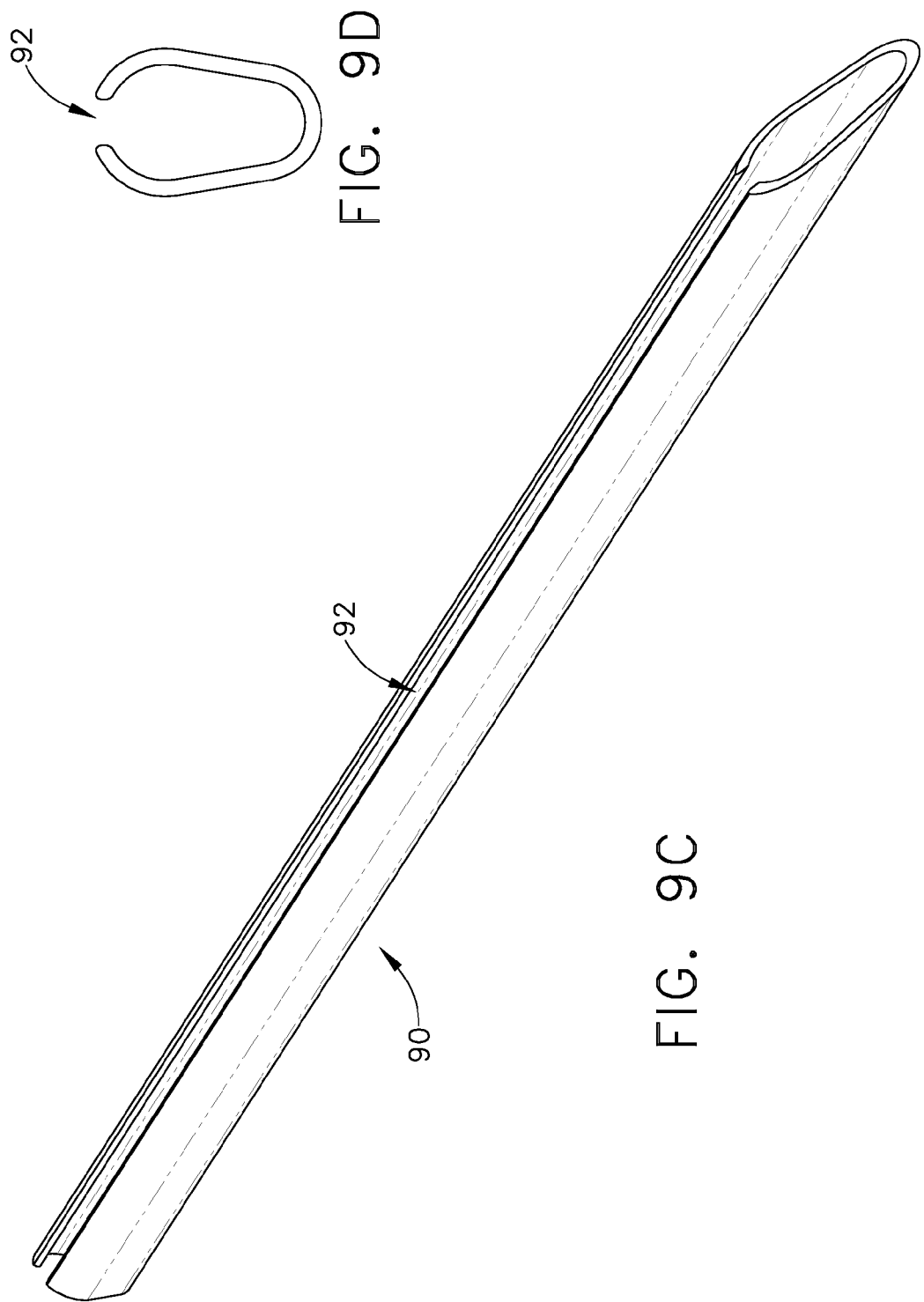

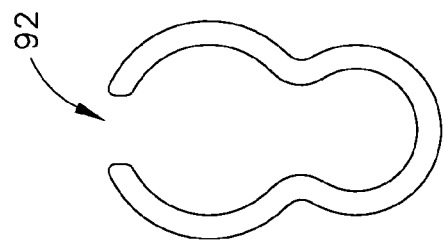
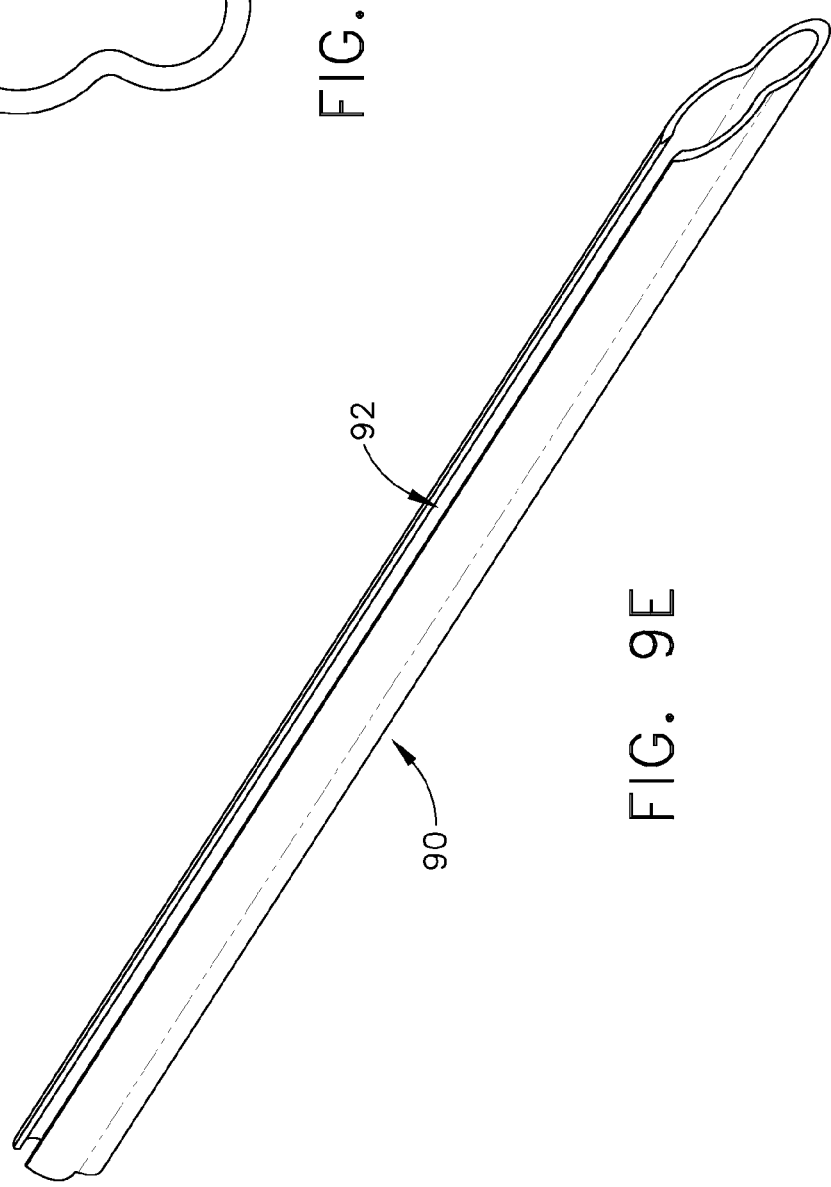
FIG. 9F
FIG. 9E

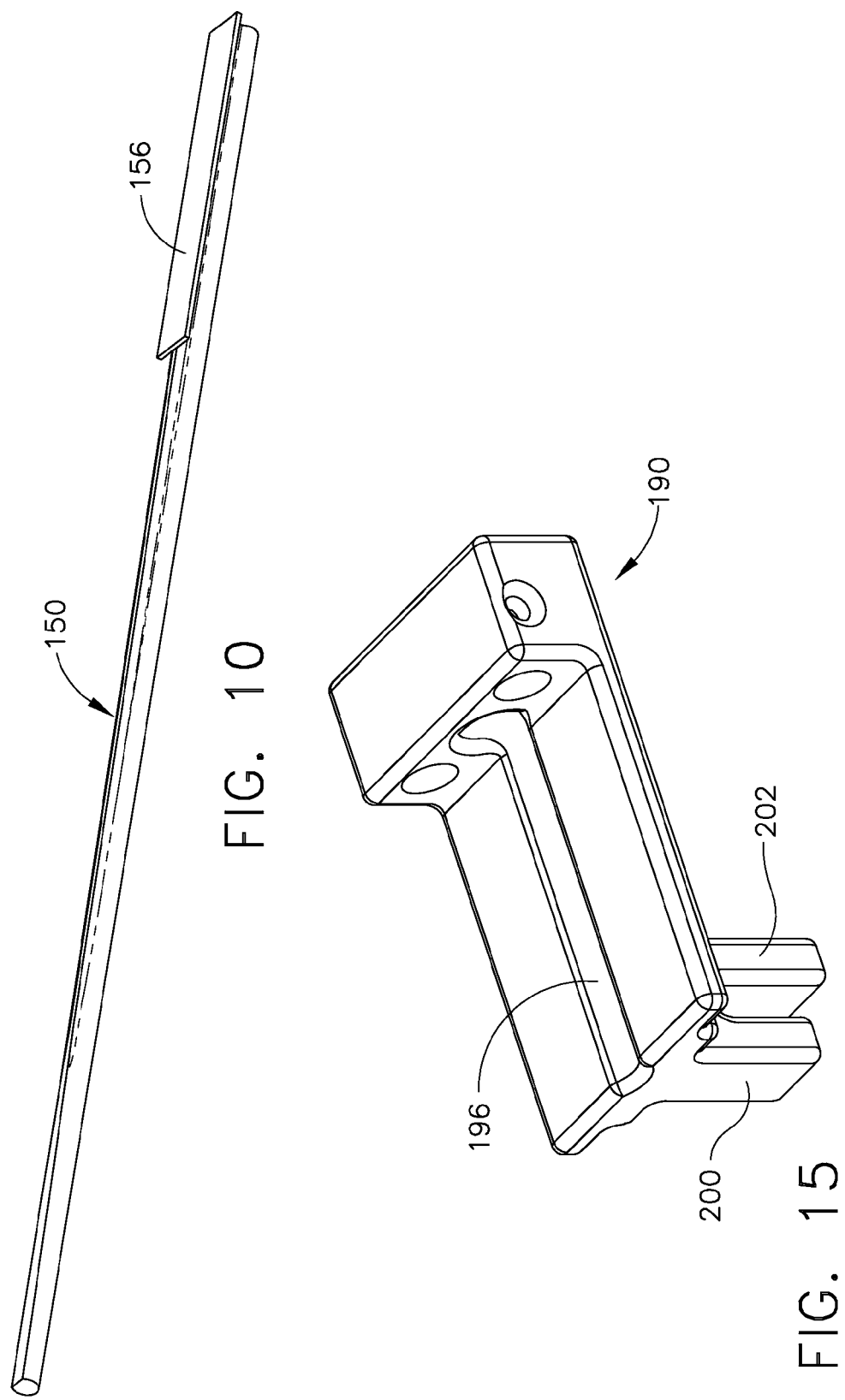

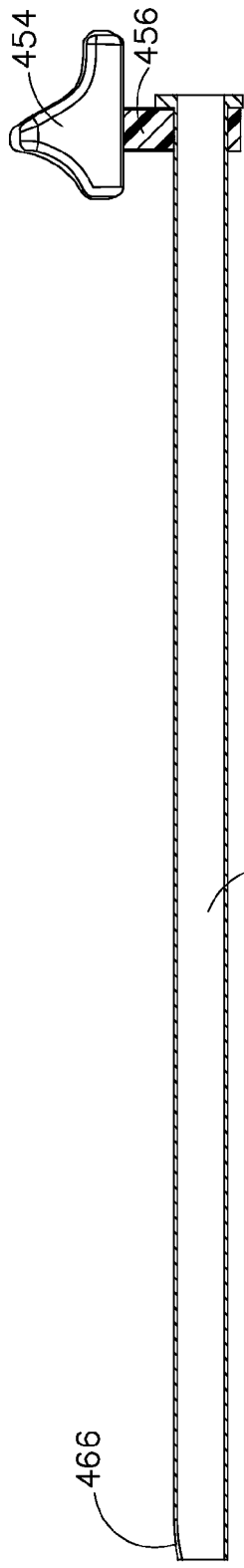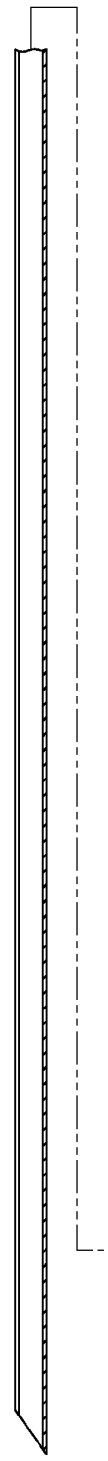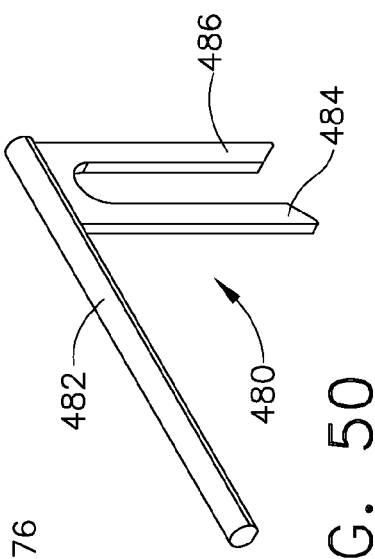
FIG. 46
FIG. 51
FIG. 50

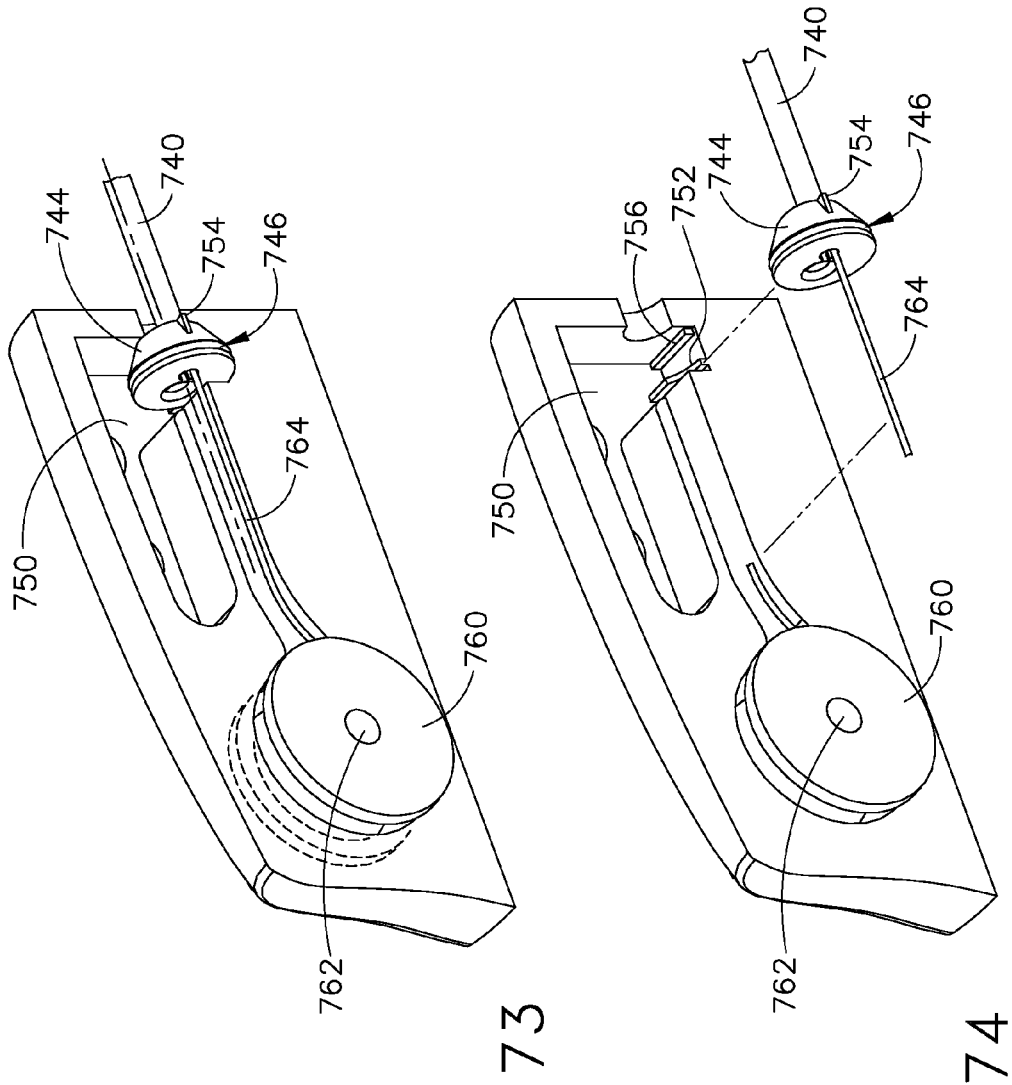

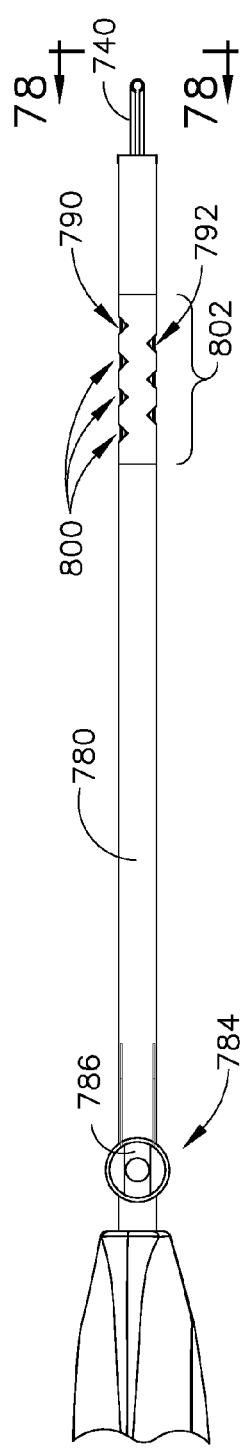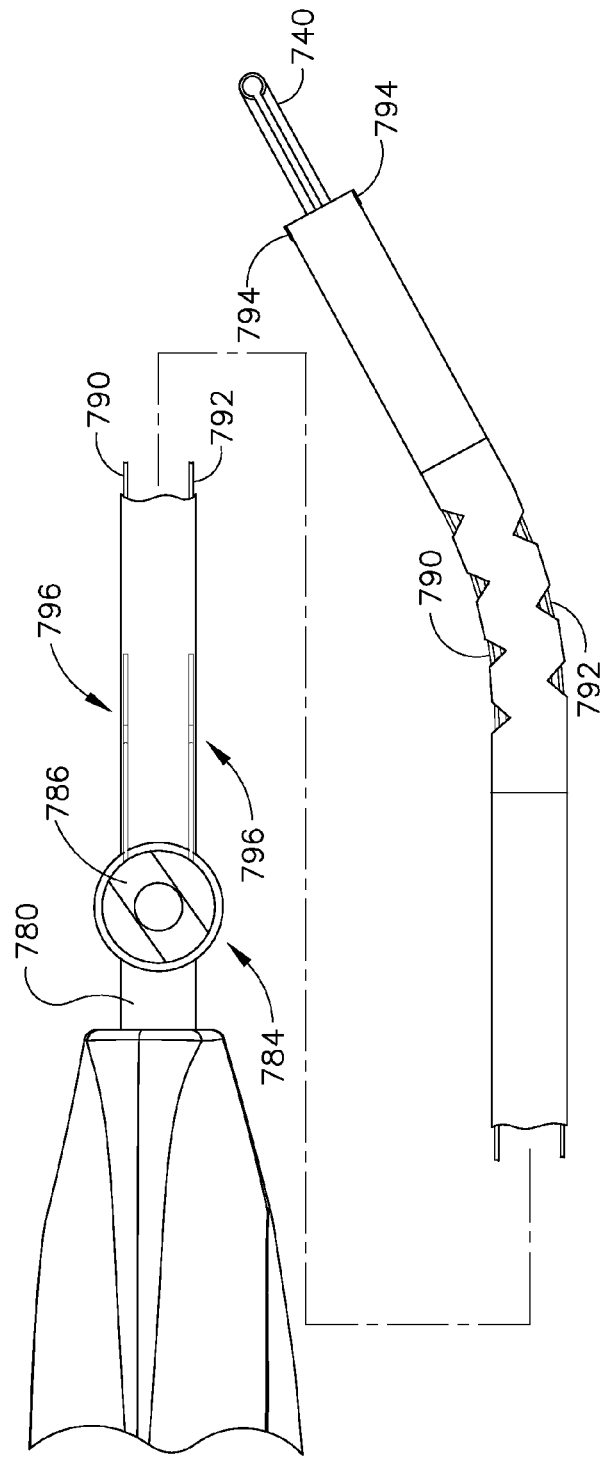
FIG. 77
FIG. 79

METHOD FOR DEPLOYING FASTENERS FOR USE IN A GASTRIC VOLUME REDUCTION PROCEDURE

FIELD OF THE INVENTION

The present invention relates generally to surgical soft tissue approximation including gastric volume reduction surgery.

BACKGROUND OF THE INVENTION

Obesity is a medical condition affecting more than 30% of the population in the United States. Obesity affects an individual's personal quality of life and contributes significantly to morbidity and mortality. Obesity is most commonly defined by body mass index (BMI), a measure which takes into account a person's weight and height to gauge total body fat. It is a simple, rapid, and inexpensive measure that correlates both with morbidity and mortality. Overweight is defined as a BMI of 25 to 29.9 kg/m$^2$ and obesity as a BMI of 30 kg/m$^2$. Morbid obesity is defined as BMI$\geq$40 kg/m$^2$ or being 100 lbs. overweight. Obesity and its co-morbidities are estimated to cost in excess of $100 billion dollars annually in direct and indirect health care costs. Among the co-morbid conditions which have been associated with obesity are type 2 diabetes mellitus, cardiovascular disease, hypertension, dyslipidemias, gastroesophageal reflux disease, obstructive sleep apnea, urinary incontinence, infertility, osteoarthritis of the weight-bearing joints, and some cancers. These complications can affect all systems of the body, and dispel the misconception that obesity is merely a cosmetic problem. Studies have shown that conservative treatment with diet and exercise alone are ineffective for reducing excess body weight in the vast majority of patients.

Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resected portion of the small intestine. This resected portion of the small intestine is connected between the "smaller" gastric pouch and a distal section of small intestine allowing the passage of food therebetween. The conventional RYGB procedure requires a great deal of operative time and is not without procedure related risks. Because of the degree of invasiveness, post-operative recovery can be quite lengthy and painful and is not without some degree of morbidity and mortality. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing an early feeling of satiety. A band is placed around the stomach near the junction of the stomach and esophagus. The small upper stomach pouch is filled quickly, and slowly empties through the narrow outlet to produce the feeling of satiety. In addition to surgical complications, patients undergoing a gastric banding procedure may suffer from esophageal injury, spleen injury, band slippage, reservoir deflation/leak, and persistent vomiting. Other forms of bariatric surgery that have been developed to treat obesity include Fobi pouch, bilio-pancreatic diversion, vertical banded gastroplasty and vertical sleeve gastrectomy. As aspects of some of these procedures including RYGB involve stapling a portion of the stomach, many bariatric procedures are commonly referred to as "stomach stapling" procedures.

For morbidly obese individuals, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be ten percent over their ideal body weight and want to lose the excess weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss. Further, it is known that modest reductions in weight may significantly decrease the impact of comorbid conditions including, but not limited to, type 2 diabetes mellitus. For this reason as well, a low cost, low risk procedure with an exceptional safety profile would provide significant benefit to both patients and health care providers.

It is known to create cavity wall plications though endoscopic only procedures as a treatment for obesity. However, operating solely within the interior of the gastric cavity limits the plication depth that can be achieved without cutting. Furthermore, access and visibility within the gastric cavity is limited in a purely endolumenal procedure as the extent of the reduction increases.

A hybrid endoscopic/laparoscopic surgical procedure has been developed for involuting the gastric cavity wall to reduce stomach volume. In the hybrid gastric volume reduction (GVR) procedure, pairs of suture anchoring devices are deployed through the gastric cavity wall. Following deployment of the anchors, suture attached to each pair of anchors is cinched and secured to involute the cavity wall. This procedure is described in greater detail in co-pending U.S. patent application Ser. Nos. 11/779,314 and 11/779,322, which are hereby incorporated herein by reference.

To facilitate the hybrid endoscopic/laparoscopic GVR procedure (e.g., reduction gastroplasty), it is desirable to have a simple, low cost means for deploying fasteners into the gastric cavity. While the GVR procedure can be performed using a needle and suture, such an approach requires a highly skilled surgeon and can be time consuming. Accordingly, it is desirable to have a device that can discharge fasteners in response to a triggering action by the surgeon. It is desirable that the device deploy fasteners through a laparoscopic port to maintain the minimally invasive nature of the procedure. Additionally, it is desirable to have a laparoscopic fastener deploying device that is inexpensive and easy to use. Further, it is desirable to have a fastener deploying device that can repeatedly deploy one or more fasteners from a disposable cartridge, and which can be easily and quickly reloaded with additional cartridges to deploy as many fasteners as deemed necessary by the surgeon. Furthermore, it is desirable that the device be reloadable with additional cartridges without the need to remove the device from the laparoscopic port. The present invention provides a reloadable fastener deploying device with a replaceable fastener cartridge which achieves these objectives.

BRIEF DESCRIPTION OF THE DRAWINGS

FIGS. 9A-9F are alternative exemplary embodiments for a needle usable with the fastener deployment device;

FIG. 10 is a perspective view of the pushrod;

FIG. 15 is a perspective view of the force transferring member;

FIG. 46 is a side, partially sectional view showing the connection between the sheath and button;

FIG. 50 is a perspective view of the force transferring member;

FIG. 51 is a side, cross-sectional view of the needle;

FIG. 73 is a side, perspective view showing the proximal end of the cartridge with half of the cartridge housing removed;

FIG. 74 is a side, perspective view of the cartridge, similar to FIG. 73, showing the base and shaft pulled out from the cartridge housing;

FIG. 77 is a top view of the distal end of the device, showing the device tip in a neutral, straight position;

FIG. 79 is a top view of the distal end of the device, showing the device tip curved in a counterclockwise direction;

DETAILED DESCRIPTION OF THE INVENTION

Figure 1:
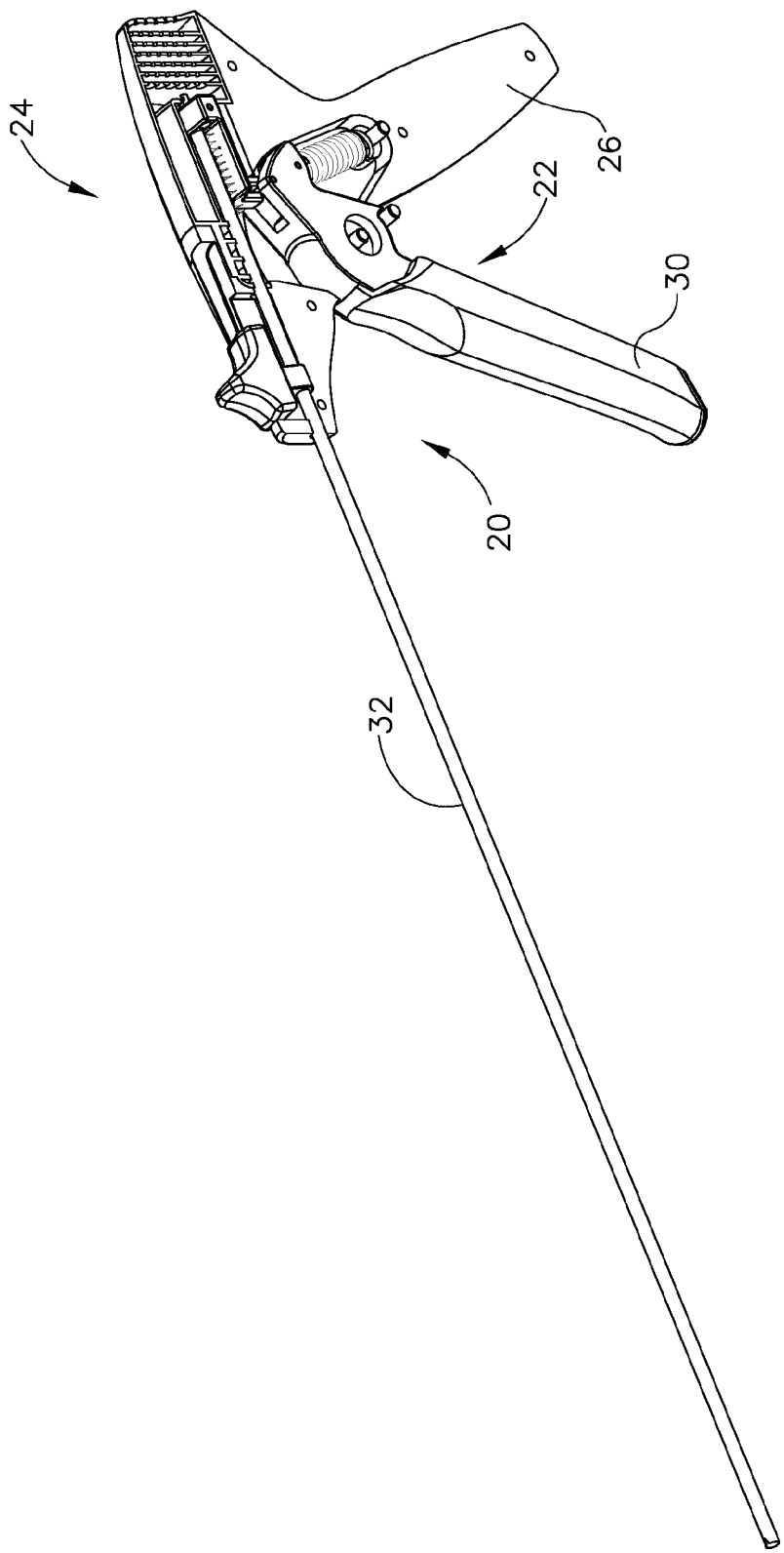
FIG. 1 is a perspective view of a first embodiment for a fastener deploying device with a replaceable cartridge.
Figure 2:
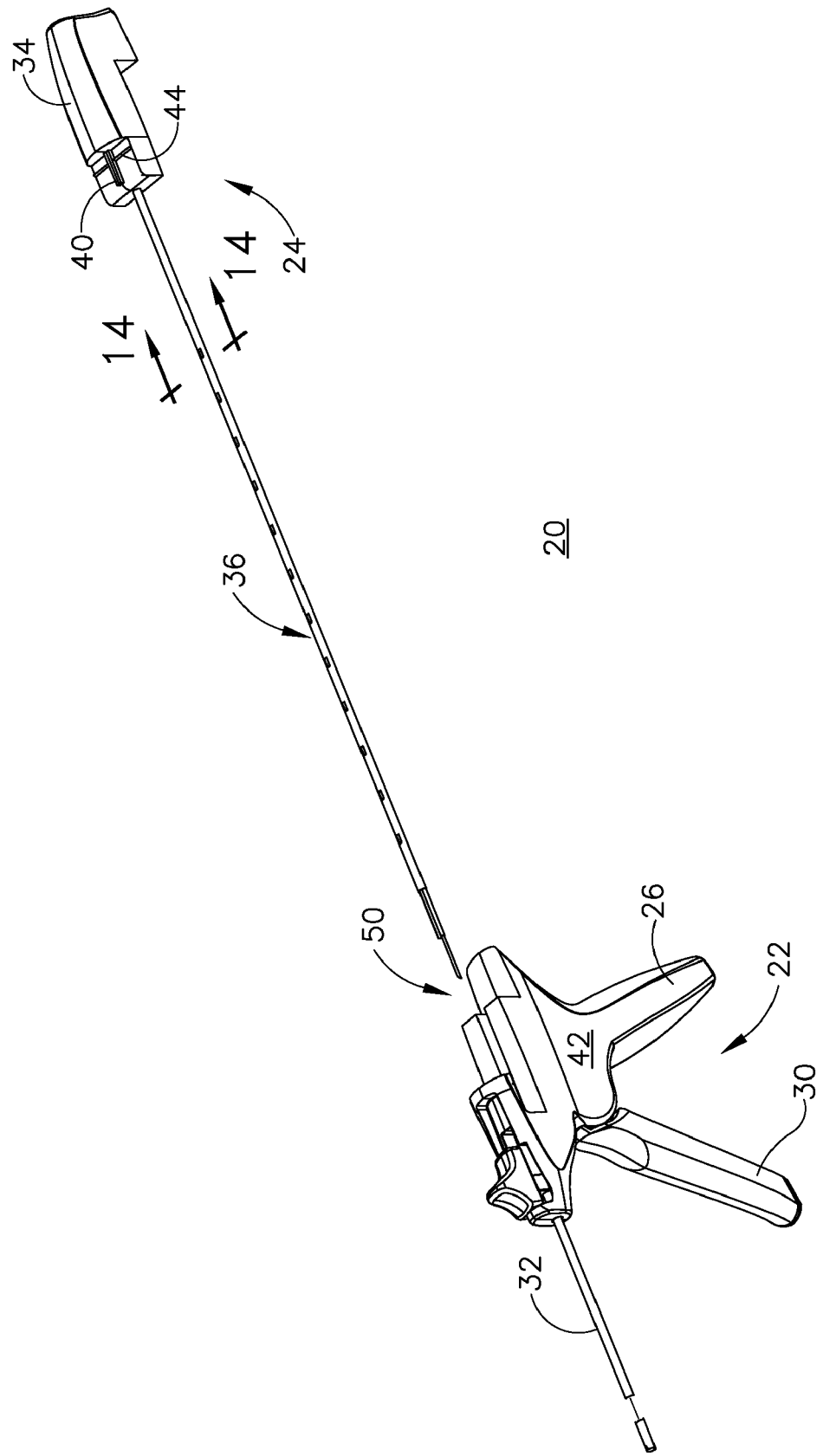
FIG. 2 is a perspective view of the device shown in FIG. 1, showing the cartridge aligned for attachment to the handle.

Referring now to the drawing figures, in which like numerals indicate like elements throughout the views, FIG. 1 illustrates a first exemplary fastener deploying device 20 for deploying fasteners during a laparoscopic surgical procedure. Fastener deploying device 20 includes a handle 22 for manipulating the device and a removable fastener cartridge 24. FIG. 2 shows the handle 22 and fastener cartridge 24 separated, with the cartridge in position for attachment to the handle. Handle 22 includes a pistol grip 26 and an actuator, such as a manually movable trigger 30. An elongated, protective sheath 32 extends distally from handle 22. Sheath 32 has sufficient length (on the order of 18") to enable use within an obese patient at numerous trocar access sites. Likewise, sheath 32 is sized to allow for passage through a small (3-5 mm) diameter trocar. Cartridge 24 includes a housing 34 and an elongated, distally extending fastener retainer 36. Fastener retainer 36 is sized to fit inside of sheath 32 when the cartridge is attached to the handle.

As shown in FIG. 2, fastener cartridge 24 is attached to the proximal end of handle 22. Handle 22 and cartridge 24 include coupling members for releasably attaching the cartridge to the handle. The coupling members allow for a rapid and secure removal and replacement of a cartridge. The coupling members may include an axially extending rib 40 adjacent the distal end of cartridge housing 34. Rib 40 slides through a groove 46 on handle 22 (shown in FIG. 3) to align and mate the cartridge to the proximal end of the handle. Rib 40 includes angled side faces which expand apart in a proximal direction. The expanding width of rib 40 produces resistance between the rib and coupling groove 46 to aid in retaining the cartridge on the handle. A step 44 (shown in FIG. 2) may be provided on cartridge 24 adjacent to rib 40. Step 44 engages a notch 48 on the handle as the cartridge rib 40 is slid into groove 46 to lock the cartridge onto the handle. The proximal end of handle 22 is cutaway, as indicated at 50, to accommodate the cartridge. As cartridge 24 is slid onto the proximal end of handle 22, fastener retainer 36 is inserted into and substantially through sheath 32. When a cartridge 24 is fully loaded onto handle 22, the distal tip of fastener retainer 36 is positioned adjacent the distal end of protective sheath 32.

Figure 3:
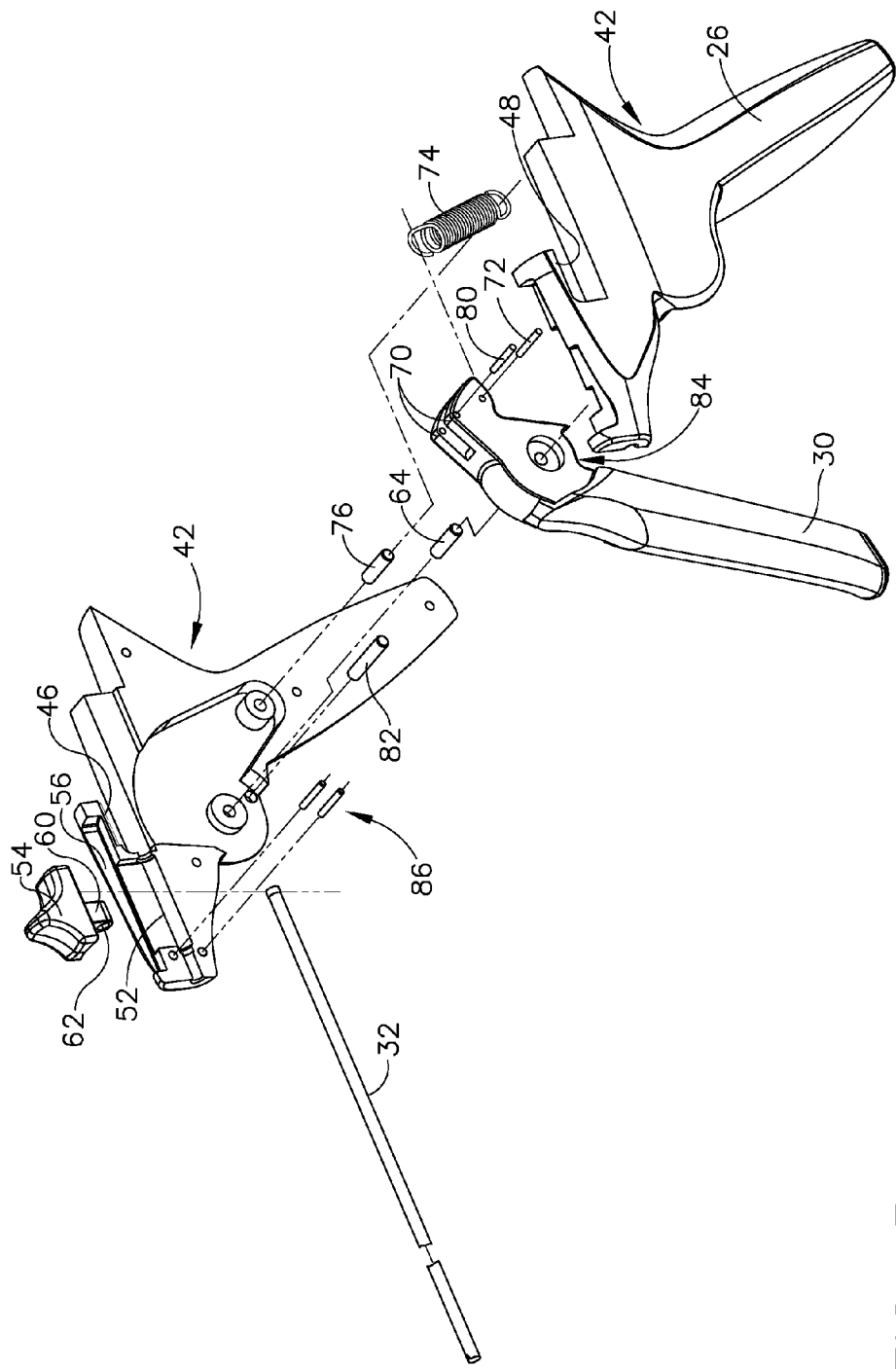
FIG. 3 is an exploded view of the handle of the deployment device.

FIG. 3 illustrates handle 22 in greater detail. As shown in FIG. 3, handle 22 comprises a housing 42 formed in sections which are joined together during the manufacturing process by any of a number of suitable means known in the art. Each section of the handle housing 42 includes a concave, longitudinally extending channel 52 (only one channel is shown in the Figure). Channels 52 combine together in the assembled housing to form a cylindrical passageway for slidingly retaining protective sheath 32. A button 54 is mounted on the top of housing 42 to slide within a track 56 recessed into the outer surface of the housing. A connector 60, having a bore 62 formed therethrough, extends beneath button 54 and into the passageway formed by channels 52. The proximal end of sheath 32 extends through the passageway and into bore 62 to attach the sheath to connector 60. Attaching sheath 32 to connector 60 enables the sheath to be advanced and retracted within housing 42 as button 54 is manually reciprocated along the surface of the handle.

As mentioned above, handle 22 includes a manually operable trigger 30 for expelling fasteners from an attached cartridge. Trigger 30 pivots about a pin 64 connected between the sides of handle housing 42. When the grip of trigger 30 is squeezed, the trigger pivots about pin 64 to rotate the upper end of the trigger distally within housing 42. The upper end of trigger 30 is divided into a pair of sidewalls 70. A first, spring retaining pin 72 extends perpendicularly between the sidewalls to connect a return spring 74 to the trigger. The opposite end of return spring 74 is connected to the handle housing 42 by a pin 76. A deploying pin 80 extends perpendicularly between trigger sidewalls 70, above spring retaining pin 72. Deploying pin 80 engages a force transferring member in an attached cartridge as trigger 30 pivots about pin 64, as will be described in more detail below. A trigger stop pin 82 extends through housing 42 beneath the pivot point of trigger 30. Stop pin 82 rides along the curved undersurface of trigger 30 between opposing end faces, as indicated at 84. Stop pin 82 rests against the proximal end face of surface 84 when trigger 30 is open. When trigger 30 is squeezed, pin 82 advances from the proximal face to the distal face along the curved surface. Stop pin 82 prevents trigger 30 from opening too far when the squeezing force on the trigger is released. Additional pins, such as those indicated by reference numeral 86, may be provided between the sections of handle housing 42 to aid in holding the housing together.

Figure 4:
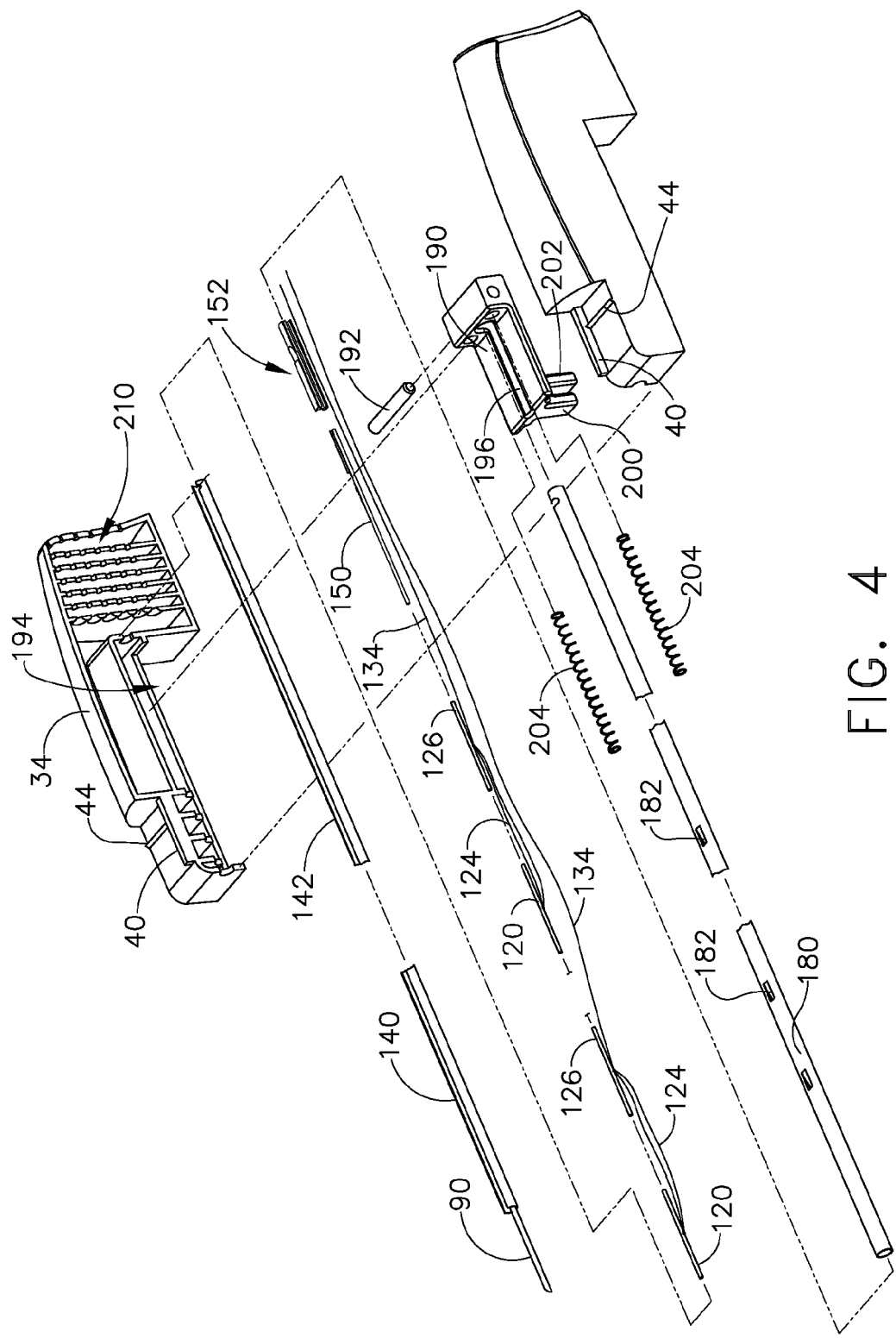
FIG. 4 is an exploded view of the cartridge of the deployment device.
Figure 5:
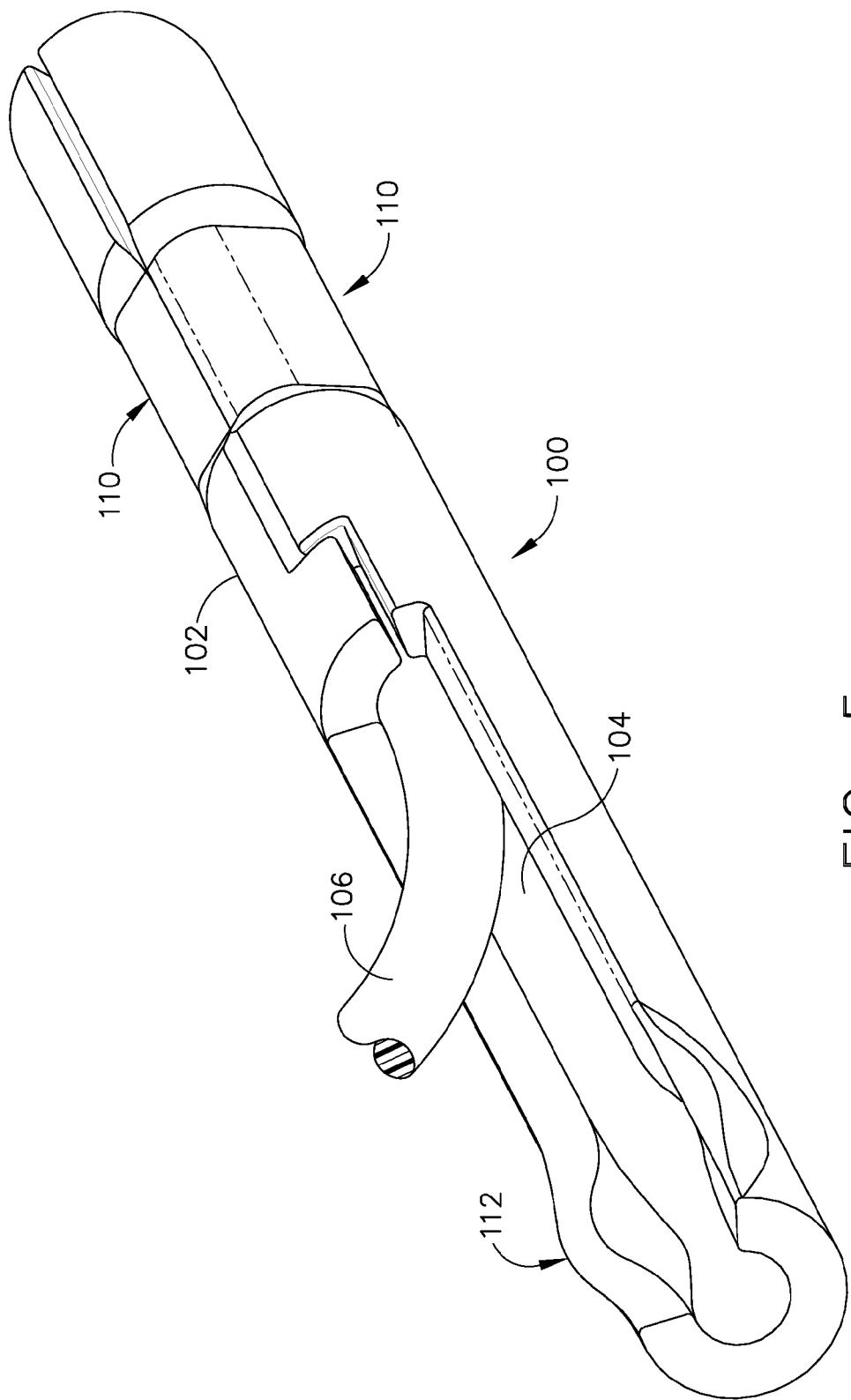
FIG. 5 is a perspective view of an exemplary T-Tag anchoring device.

FIG. 4 illustrates cartridge 24 in greater detail. As shown in FIG. 4, cartridge 24 contains at least one fastener and a tissue penetrating member for inserting the fastener into tissue, such as a gastric cavity wall. The penetrating member can be a needle having a slotted lumen that extends proximally from a sharpened tip, through the length of the needle, for retaining the fasteners. The needle can have a number of different shapes and configurations, and can be formed from injection molded plastic, be extruded in a plastic or ceramic material, or fabricated from sheet metal in a progressive die operation. Various treatments, coatings, and mechanical alterations can be used to enhance and/or prolong the sharpness of the needle while minimizing the size of the resulting defect. In the embodiments shown and described below, the needle at least partially retains and deploys one or more tissue fasteners. Preferably, a fastener comprises a pair of anchoring devices connected together by a non-resilient, flaccid material which does not resist deformation under compressible loads. An example of such a material is suture. In the embodiments described herein, the anchoring devices are T-Tag type suture anchors, an example of which is shown in FIG. 5. This exemplary T-Tag anchor 100 comprises an elongated tube 102 having an opening or slot 104 extending approximately one-half the length of the tube. The remaining length of the tube is formed into a closed cylindrical shape. One end of a length of suture 106 is inserted into the closed length of the tube. The suture end is retained within the tube by crimping a portion of the midsection of the cylindrical length, as indicated by the arrows 110. The remaining length of suture 106 protrudes freely out of the slot 104. An outwardly extending projection or bulge 112 may be formed along the length of the T-Tag anchor 100. Bulge 112 creates friction between the inner diameter of the needle and the T-Tag anchor when the anchor is held within the needle lumen. This friction between the needle and the T-Tag anchor can be used alone or in conjunction with features on or in the needle to prevent the anchor from being unintentionally released from the device.

Figure 6:
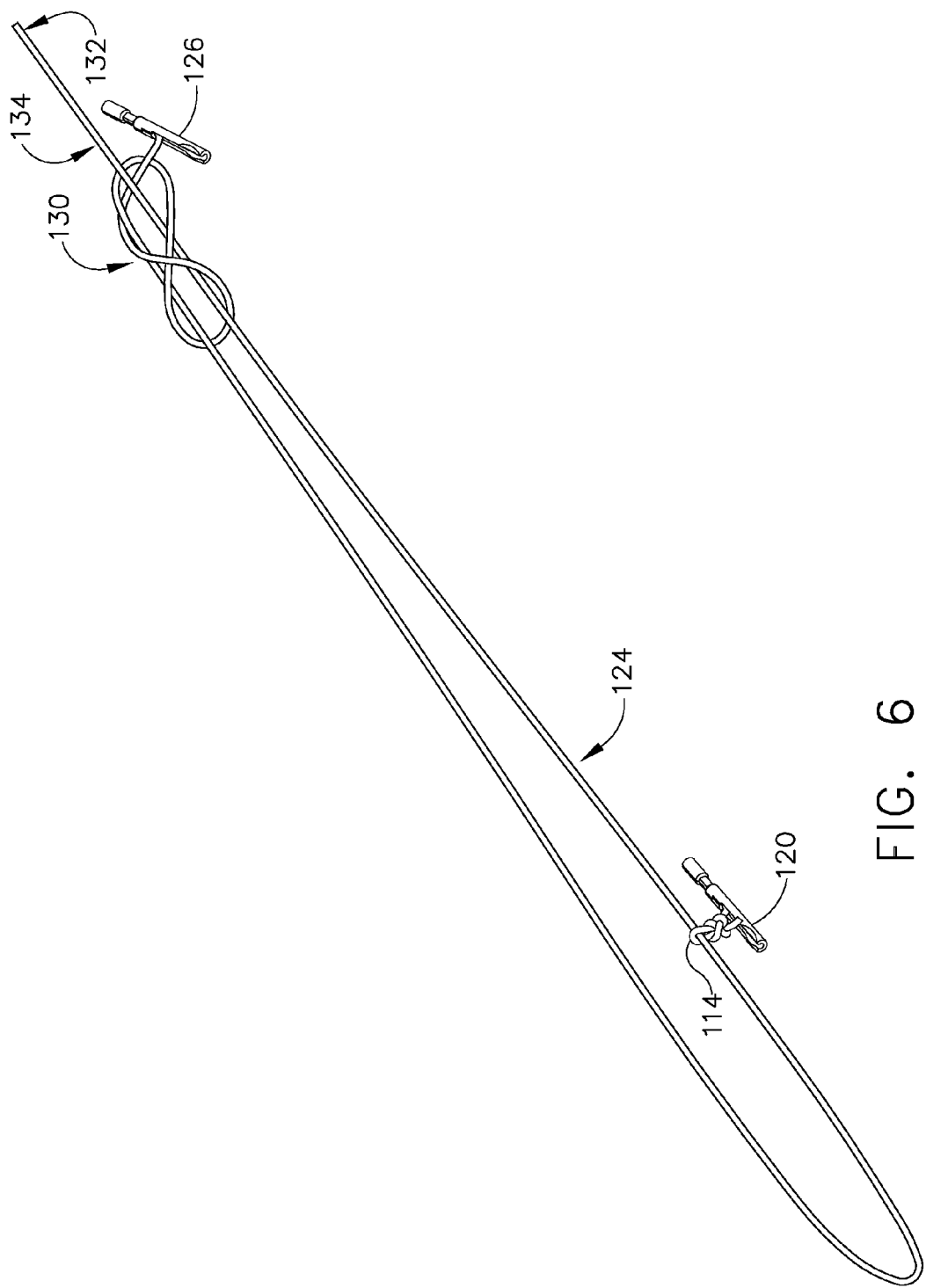
FIG. 6 is an isometric view of a slip knot formed between a pair of T-Tag anchors, showing the knot in a loosened form.
Figure 7:
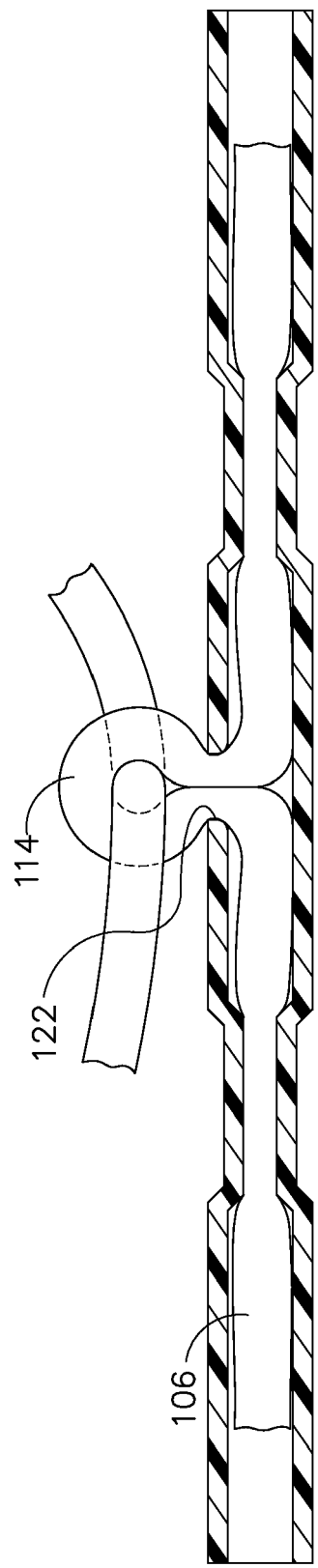
FIG. 7 is a side view of a second exemplary T-Tag anchoring device, showing a second method for forming a suture loop.

In the exemplary embodiments, the pair of T-Tag anchors is preferably pre-tied together prior to loading the tags into the needle lumen. To tie the T-Tag anchors together, a loop or other slidable connecting member 114, such as shown in FIG. 6, is formed in the free end of suture from a first one of the T-Tag anchors 120. One skilled in the art will clearly recognize that loop 114 may be formed by a variety of different types of knots, such as, for example, a square knot, one or more ½ hitch knots, or a hangman's knot. A slidable connecting member can also be formed by altering the T-Tag anchor, as shown in FIG. 7, so that both ends of the suture length 106 are retained within the anchor, and a loop 114 of the suture protrudes from an opening 122 in the T-Tag to serve as the connecting member. In yet another embodiment, the T-Tag itself may have a hole through which suture length 124 (shown in FIG. 6) is passed.

To connect the anchor pair, a length of suture 124, attached at one end within a second T-Tag anchor 126, is passed through the suture loop 114 of the first T-Tag anchor 120 to allow the first T-Tag anchor to slide relative to the second T-Tag anchor along the length of the suture. After first T-Tag anchor 120 is slidingly connected to the suture length 124, a knot is formed in the suture. The suture knot serves to lock the T-Tag anchors at the determined spacing when the anchors are under load following deployment. FIG. 6 shows a one-way slip knot 130 formed within the suture length 124 to draw the T-Tag anchors 120, 126 together.

Following deployment of the T-Tag anchor pair, knot 130 is tightened to set the distance between the knot and the second T-Tag anchor 126, while allowing a doubled over length of the suture 124 between the T-Tag anchors to be reduced. Once T-Tag anchors 120, 126 are deployed and fixed into the tissue, pulling on the loose end 132 (or any section of suture 134 proximal to second T-Tag anchor 126) of suture length 124 relative to the fixed T-Tag anchors reduces the size of the doubled suture length to the desired spacing, or until it cannot be further reduced because of loop 114. As suture length 124 is reduced, the T-Tag anchors 120, 126 are drawn together. The final distance between the T-Tag anchors 120, 126 is defined by the distance from loop 114 to the first T-Tag 120, and the distance from knot 130 to the second T-Tag 126. The size of loop 114 may be used to adjust this overall minimum distance. Additionally, where loop 114 is formed by tying a knot in the T-Tag anchor suture, suture knot 130 may be pre-tied in a length of suture before the T-Tag anchors are attached. Following formation of the slip knot 130, first T-Tag anchor 120 is attached to the suture length 124 by tying a knot to form loop 114. Second T-Tag anchor 126 is attached to an end of the suture length 124 by crimping the end within the anchor. The end of the suture may be crimped within T-Tag anchor 126 after knot 130 is tightened. The slip knot 130 shown in FIG. 6 is only one example of a suitable knot for connecting together a pair of T-Tag anchors. One skilled in the art will recognize that other types of slip knots may be tied such that one anchor is slidably attached to a doubled over portion of the slip knot, while the other anchor is secured to a tail or free end of the slip knot, to permit one-way cinching when forces seeking to loosen the knot are applied only to the anchors in the system.

Figure 8:
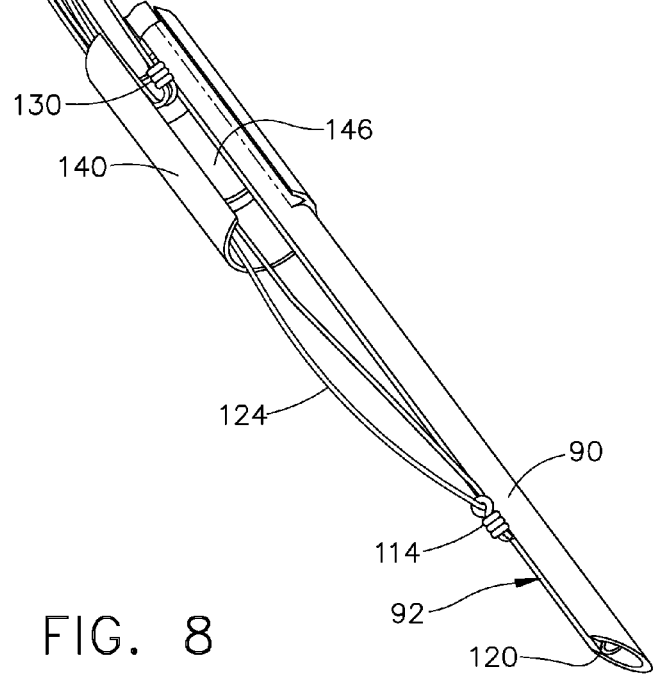
FIG. 8 is a perspective view of an exemplary needle embodiment, showing the needle affixed to an inner tube, and a fastener positioned within the needle lumen.

After the T-Tag anchors are tied together, the anchor pair is preferably loaded into the needle lumen, such that the first "looped" T-Tag anchor 120 deploys initially, followed by the second "attached" T-Tag anchor 126, although the order may be switched. When loaded into the deployment needle, the T-Tags are stacked one against the other, and each T-Tag anchor is positioned so that the suture opening 104 is aligned with the needle lumen slot. Multiple pairs of T-Tag anchors may be loaded into needle 90, with the particular number of fasteners (i.e. anchor pairs) varying depending upon the length of the fastener retainer and/or the requirements and intended results of the surgical procedure. FIG. 8 illustrates an exemplary embodiment for a needle 90 in which the needle includes a slotted opening 92 extending parallel to the axis of the needle. To load T-Tag anchors into needle 90, the anchors are passed down the axis of the needle lumen and stacked against each other from the distal end of the lumen. Within the lumen, the T-Tag anchors 120, 126 are oriented such that the suture from each tag exits the tag midsection at a normal angle to the tag axis. Needle 90 is shaped such that when the T-Tag anchors are loaded into the needle, loop 114 and knot 130 are at least partially concealed within the needle lumen, as shown in FIG. 8, with the suture length 134 extending outside of the needle lumen through slotted opening 92.

FIGS. 9A-9F illustrate several of the numerous additional configurations that are possible for a needle in the fastener deploying device embodiments. In each of these examples, the needle includes a lumen for retaining the fasteners and a slotted opening for passing suture from the T-Tags out of the needle. Although not shown, the distal end of each of these needles may include features (e.g., reduced cross sectional area) that serve to prevent the unintentional release of T-Tags from the needle. These features may engage or interact with any component of the fastener (e.g., T-Tag anchor, knot, loop, etc.).

Alternative fastener concepts are also compatible with the cartridge embodiments described herein. One such example comprises two tissue anchors connected by a non-resilient flexible material such as suture. In this and related embodiments, one strand of suture is securely connected to a tissue anchor. This strand is slidably connected to a second tissue anchor. The slidable connection to the second anchor is such that the anchor is only permitted to slide in the direction over the suture towards the first anchor. Features enabling this one way sliding feature may be contained within the suture or the second anchor. The use of barbed suture clearly meets this purpose. However, the use of one way locks in or on the second tissue anchor itself can also achieve this purpose. Numerous one-way locking mechanisms are well understood to those skilled in the art and may be employed in this circumstance without significant changes to the cartridges or the devices that deploy the tissue anchors described herein. Numerous tissue anchors are also compatible with the current inventions including anchors designed for deployment into or through the tissue wall.

As shown in FIGS. 4 and 8, needle 90 is affixed within a cylindrical inner tube 140. Needle 90 may be affixed to inner tube 140 by welding or adhesives, or the tube and needle may be extruded together during the manufacturing process. Inner tube 140 includes a longitudinally-extending opening 142 through the wall of the tube. Needle 90 is offset from opening 142 and retained against the inner diameter of the tube. Within tube 140, needle 90 is oriented so that needle slot 92 is open to the interior of the tube to enable suture 134 from the T-Tag anchors 120, 126 to pass from the needle and into the inner diameter of the tube. A series of axially-spaced cutouts 146 are formed along the length of inner tube 140. The distal end of each cutout 146 is bent into the interior of inner tube 140, while the proximal end of each cutout remains attached to the wall of the tube. Cutouts 146 taper inwardly in a distal direction so that the distal end of each cutout protrudes into the interior of tube 140. Cutouts 146 are spaced apart along inner tube 140 a distance equal to the length of a T-Tag anchor. The proximal end of inner tube 140 is affixed to cartridge housing 34 so that the inner tube remains stationary during fastener deployment.

Figure 11:
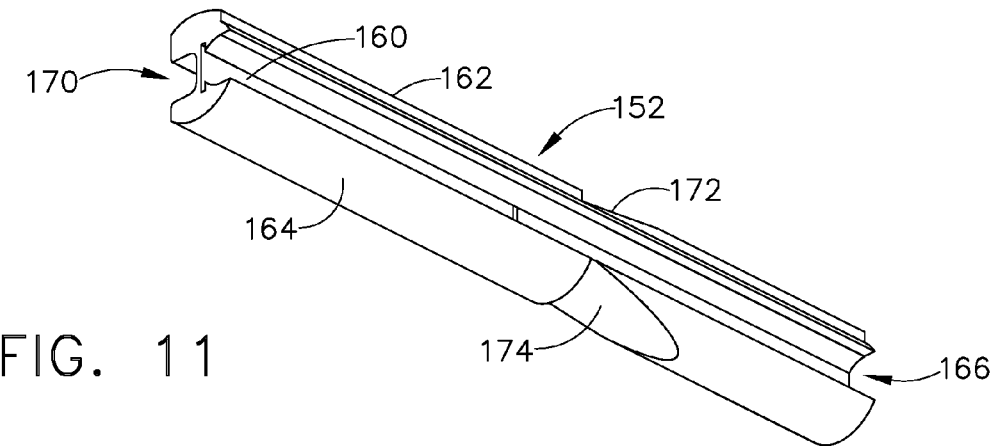
FIG. 11 is a perspective view of the pushrod driver showing a first notch and needle channel of the driver.
Figure 12:
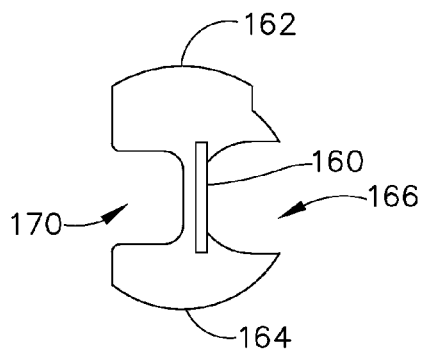
FIG. 12 is an end view of the pushrod driver shown in FIG. 11.
Figure 13:
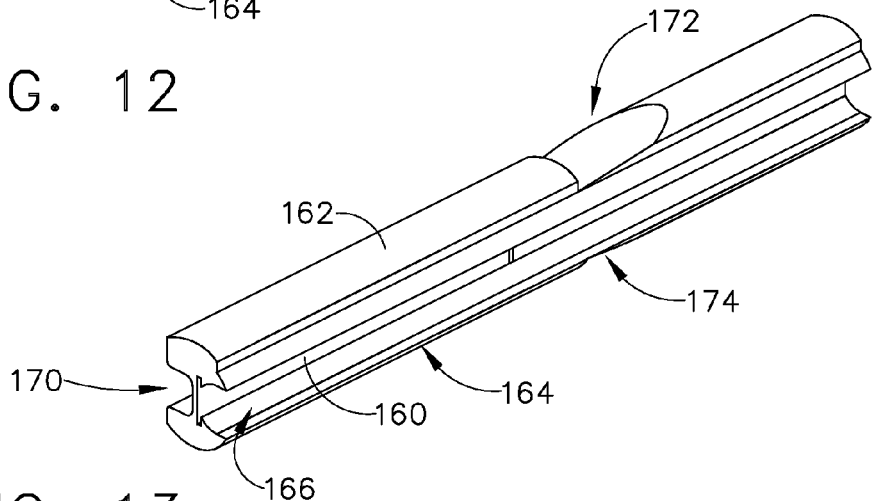
FIG. 13 is a second perspective view of the pushrod driver shown in FIG. 11, showing the distal face and a second notch in the driver.

As shown in FIG. 4, a cylindrical pushrod 150 is disposed within the lumen of needle 90. Pushrod 150 extends through the needle lumen with the distal end of the pushrod in contact with the proximal end of the T-Tag anchor stack. The proximal end of pushrod 150 is connected to a pushrod driver 152 for advancing the pushrod within the needle lumen. A mating feature is provided on pushrod 150 for securing the pushrod to the pushrod driver. In the embodiment shown in FIG. 10, the mating feature is an axially extending block 156 attached to the outer surface of the pushrod. Block 156 is inserted into an axially-extending recess 160 formed into the body of the pushrod driver 152, as shown in FIGS. 11-13, in order to connect the pushrod to the pushrod driver. With block 156 inserted into recess 160, pushrod 150 is advanced distally within the needle lumen by pushrod driver 152. Pushrod driver 152 is sized and shaped to pass through inner tube 140, with a first side 162 of the driver extending through tube opening 142. A second, opposing side 164 of pushrod driver 152 is curved to conform to the concave inner diameter of tube 140. An axially-extending needle channel 166 is formed between first and second sides 162, 164. Recess 160 is formed on the inside of the needle channel. Needle channel 166 is sized to accommodate needle 90, so that pushrod driver 152 can pass about the perimeter of the needle as the driver advances through inner tube 140. Opposite needle channel 166, pushrod driver 152 includes a longitudinally-extending suture channel 170 for accommodating the lengths of suture 134 from the T-Tag anchors stacked within needle 90. Diametrically opposed notches 172, 174 are formed into first and second pushrod driver sides 162, 164. Notches 172, 174 include a distal face extending perpendicular to the pushrod driver axis. Proximal of the distal face, notches 172, 174 incline gradually back to the outer pushrod driver diameter.

Figure 14:
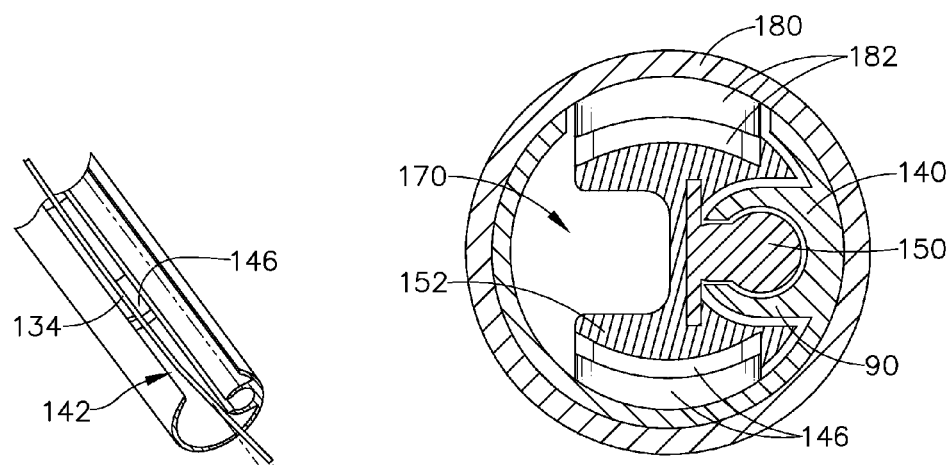
FIG. 14 is a cross-sectional view of the fastener retainer, taken along lines 14-14 in FIG. 2.

Returning now to FIG. 4, the fastener retainer includes an elongated, tubular outer shaft 180 extending distally from cartridge housing 34. Shaft 180 has an inner diameter that is slightly larger than the outer diameter of tube 140, so that the shaft can extend concentrically over the inner tube. A row of axially-spaced cutouts 182 are formed along the length of shaft 180. The cutouts on shaft 180 are spaced apart a distance equal to the length of a T-Tag anchor. The distal end of each cutout 182 is bent into the interior of shaft 180, while the proximal end remains attached to the wall of the shaft. Cutouts 182 taper inward in a distal direction, so that the distal end of each cutout protrudes the greatest extent into the interior of shaft 180. Shaft 180 and inner tube 140 both have a cylindrical shape to enable the outer shaft to advance over the inner tube to deploy fasteners. Outer shaft 180 and inner tube 140 are circumferentially aligned such that the cutouts 182 on the outer shaft are positioned diametrically opposite of the cutouts 146 on inner tube 140, as shown in FIG. 14. Aligning the cutouts 146, 182 in diametrically opposite positions enables each series of cutouts to engage a different one of the notches 172, 174 on pushrod driver 152. Accordingly, as outer shaft 180 is advanced, shaft cutouts 182 engage notch 172 on the first side 162 of pushrod driver 152, while the inner tube cutouts 146 engage notch 174 on the second side 164 of the pushrod driver. Outer shaft 180 is circumferentially oriented with respect to inner tube 140 such that outer shaft cutouts 182 pass through opening 142 in inner tube 140 as the outer shaft advances over the inner tube.

Figure 16:
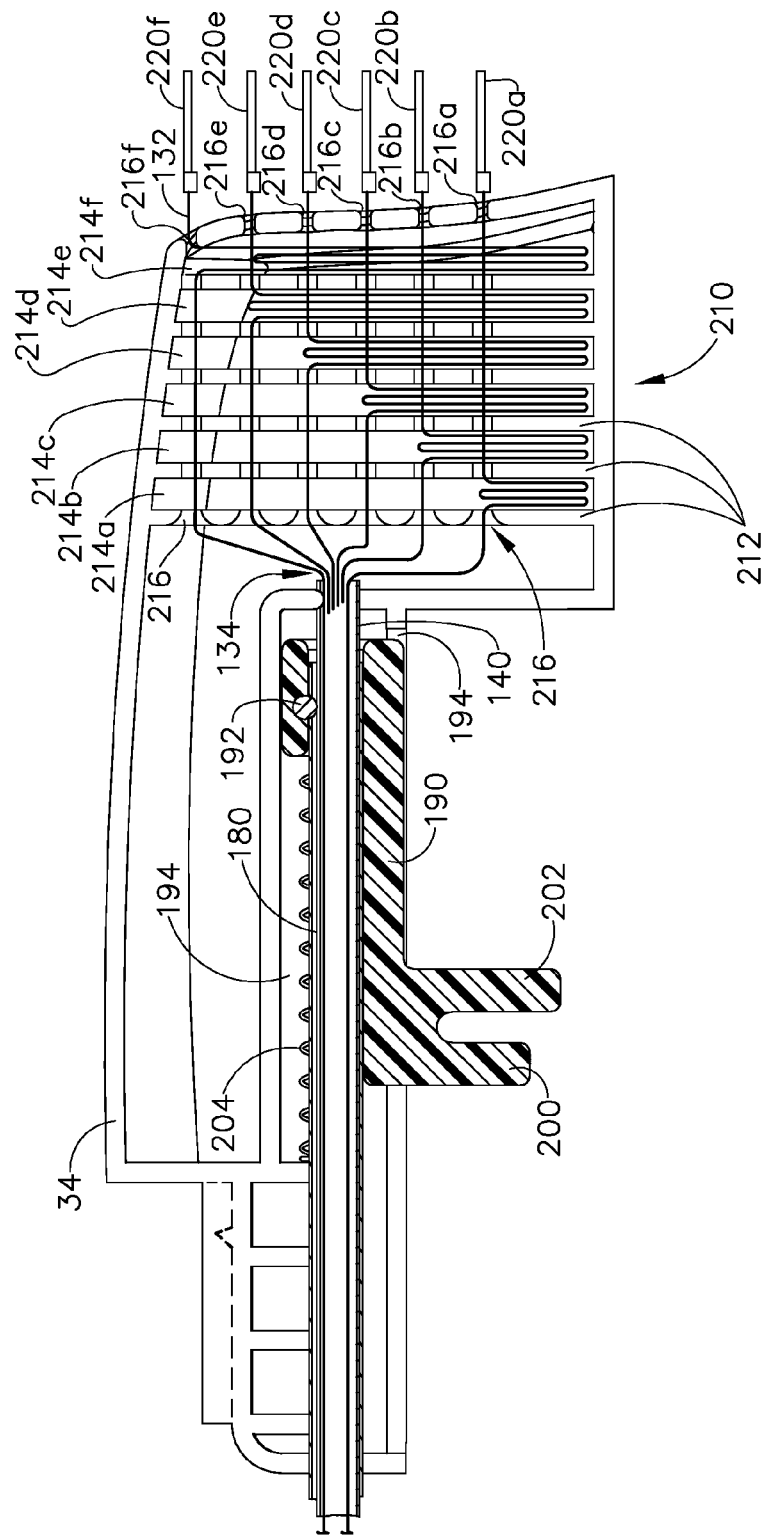
FIG. 16 is a side, sectional view of the proximal end of the cartridge.

As shown in FIG. 4, the proximal end of outer shaft 180 is attached to a force transferring member 190 within cartridge 24. Shaft 180 extends through an axial groove 196 on force transferring member 190. A pin 192 extends perpendicular to shaft 180, through force transferring member 190 and an opening in the wall of the shaft, to lock the shaft to the member. Force transferring member 190 reciprocates through a track 194, formed in cartridge housing 34, during deployment of a T-Tag anchor. The proximal end of inner tube 140 passes through outer shaft 180 and force transferring member 190. Inner tube 140 is affixed to the cartridge housing 34 proximal of force transferring member 190. As shown in FIG. 16, inner tube 140 may be held stationary within cartridge housing 34 by extending a downward directed edge of the housing into an opening in the wall of the tube. As shown in FIGS. 15 and 16, a pair of spaced legs 200, 202 extend downwardly from force transferring member 190 beneath the cartridge housing 34. The downward direction of legs 200, 202 enables the legs to engage deploying pin 80 within handle 22 when a cartridge is attached to the handle. As shown in FIG. 4, springs 204 extend between force transferring member 190 and cartridge housing 34 to bias the transferring member into an initial, retracted position.

As mentioned above, suture lengths 134 from the T-Tag anchors in needle 90 extend through the interior of tube 140 and suture channel 170 of pushrod driver 152. At the proximal end of inner tube 140, suture lengths 134 pass into a suture compartment 210 within cartridge housing 34. As shown in FIG. 16, inside suture compartment 210 is a series of dividing walls 212. Dividing walls 212 may be molded into the body of cartridge housing 34, or separately formed and attached to the housing. The dividing walls 212 are spaced apart in a proximal direction to form suture retention sections 214 (individually labeled as 214a-214f) between each pair of the walls. Within suture compartment 210, each of the individual strands of suture 134 is placed into a separate suture retention section 214. A plurality of parallel rows of openings 216 are formed through each of the dividing walls 212 to allow for the passage of the suture lengths 134 from inner tube 140 to the individual retention sections 214, and from the retention sections out the proximal end of cartridge housing 34. Each strand of suture 134 extends through a different row of openings 216 in order to keep the individual strands from becoming tangled together within suture compartment 210. Each suture strand passes from inner tube 140 through a row of the openings 216 to a particular suture retention section 214. Within the section, the individual length of suture 134 is encircled upon itself and held between the dividing walls 214. From the suture retention section 214, the loose end of the suture strand 134 passes proximal through the remaining openings 216 and outside the end of cartridge housing 34. The exemplary suture compartment 210, shown in FIG. 16, contains six suture retention sections. However, the number of suture retention sections present within a cartridge of the present invention can vary depending upon the number of fasteners loaded within the cartridge, provided that the number of retention sections is either equal to or greater than the number of fasteners, so that each of the fastener suture lengths may be retained in a separate section.

Outside of cartridge housing 34, the loose end 132 of each suture length 134 is attached to a fastener identifying member, such as a pull tab 220. Each of the pull tabs, individually labeled as 220a-220f in FIG. 16, correspond to one of the fasteners in the cartridge. The individual suture lengths are organized within suture compartment 210 according to the position of the attached fastener within needle 90. In the example shown, suture from the distal most fastener within needle 90 is stored within the distal-most retention section 214a, the suture from the second most distal fastener is stored in the second most distal retention area 214b, and so forth. Pull tabs 220 are likewise identified outside of the proximal end of cartridge 24 according to the position of the attached fastener within the lumen of needle 90. In the embodiment shown in FIG. 16, pull tabs 220 extend from openings 216 at the proximal end of cartridge housing 34 in the order in which the fasteners are to be deployed from needle 90. Consequently, pull tab 220a, which is attached to the suture end extending from the bottom row of openings 216a, corresponds to the distal most fastener (i.e. pair of T-Tag anchors) in the needle lumen. Likewise, the second pull tab 220b, which is attached to the suture end 132 extending from the second lowest row of openings 216b corresponds to the second fastener to be deployed from needle 90, and so forth.

Each of the pull tabs 220 can be pulled back proximally from the end of cartridge 24 following deployment of the associated fastener, to cinch the suture 124 between the T-Tag anchors of the fastener. In FIG. 16, pull tabs 220 are shown vertically stacked in the sequence in which the tabs are to be pulled in order to cinch the suture of the attached fasteners. The cartridge of the present invention, however, may comprise a number of different arrangements of pull tabs, or other fastener identifying and cinching elements, provided the pull tabs or cinching elements distinguish between the suture lengths. As alternatives to physical position, identifying elements may include other distinguishing features such as, for example, alphanumeric characters or colors, to indicate the order in which the suture strands are to be pulled.

To deploy tissue fasteners during a laparoscopic reduction gastroplasty or other surgical procedure, a cartridge 24 is attached to the proximal end of handle 22 by sliding rib 40 through groove 46 on the underside of handle housing 42. Cartridge 24 is slid along handle 22 until step 44 snaps into notch 48 on the handle. As cartridge 24 slides onto handle 22, fastener retainer portion 36 of the cartridge is inserted through protective sheath 32. Additionally, as cartridge 24 advances over handle 22, legs 200, 202 on force transferring member 190 are moved into position above deploying pin 80. When cartridge 24 is secured to handle 22, leg 200 is located just above the distal edge of pin 80 and leg 202 is located just above the proximal edge of pin 80, as shown in FIG. 1. Cartridge 24 may be attached to handle 22 either before or after sheath 32 is inserted through a trocar.

With sheath 32 inside the trocar, handle 22 is manipulated to maneuver the sheath (and enclosed fastener retainer) to the desired location for the tissue fastener. At the desired location, button 54 is slid proximally through track 56 to draw the attached sheath 32 proximally, and expose the distal tip of needle 90. With needle 90 exposed at the distal end of the cartridge, handle 22 is manually pushed forward to penetrate the targeted tissue area with the needle tip. With needle 90 inside the tissue, trigger 30 is manually squeezed in the direction of pistol grip 26 to pivot the trigger about pin 64 in the handle. As trigger 30 pivots, deploying pin 80 rotates upward against transferring member leg 200. Pin 80 applies a distally directed force against leg 200 to advance force transferring member 190 within the cartridge and, correspondingly, outer shaft 180 distally over inner tube 140. To advance force transferring member 190, sufficient force must be applied through trigger 30 to overcome the counterforce of member biasing springs 204 and other sources of resistance within the deploying device 20 including but not limited to the friction of the T-tag anchors within the needle lumen.

Figure 17:
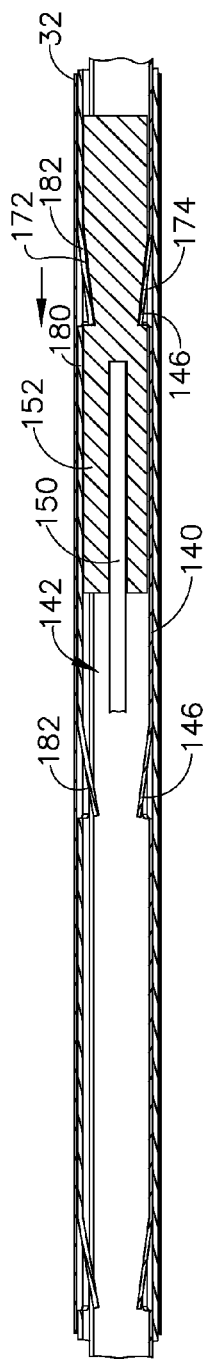
FIG. 17 is a simplified, sectional view of a portion of the fastener retainer, showing the retainer prior to actuation of the trigger.
Figure 18:
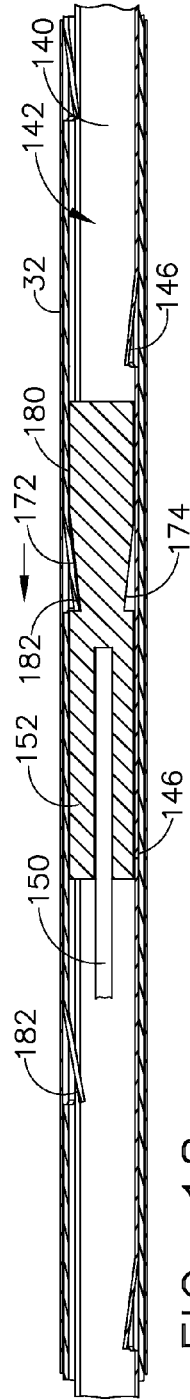
FIG. 18 is a simplified, sectional view of the fastener retainer, similar to FIG. 17, showing the pushrod and driver being advanced distally during fastener deployment.

Prior to fastener deployment, a cutout 182 on shaft 180 engages pushrod driver notch 172, as shown in FIG. 17. The cutout 182 which initially engages notch 172 depends upon the length of the anchor stack within the needle lumen, and the length of pushrod 150. The engaging cutout 182 is aligned with pushrod driver notch 174 when pushrod 150 contacts the proximal end of the anchor stack. In the initial position, notch 174 on the second side of pushrod driver 152 may or may not engage the proximal-most cutout 146 on inner tube 140, although the cutout is shown as engaging the notch in FIG. 17. As outer shaft 180 is advanced distally by force transferring member 190, the contact between shaft cutout 182 and the distal face of driver notch 172 causes pushrod driver 152 to move distally within inner tube 140, as shown in FIG. 18. As pushrod driver 152 advances, the driver advances pushrod 150 against the proximal end of the T-Tag anchor stack in needle 90. The contact force of the push rod against the T-Tag anchor stack slides the T-Tag anchor stack towards the open distal end of the needle. The distance which force transferring member 190 advances outer shaft 180 (and likewise the distance pushrod 150 is advanced by the outer shaft) during a single trigger stroke corresponds to the length of a single T-Tag anchor within the needle lumen. The force of the advancing push rod 150 expels the distal-most T-Tag anchor in the stack (i.e. first T-Tag anchor 120) from the needle and into or through the tissue. As the T-Tag anchor is deployed, the suture knot or loop 114 connected to the T-Tag is passed out of the needle through slot 92.

Figure 19:
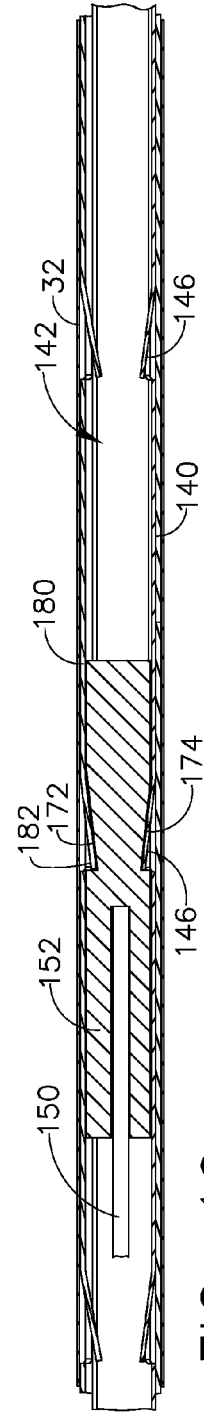
FIG. 19 is a simplified, sectional view of the fastener retainer, similar to FIG. 17, showing the pushrod driver indexed distally one position following deployment of a T-Tag anchor.

As the T-Tag anchor is exiting needle 90, outer shaft 180 is advancing pushrod driver 152 to a point where notch 174 on the driver is aligned with a cutout 146 on inner tube 140. As driver notch 174 reaches the cutout 146, the cutout (which to this point has been pressed outward by the outer diameter of the advancing pushrod driver) springs inward into the notch, with the distal face of the cutout engaging the normally extending face of the notch, as shown in FIG. 19. At the same time that the T-Tag anchor exits the tip of needle 90, the advancing force transferring member 190 bottoms out against the distal end of cartridge housing 34, providing tactile feedback to the surgeon that a T-Tag anchor has been deployed. While trigger 30 is being squeezed in the direction of grip 26, stop pin 82 rides along the curved surface 84 of the trigger, beneath pivot pin 64. As force transferring member 190 reaches the distal end of cartridge housing 34, stop pin 82 reaches the distal end face of the curved surface. The contact between the distal face of surface 84 and stop pin 82 prevents further closing of the trigger.

Figure 20:
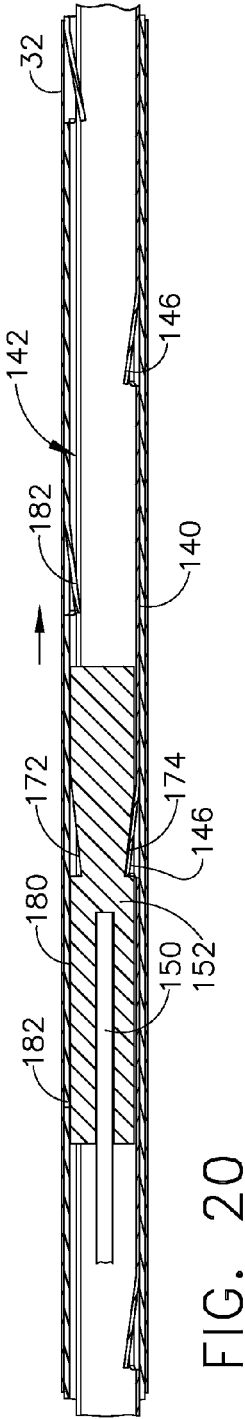
FIG. 20 is a simplified, sectional view of the fastener retainer, similar to FIG. 17, showing the outer shaft retracting proximally following release of the trigger.

After trigger 30 has been fully squeezed, and feedback provided of the T-Tag anchor deployment, the trigger is released, causing trigger return spring 74 to pivot the trigger about pin 64 back to the initial, open position. As trigger 30 pivots open, deploying pin 80 contacts the proximal force transferring leg 202. The contact between deploying pin 80 and leg 202, as well as the force within compressed springs 204, drives force transferring member 190 and outer shaft 180 back proximally to their initial, retracted positions. As outer shaft 180 retracts, cutout 182 on the shaft is bent out of engagement with pushrod driver notch 172 by the proximal taper of the notch. As outer shaft 180 retracts proximally, as shown in FIG. 20, pushrod driver 152 remains fixed in an advanced position due to the interaction between driver notch 174 and cutout 146 on the stationary inner tube 140. When outer shaft 180 returns to its initial position, notch 172 again engages a shaft cutout 182. The cutout 182, which springs into notch 172, is one cutout position distal of the previously engaged shaft cutout, due to pushrod driver 152 being held stationary by the contact between driver notch 174 and inner tube cutout 146 as the outer shaft retracts around the driver. Pushrod driver 152 is, therefore, held in a forward position in contact with the proximal end of the T-Tag anchor stack, as outer shaft 180 returns to an initial, pre-fired position. With each squeeze of trigger 30, pushrod driver 152 is moved forward one index of cutouts 146, 182 so that pushrod 150 moves forward through the needle lumen, and remains in contact with the T-Tag anchor stack. After the initial T-Tag anchor is deployed, button 54 is advanced distally to draw sheath 32 back over the tip of needle 90. With the needle tip covered, the distal end of sheath 32 may be used to probe the cavity wall to determine the location for the second fastener anchor 126. After the location is determined, button 54 is again retracted to expose the tip of needle 90, and handle 22 is manually pushed forward to penetrate the targeted tissue area with the needle tip in preparation for deploying the second T-Tag anchor.

To deploy the second T-Tag anchor of the fastener, trigger 30 is again manually squeezed to pivot the trigger about pin 64. As the trigger pivots, deploying pin 80 again contacts the distal leg of force transferring member 190 to drive the member and, correspondingly, outer shaft 180 distally within outer sheath 32. As outer shaft 180 moves forward, the shaft again advances pushrod driver 152 within inner tube 140, due to the interaction between the cutout 182 on the shaft and notch 172 of the driver. As pushrod driver 152 moves distally, pushrod 150 applies force against the proximal end of the T-Tag anchor stack to drive the stack forward towards the open distal tip of needle 90. Again, the distance that outer shaft 180 and, therefore, pushrod 150 moves forward during a full trigger stroke corresponds to the length of a T-Tag anchor within the needle lumen. Therefore, during the second trigger stroke, pushrod 150 advances a distance to expel the second T-Tag anchor 126 from needle 90. As the stack of fasteners is advanced within needle 90 during each T-Tag anchor deployment, portions of the encircled suture lengths 134, held within retention sections 214, are drawn distally into inner tube 140. Openings 216 enable the individual suture strands to move smoothly from each retention section into the inner tube without entangling with the other strands.

As the second T-Tag anchor 126 of the fastener is deployed, force transferring member 190 once again reaches the distal end of cartridge housing 34, and trigger stop pin 82 hits against the distal end of curved surface 84, stopping further movement of the trigger and providing feedback of the T-Tag anchor deployment. As pushrod 150 advances a sufficient distance to expel the T-Tag anchor 126, notch 174 on pushrod driver 152 moves into alignment with the next distally forward inner tube cutout 146. The cutout 146 springs inward into the pushrod notch 174, with the distal face of the cutout engaging the normally extending face of the notch. With the feedback of the T-Tag anchor deployment, trigger 30 is released, allowing force transferring member 190 and outer shaft 180 to again retract proximally into the cartridge. As outer shaft 180 retracts, the shaft moves relative to the fixed pushrod driver 152, to allow the next distally spaced cutout 182 to move proximally into engagement with driver notch 172. When the cutout 182 springs into notch 172, the fastener retainer is again reset to deploy the next T-Tag anchor in the stack with the next actuation of trigger 30.

After the fastener (i.e. pair of T-Tag anchors 120, 126) has been deployed, the suture attached to the fastener is cinched to oppose the surrounding tissue. To cinch the suture, the pull tab 220 associated with the deployed fastener is selected from the plurality of pull tabs extending out the proximal end of cartridge 24. A proximal pulling force is applied to the pull tab to draw the tab away from the back of the cartridge. As the tab 220 is pulled away from the cartridge, the suture attached to the tab is drawn out of the suture retention section 214, through openings 216, and out of the cartridge. After the reserved length of suture 134 is pulled from the retention section 214, tension continues to be applied to tab 220 to draw the suture taut between the fastener and the pull tab. As tension continues on the suture length 134, suture length 124 is pulled through suture knot 130 to bring the T-Tag anchors 120, 126 together. As the T-Tag anchors are brought together, the tissue surrounding the anchors is opposed. In the case of a reduction gastroplasty procedure, this apposition of tissue results in the involution of the cavity wall between the anchors.

After the T-Tag anchors are cinched together, suture length 134 is severed to separate the deployed fastener from device 20. A cutting means, such as a sharpened notch, can be provided at the distal end of outer sheath 32 for severing the suture. Following cinching, sheath 32 may be advanced distally over the fastener retainer, and the suture extending from the deployed fastener looped through the cutting means. A grasper may be used to assist in drawing the suture into the cutting means. With the suture inside the cutting means, handle 22 can be pulled proximally with a firm motion to tension the suture against a sharpened edge to sever the suture. In addition to a cutting means on sheath 32, other alternative devices and methods known to those skilled in the art may also be used for severing the suture following cinching of the T-Tag anchors without departing from the scope of the invention.

Following cinching of the initial fastener, the sheathed tip of needle 90 may be used to probe for additional fastener locations. When these fastener locations are determined, needle 90 is inserted into the tissue, and trigger 30 is squeezed to advance outer shaft 180, pushrod driver 152, and pushrod 150 to deploy an anchor from the stack in the needle lumen. Following each anchor deployment, trigger 30 is released, allowing deploying pin 80 to contact the proximal transferring member leg 202, to retract the transferring member 190 and outer shaft 180 back to their initial positions under the force of springs 204. With each T-Tag anchor deployment, pushrod driver 152 is indexed one set of cutouts 146 within inner tube 140, so that pushrod 150 remains in contact with the proximal end of the T-Tag anchor stack. Following deployment of each pair of T-Tag anchors, the suture length 134 extending from the anchors can be tensioned to cinch the anchors together. The pull tab 220 connected to the suture length of the deployed fastener is selected from the tabs at the back of cartridge 24, and the tab is drawn away from the cartridge to pull the suture slack from suture compartment 210. As the suture slack is removed from the suture compartment, tension forms in the suture to pull the T-Tag anchors and surrounding tissue together.

After the final fastener is deployed from fastener retainer 36, cartridge 24 may be removed from handle 22 and replaced with a different cartridge to enable additional fasteners to be deployed during the procedure. Cartridge 24 can be removed from handle 22 by pulling proximally on the cartridge housing 34 to dislodge step 44 from notch 48, and enable rib 40 to slide out of the mating handle groove 46. After the used cartridge is removed, a new cartridge can be attached to the handle in the manner described above. With cartridge 24 attached to the proximal end of handle 22, the cartridge can be removed from the handle without the need to remove outer sheath 32 from the trocar, thus allowing easy replacement of a cartridge during a surgical procedure with minimal interruption of the procedure.

Figure 21:
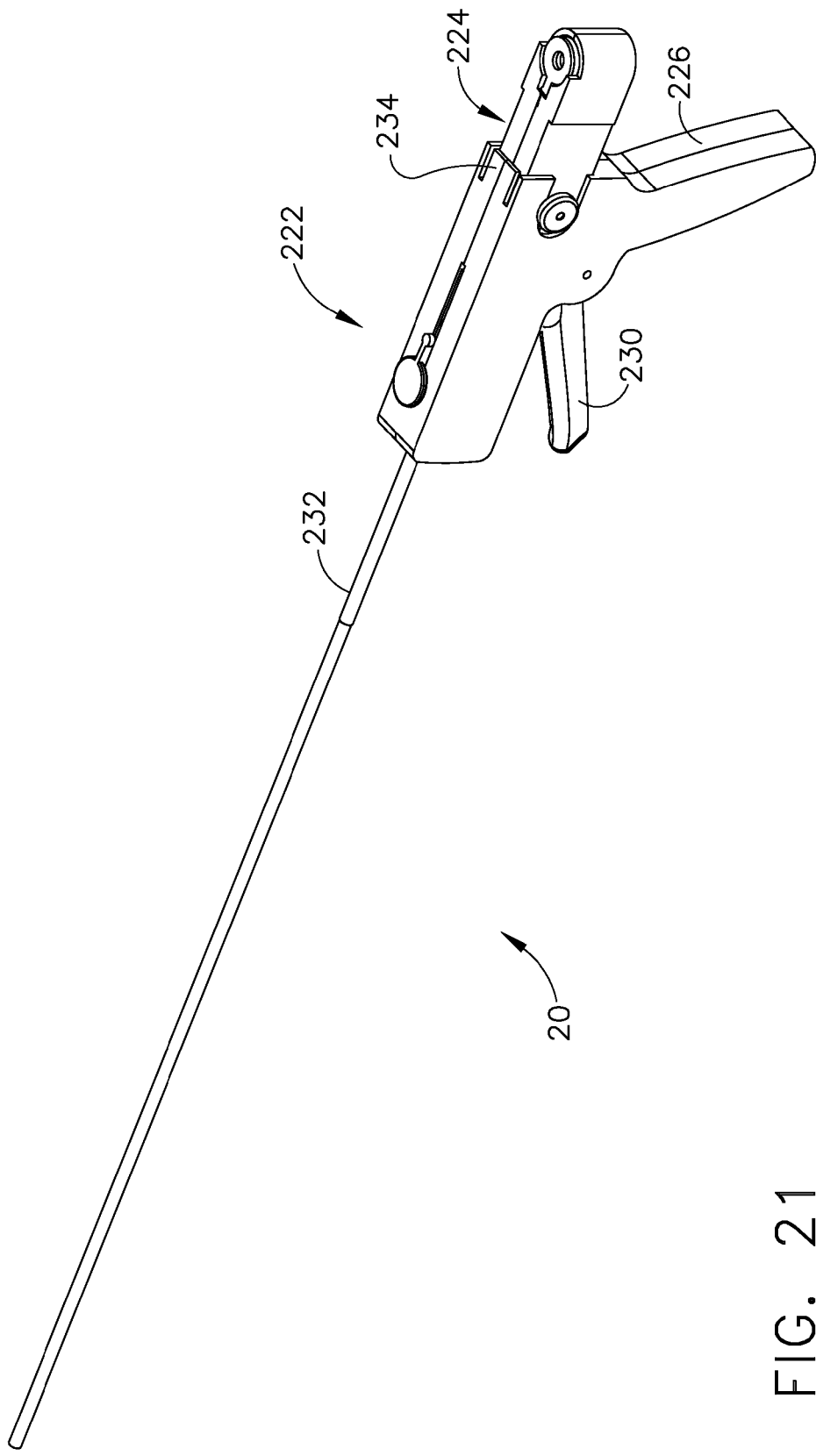
FIG. 21 is a perspective view of a second embodiment for a fastener deploying device with a replaceable cartridge.
Figure 22:
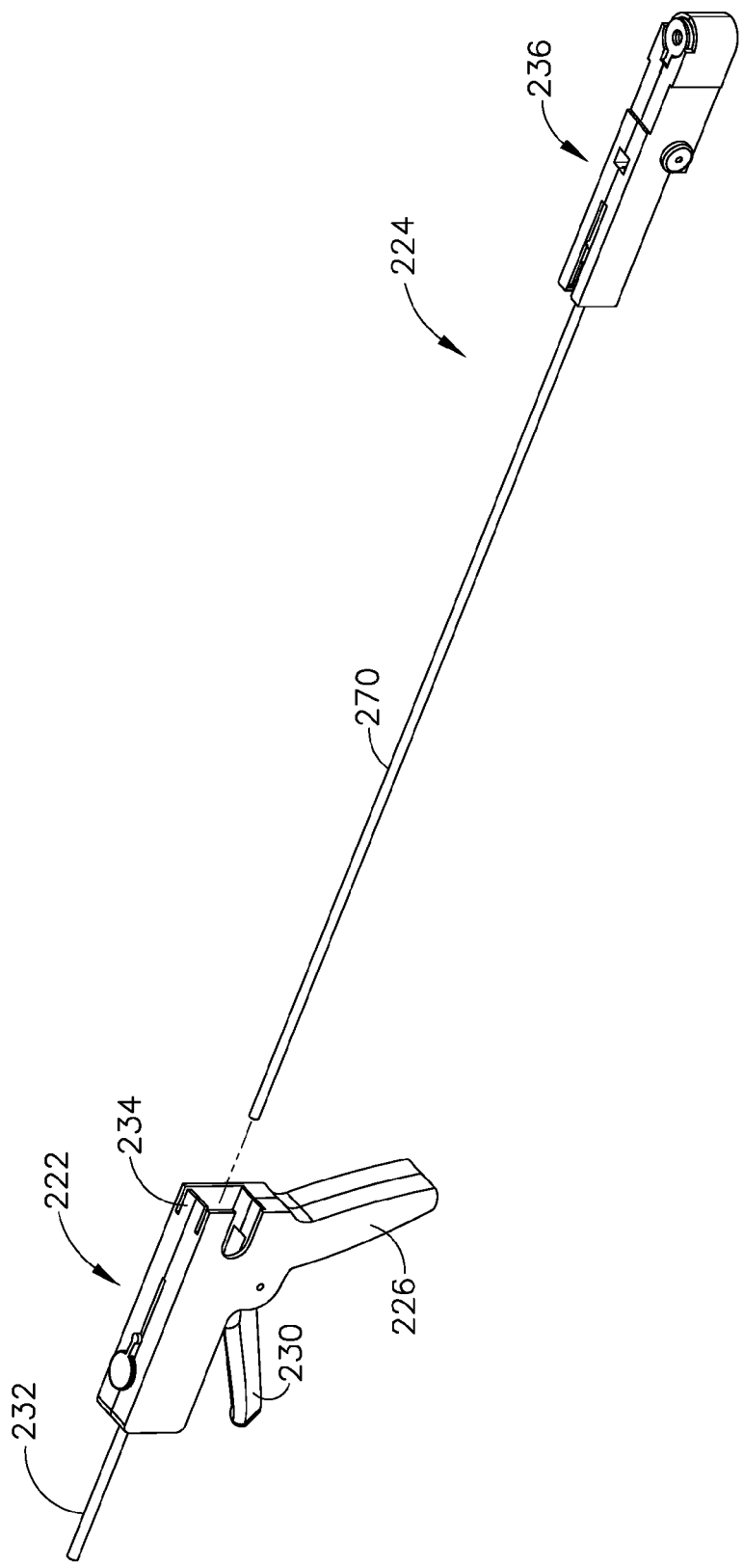
FIG. 22 is a perspective view of the device shown in FIG. 21, showing the cartridge aligned for attachment to the handle.
Figure 23:
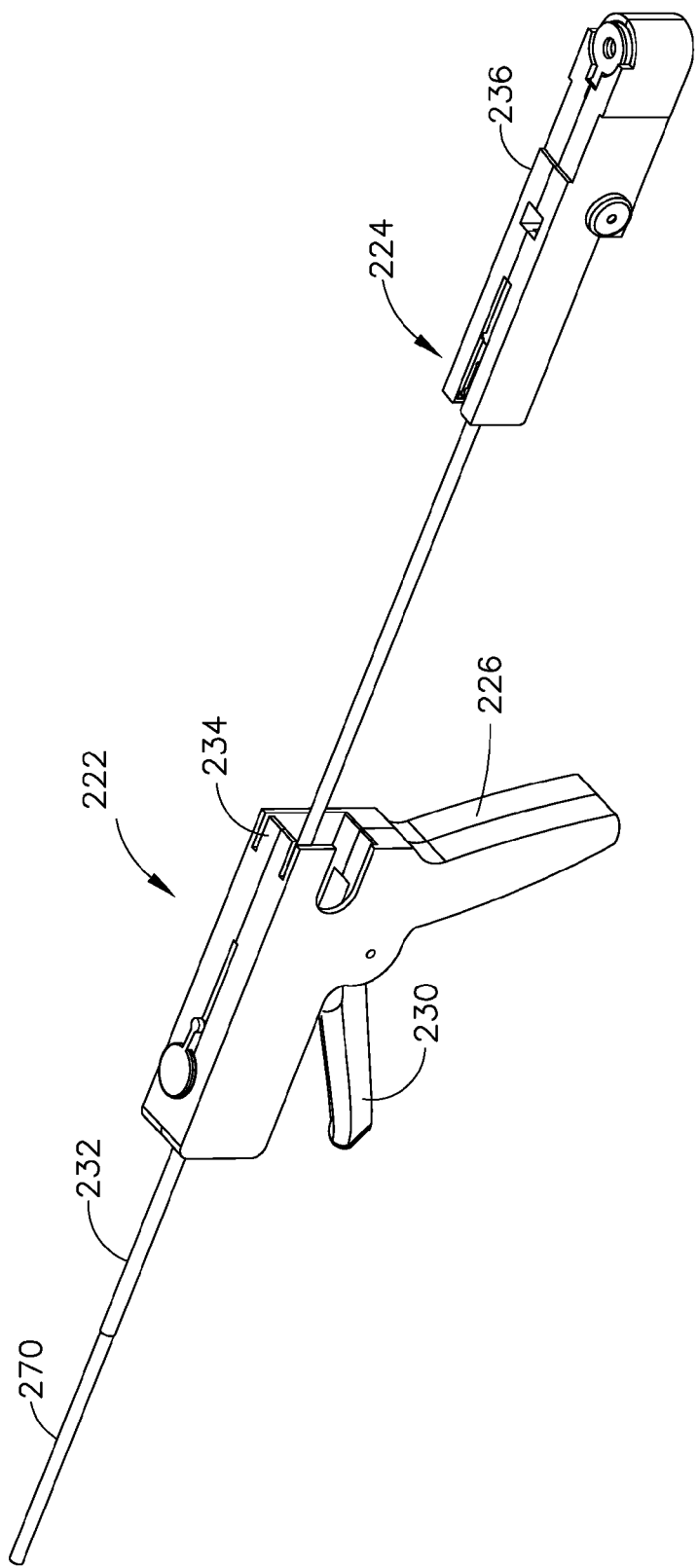
FIG. 23 is a perspective view of the device shown in FIG. 21, showing the cartridge being inserted into the handle.

Turning now to FIG. 21, which depicts a second embodiment for a fastener deploying device of the present invention. In the second embodiment, the fastener deploying device comprises a handle 222 and a removable cartridge 224. FIG. 21 shows the cartridge attached to the handle, while FIGS. 22 and 23 show the handle and fastener cartridge separated, with the cartridge aligned with and being inserted into the handle. Handle 222 includes a pistol grip 226 and an actuating member, such as a manually moveable trigger 230. A small diameter outer tube 232 extends from the distal end of handle 222. Outer tube 232 is optimally sized to allow for passage through a small (3-5 mm) diameter trocar, although specific applications may allow for or require larger sizes. Tube 232 seals the opening between the trocar and handle, and keeps the handle engaged within the trocar during removal and replacement of a cartridge.

The proximal end of handle 222 is open for receiving and retaining a cartridge 224. Coupling members can be provided on the handle and cartridge for releasably attaching the cartridge within the open proximal end of the handle. The coupling members preferably allow for a rapid and secure removal and replacement of a cartridge. In the exemplary embodiment shown in the figures, the coupling members comprise a deflectable catch 234 adjacent the proximal open end of the handle. Deflectable catch 234 snaps down onto a stepped edge 236 of cartridge 224, after the cartridge is loaded into handle 222, in order to lock the cartridge onto the handle.

Figure 24:
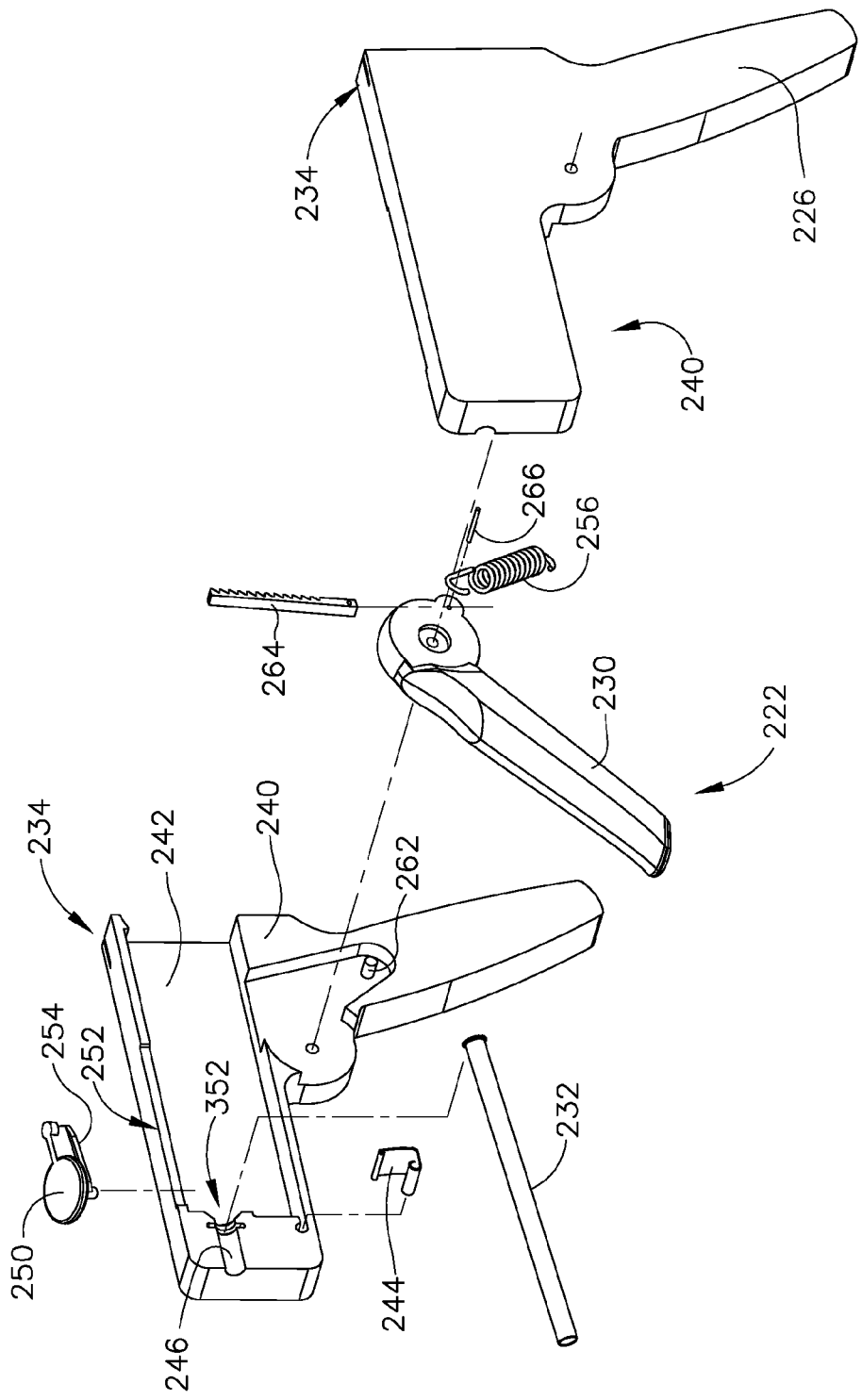
FIG. 24 is an exploded view of the handle of the deployment device.

As shown in FIG. 24, handle 222 comprises a housing 240 formed in sections which are joined together during the manufacturing process by any of a number of suitable means known in the art. The interior of handle housing 240 is substantially hollow to form a cavity 242 (only one side is shown in the figure) for receiving and holding a cartridge 224. A spring clip 244 is located at the distal end of cavity 242 for biasing a retained cartridge proximally against deflectable catch 234, in order to prevent relative movement of the cartridge within the handle housing. A channel 246 is formed into housing 240, distal of cartridge cavity 242, for retaining tube 232. The proximal end of tube 232 has a ring of enlarged diameter which is retained within a slot formed at the proximal end of channel 246, in order to fix the tube in position within the handle. A button 250 is mounted on the top of handle 222 to slide within a track 252 formed into the outer surface of the housing. Button 250 includes a connecting piece 254 that extends beneath the button and into cartridge cavity 242.

As mentioned above, handle 222 includes a manually operable trigger 230 for expelling fasteners from an attached cartridge. Trigger 230 pivots about a pin (not shown) that extends between the sides of handle housing 240 and through one end of the trigger. When the grip of trigger 230 is squeezed, the trigger pivots about the pin to rotate the end of the trigger in a distal direction within the housing. A return spring 256 is attached to trigger 230 by a pin 266 extending between the sides of housing 240. The second end of return spring 256 is attached to housing 240 by a post 262. Return spring 256 biases trigger 230 into an open, unsqueezed position. A rack 264, having a plurality of proximally facing teeth, is also attached to trigger 230 by pin 266. Pin 266 extends through a first end of rack 264 and trigger 230 adjacent to the trigger pivot pin. When trigger 230 is squeezed, the trigger rotates about the pivot pin, driving rack 264 upward within cartridge cavity 242.

Figure 25:
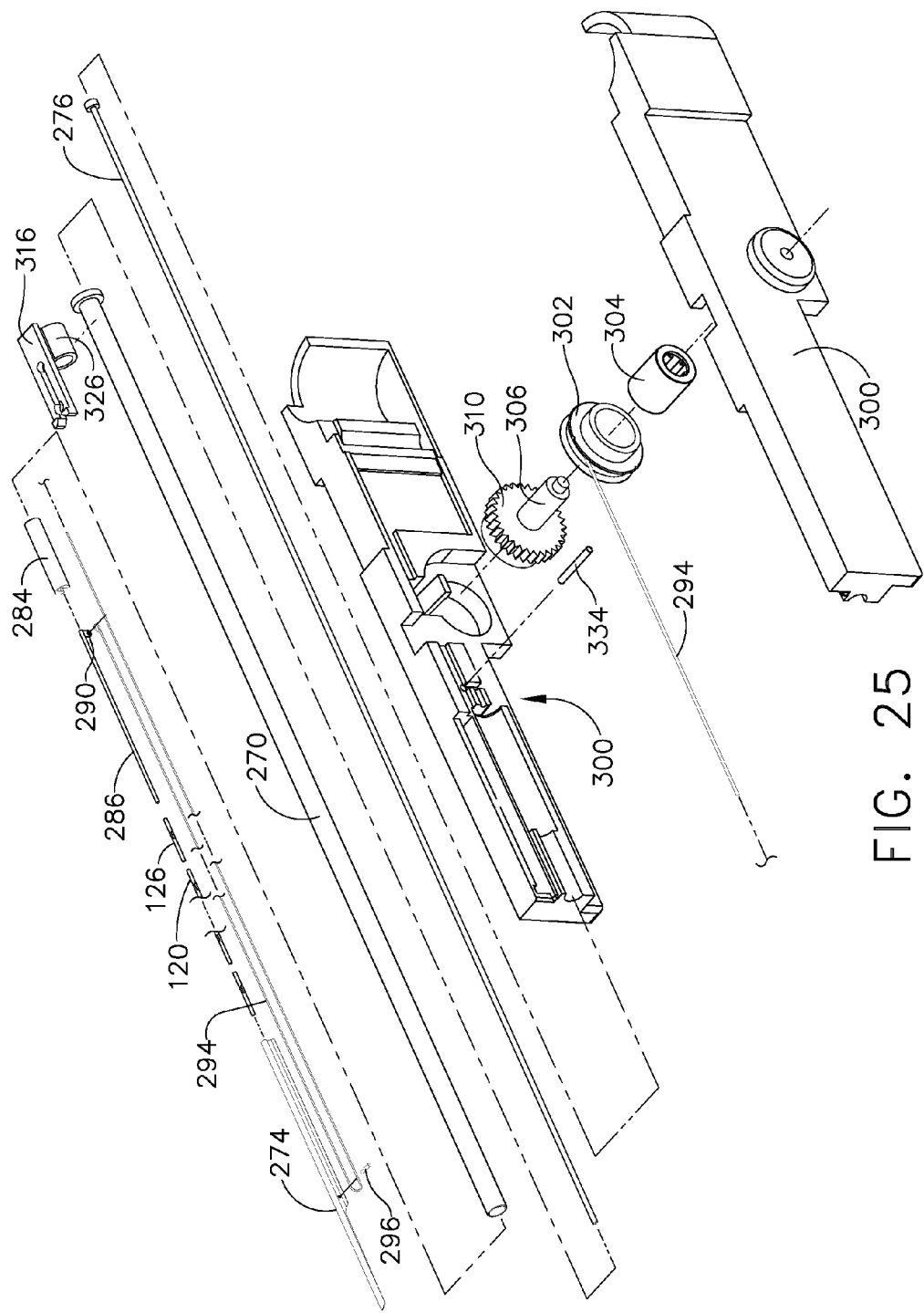
FIG. 25 is an exploded view of the cartridge of the deployment device.
Figure 26:
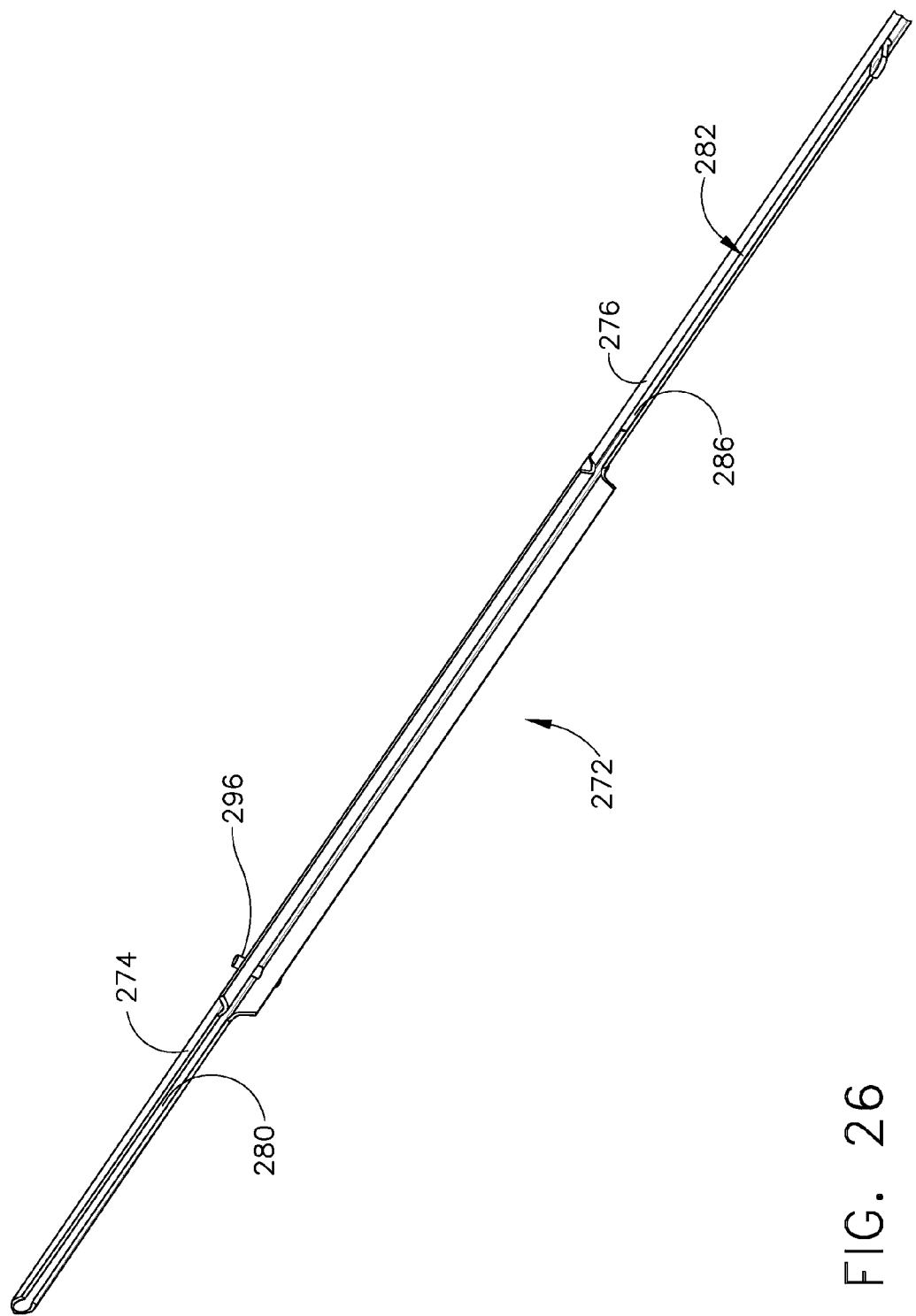
FIG. 26 is a perspective view of an exemplary needle.

As shown in greater detail in FIG. 25, cartridge 224 includes an elongated, distally extending protective sheath 270. As in the previous embodiment, sheath 270 is sized for passage through a small diameter trocar port, and has sufficient length to enable use within an obese patient at numerous trocar access sites. Sheath 270 is also sized for passage through outer tube 232. Housed within sheath 270 is an elongated needle 272 (shown in greater detail in FIG. 26) comprising a tissue penetrating member or piercer 274 and a fastener retaining shaft 276. Tissue piercer 274 includes a sharpened distal tip and an axially-extending lumen. Piercer 274 can have a number of different shapes and configurations, similar to those described in the previous embodiment, and can likewise be formed by any of the previously described methods. Similar features preventing unintentional release of fasteners components may also be incorporated into these needle embodiments. An axially-extending slot 280 extends through the wall of piercer 274, along the length of the piercer, to provide an opening into the lumen. The proximal end of piercer 274 abuts the distal end of fastener retaining shaft 276. Fastener retaining shaft 276 also extends into cartridge housing 300. The proximal end of shaft 276 is affixed to the cartridge housing so that the shaft is stationary during fastener deployment. Shaft 276 includes an axially extending lumen which is aligned with the lumen in piercer 274, and an axially extending slot 282 that is circumferentially aligned with the slot in piercer 274. Specific features (e.g., lead-ins), guides in sheath 270, and/or mates between piercer 274 and fastener retaining shaft 276 may be used to ensure alignment between lumens and slots allowing for smooth passage of fasteners and elongated fastener driver 286 between and through the fastener retaining shaft lumen and the piercer lumen.

Figure 27:
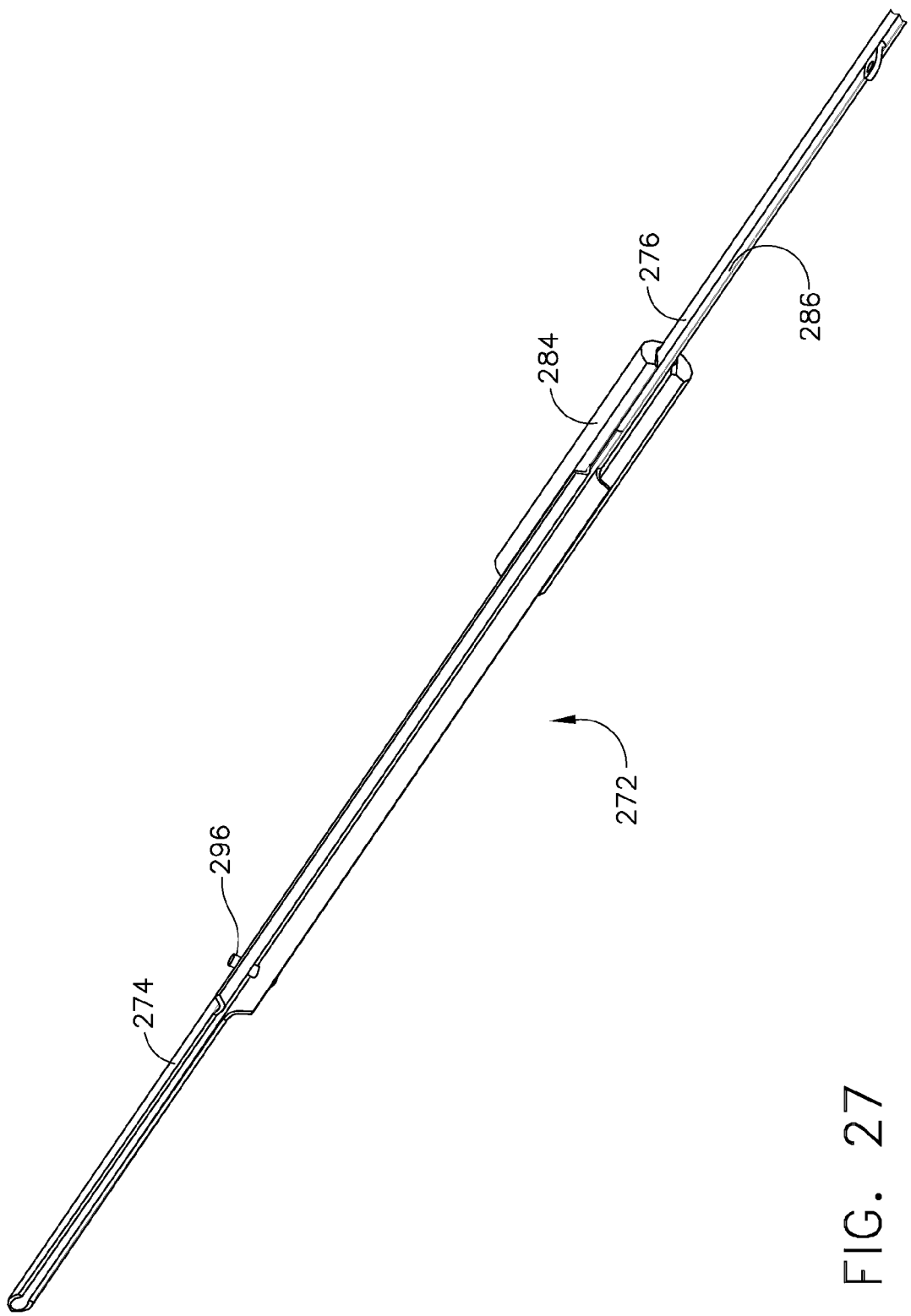
FIG. 27 is a perspective view of an exemplary needle, similar to FIG. 26, showing the guide partially surrounding the needle at the junction between the piercer and fastener retaining shaft.

One example of an alignment means is shown in FIG. 27. In this embodiment a guide 284 partially surrounds the abutting junction between piercer 274 and shaft 276. Guide 284 assists in aligning the lumens and slots in the piercer and shaft, to form a continuous needle lumen therethrough for the passage of fasteners. As described in the previous embodiment, the cartridge needle at least partially retains and deploys one or more tissue fasteners, such as, for example, pairs of pre-tied T-Tag anchors. A plurality of the pre-tied anchor pairs are loaded into the needle lumen, such that the first "looped" T-Tag anchor deploys initially, followed by the second "attached" T-Tag anchor, although the order may be reversed. The anchor pairs are stacked one against another within the needle lumen, and each anchor is positioned so that the suture from the anchor passes normal to the anchor axis through the needle slot.

Figure 28:
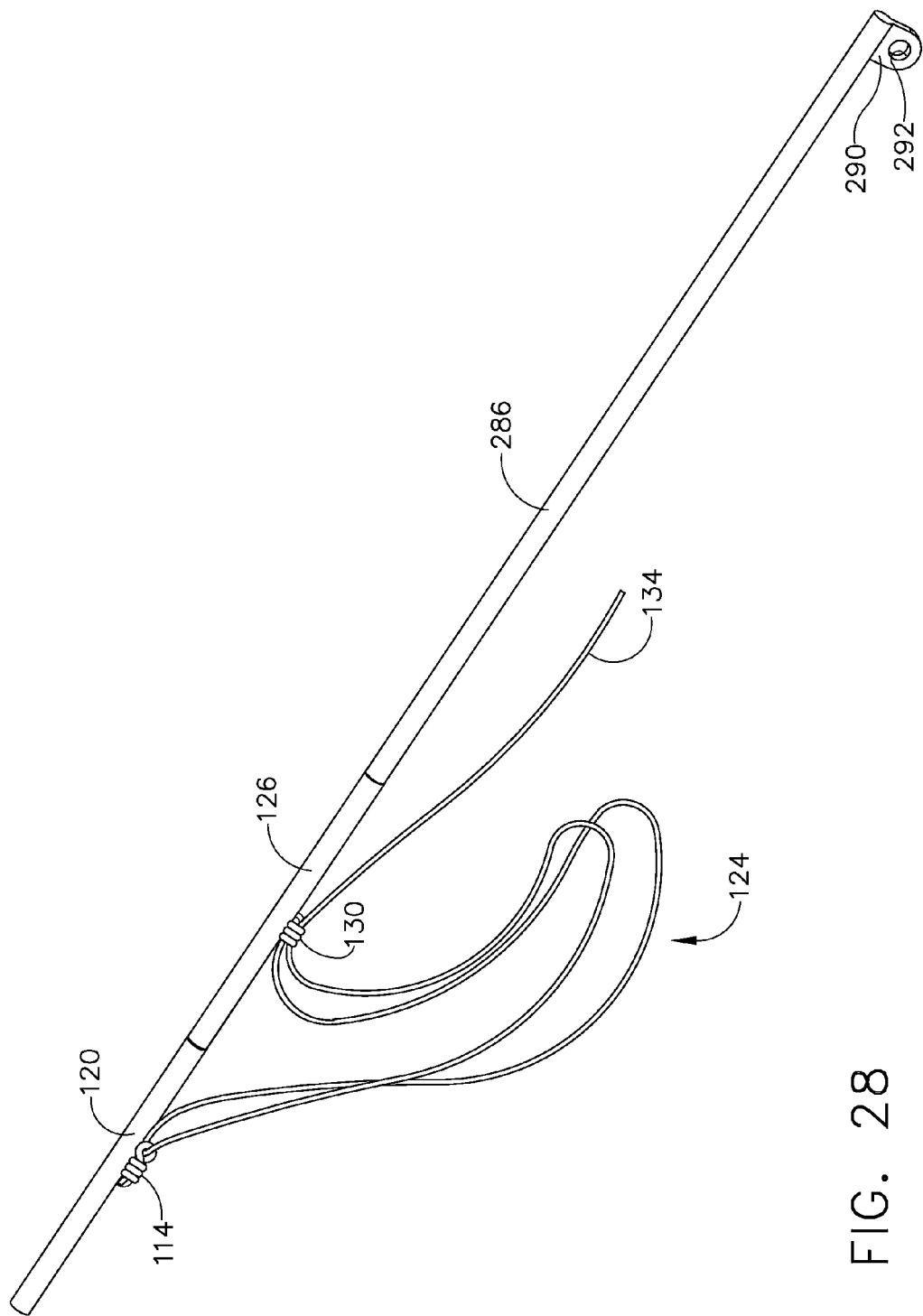
FIG. 28 is a perspective view showing the fastener driver in isolation, abutting a pair of T-Tag anchors.
Figure 30:
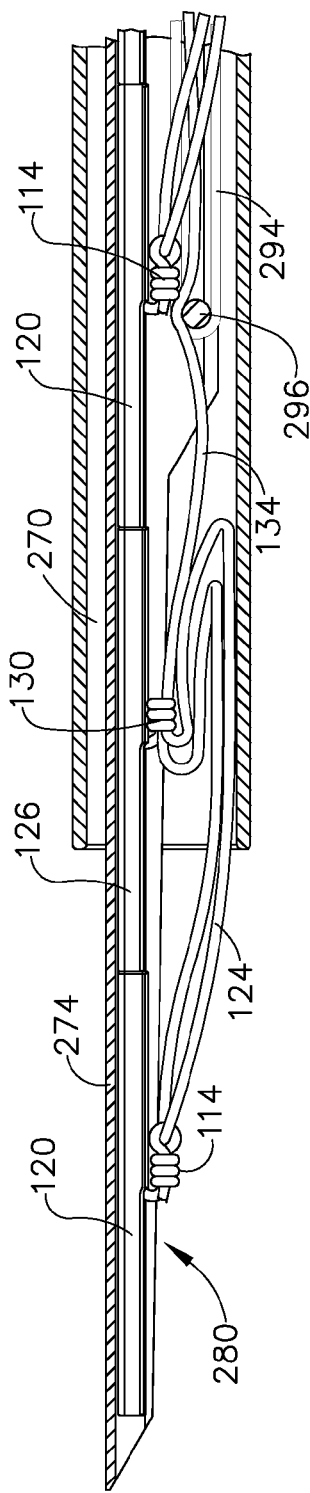
FIG. 30 is a sectional view of the distal end of the fastener deploying device, showing the needle containing a plurality of T-Tag anchors stacked for deployment.
Figure 29:
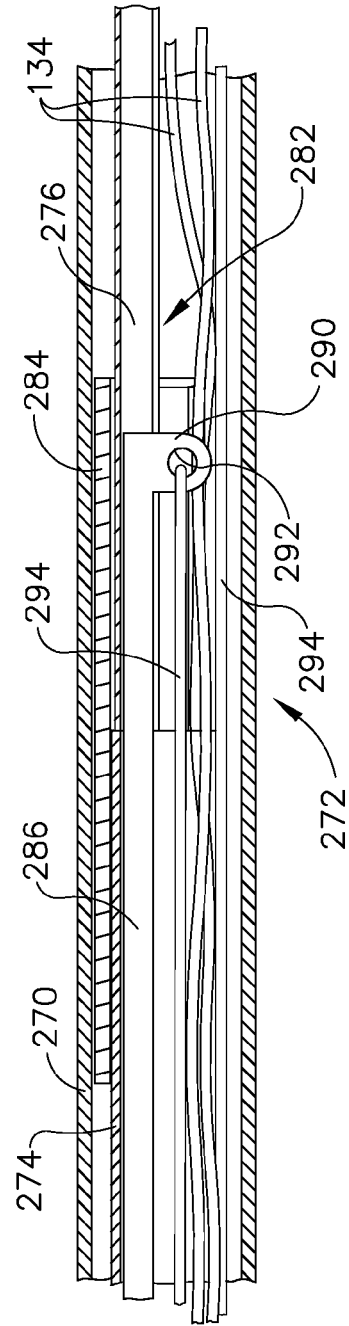
FIG. 29 is a sectional view of the sheath, needle and fastener driver, showing the connection between the cable and fastener driver in greater detail.

An elongated fastener driver 286 extends longitudinally within the needle lumen. The distal end of fastener driver 286 abuts the proximal end of the T-Tag anchor stack in the needle lumen for advancing and expelling the anchors from the needle. The alignment between fastener driver 286 and a pair of T-Tag anchors 120, 126 is shown in greater detail in FIG. 28. A tab 290 having a hole 292 therethrough is located at the proximal end of fastener driver 286. Tab 290 extends normal to the axis of driver 286 and through slot 282 in shaft 276. As shown in FIGS. 25 and 29, a driving cable 294 is attached at one end to tab 290. Cable 294 is attached to tab 290 by forming a loop in the cable end that passes through tab hole 292. A pin 296 passes through piercer 274 in a direction perpendicular to the piercer axis. As shown in FIG. 30, cable 294 extends distally from tab 290, through protective sheath 270 and piercer 274, and wraps around the distal side of pin 296. After looping around pin 296, cable 294 is routed back proximally through sheath 270 and into a cartridge housing 300. Within housing 300, the second end of cable 294 is connected to a cable retracting mechanism, as shown in FIG. 25. A knot or other size enhancing member can be formed or placed in the second end of cable 294 for securing the cable to a winding member in the retracting mechanism, such as, for example, a spool 302 as shown. Cable 294 passes from fastener driver 286 distally around pin 296 and then back proximally to spool 302 in order to form a pulley for advancing fastener driver 286 distally within the needle lumen as the driving cable is pulled proximally by winding onto the spool. Materials for pin 296 and cable 294 are optimally selected and paired to minimize sliding friction between them. Surface treatments or other material coating methods may also be applied to pin 296 and cable 294 to minimize this friction.

Figure 31:
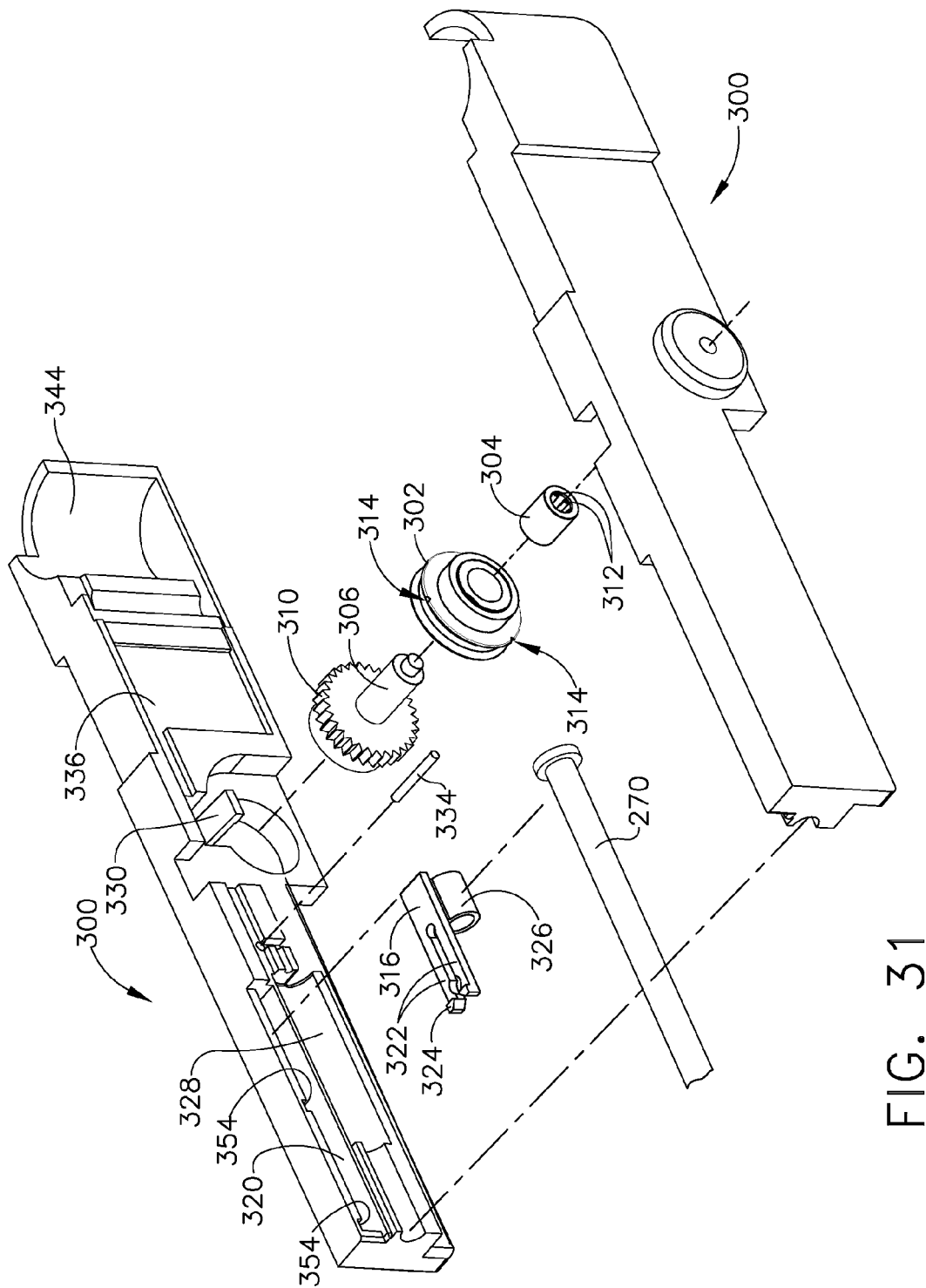
FIG. 31 is an exploded view of the cartridge housing showing the cable retracting mechanism in greater detail.

Within the cartridge, spool 302 is connected to a clutch 304, shown in FIG. 31. A post 306 extends between the sides of cartridge housing 300 and through the center of spool 302 and clutch 304. A gear 310 is attached to post 306 for rotating the post and, in turn, spool 302. Unidirectional rollers 312 are located in the bore of clutch 304 to control the rotation of post 306 and, thus, spool 302. A plurality of notches 314 are spaced about the outer circumference of spool 302. The arc-length (along the radius of the spool where cable 294 is wound) between each of the spool notches 314 ideally corresponds to the length of each of the T-Tag anchors 120, 126 stacked within the needle lumen. Alternatively, the arc-length between notches 314 is chosen so that the distance between more than one set of notches corresponds to the length of each of the T-Tag anchors 120, 126. Cartridge 224 also includes a button latch 316 that rides within a track 320 formed into cartridge housing 300. Latch 316 includes a pair of distally-extending, spaced legs 322, having tabs 324 that extend upwardly from the distal tips of the legs. A cylindrical connecting member 326 extends beneath latch 316 into a cavity 328. The proximal end of sheath 270 extends into cartridge housing 300, and through connecting member 326, to attach the sheath to button latch 316. Numerous means for attaching cylindrical connecting member 326 to sheath 270 may be used including but not limited to press-fits, adhesives, locking features within both components, set screws, etc. Sheath 270 reciprocates within cavity 328 in response to movement of button 250.

Figure 32:
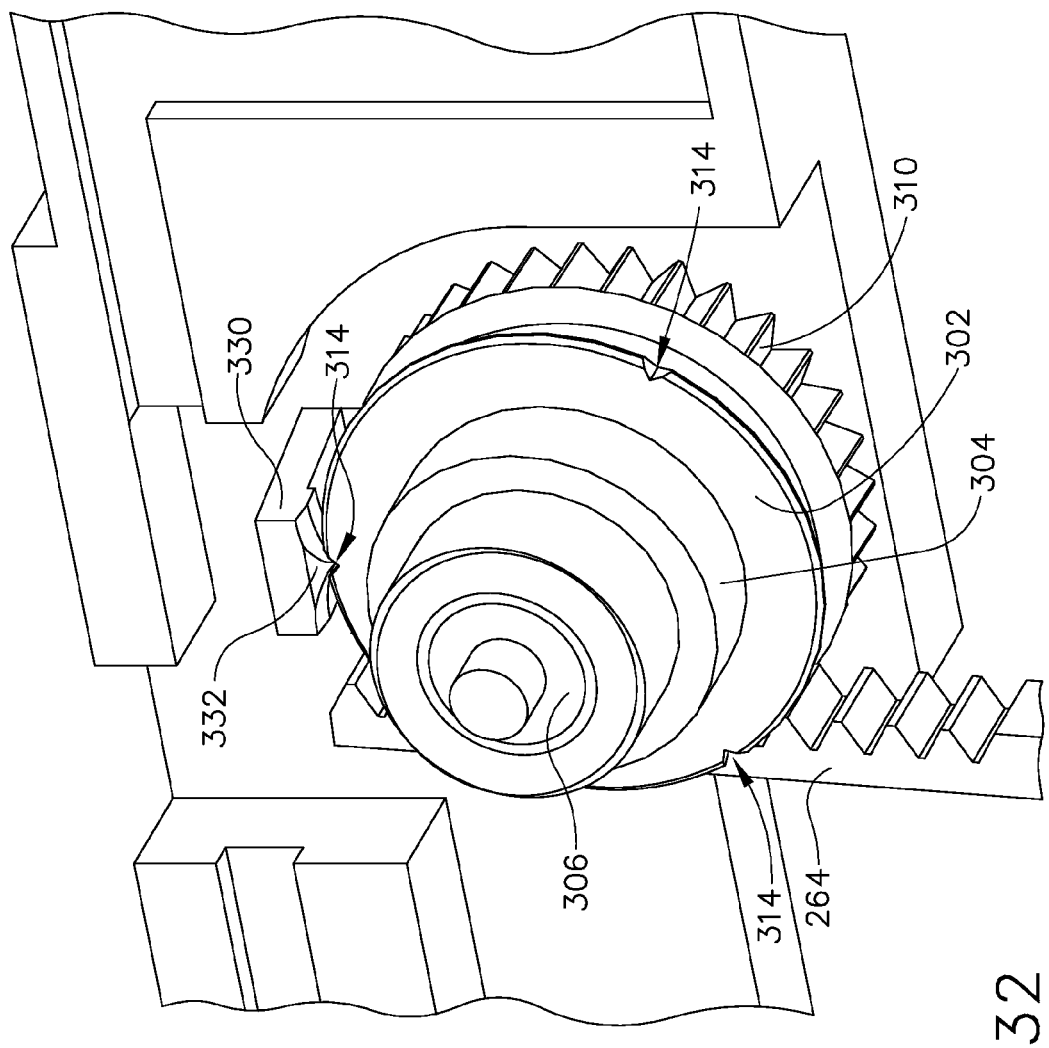
FIG. 32 is an isolated, perspective view of the cable retracting mechanism showing the catch engaging a notch on the spool.

As shown in FIGS. 31 and 32, an arm 330 extends outward from cartridge housing 300 over gear 310 and spool 302. The outer end of arm 330 includes a catch 332, which is shaped to engage the notches 314 on the outer rim of spool 302. Catch 332 engages a notch 314 following deployment of each T-Tag anchor, in order to prevent backward revolution of spool 302 as trigger 230 is released and returned to an initial, open position.

Figure 33:
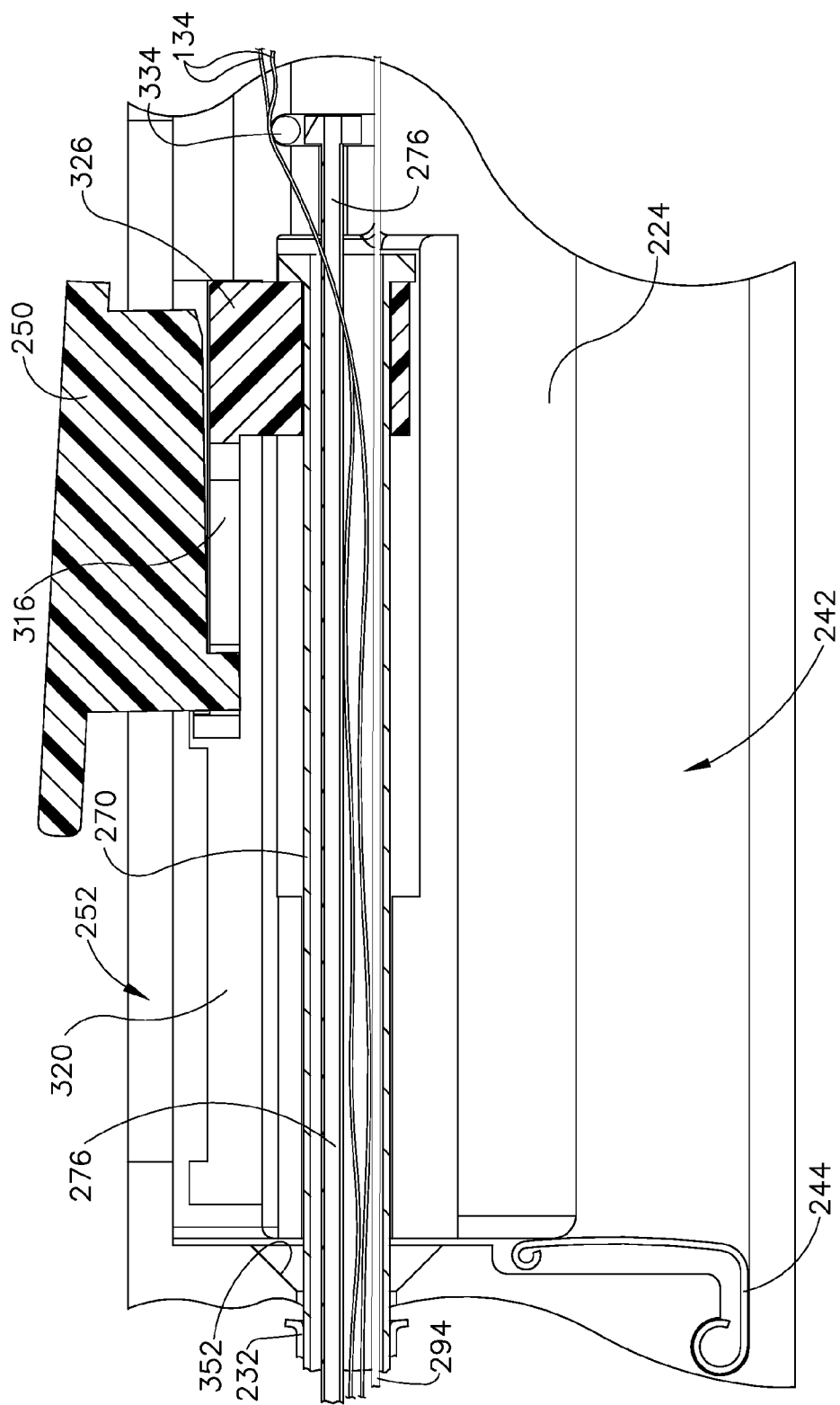
FIG. 33 is a sectional view showing the distal end of the cartridge housing loaded within the handle, and the button in a proximal position to retract the sheath back from the distal tip of the needle.
Figure 34:
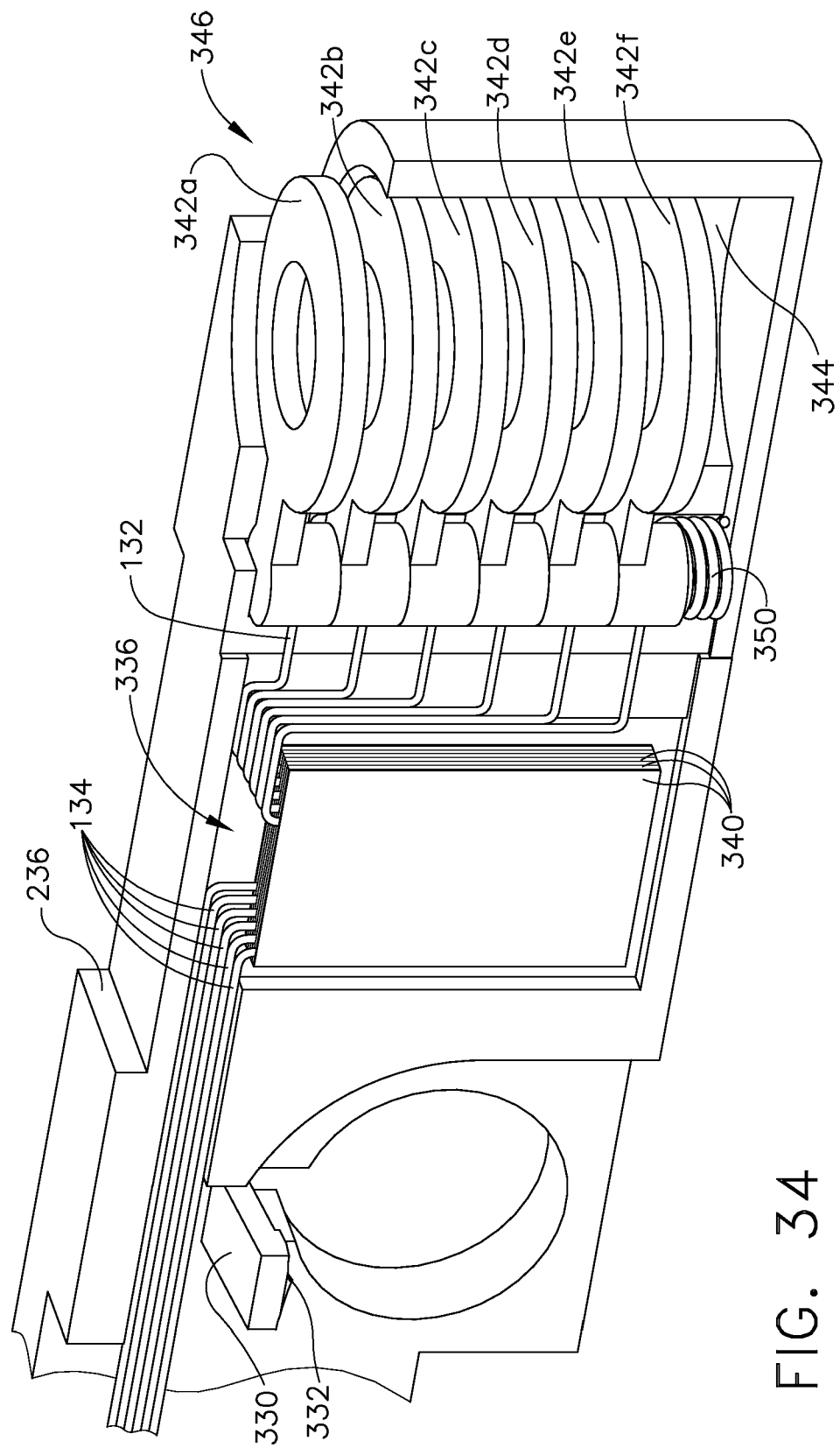
FIG. 34 is a perspective view of the distal end of the cartridge, showing the suture retention compartment and pull tabs.
Figure 35:
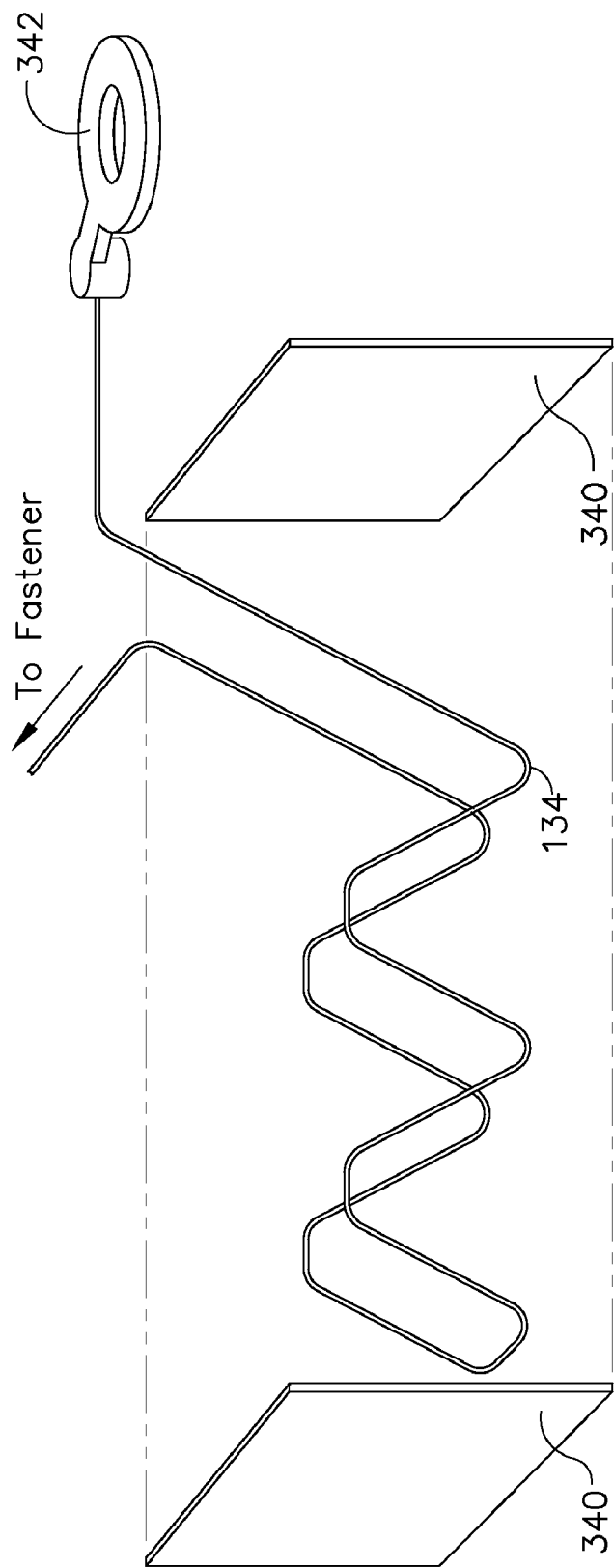
FIG. 35 is a diagrammatic view showing placement of a suture strand between separators prior to placement in the retention compartment.

The suture lengths from the T-Tag anchors stacked in needle 272 (indicated by the two strands 134 shown in FIG. 33) extend proximally through protective sheath 270 and into cartridge housing 300. Within housing 300, the reserved lengths of suture pass out the end of sheath 270, and proximally to a suture retention compartment. One or more suture deflecting pins 334 may be provided within cartridge housing 300 for defining a suture pathway within the housing. Within the suture retention compartment, identified by reference numeral 336 in FIG. 34, the individual suture lengths 134 are encircled upon themselves between pairs of separators 340. Separators 340 comprise thin sheets formed from any of a variety of materials, such as, for example, paper, plastics or metals. Separators 340 enable the suture lengths to be separately stored, and then subsequently individually released from compartment 336, as the attached fastener is deployed and cinched during a procedure. Using separators 340 enables the suture lengths to be individually stored and retrieved from within a compact area of the cartridge, while preventing tangling between the strands. As shown in FIG. 35, each of the suture lengths 134 may be accordion folded between a pair of separators 340. The separators can then be stacked one on top of the other within retention compartment 336.

Figure 36:
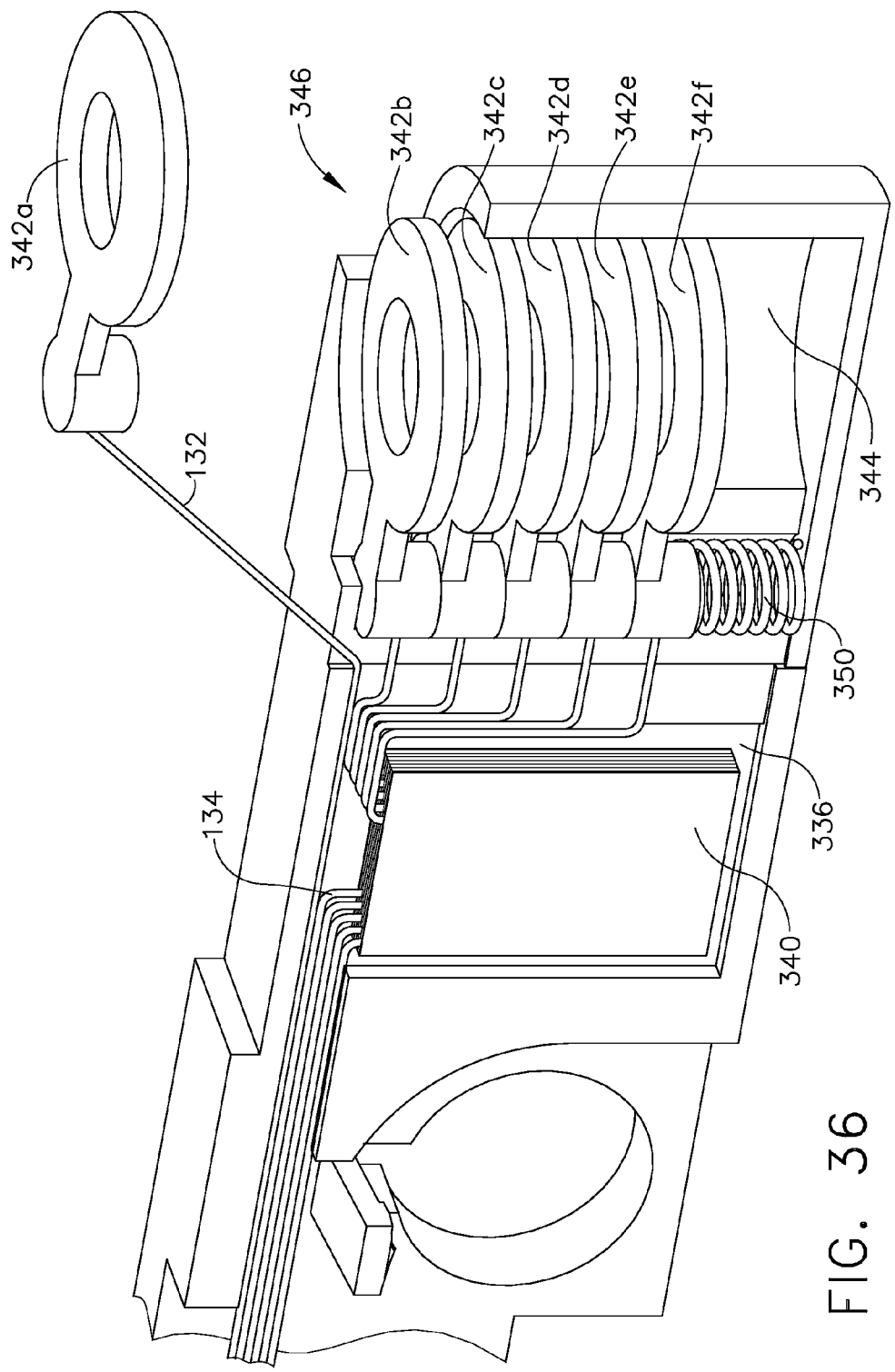
FIG. 36 is a perspective view similar to FIG. 34, showing a pull tab being removed from the cartridge.

Outside of compartment 336, the loose end 132 of each suture length is attached to a fastener identifying member, such as a pull tab 342. As described above, each of the pull tabs (individually labeled in FIGS. 34 and 36 as 342a-342f) corresponds to one of the fasteners stacked within the needle lumen. Pull tabs 342 are stacked within a pull tab section 344 at the proximal end of cartridge 224 according to the position of the attached fastener within the needle lumen. Consequently, the top-most pull tab in the stack, 342a, corresponds to the distal-most fastener (i.e. pair of T-Tag anchors) in the needle; the second pull tab 342b in the stack corresponds to the second distal-most fastener in the needle, and so forth. An opening 346 is provided in pull tab section 344 for accessing the tabs. Pull tabs 342 are biased upward in the direction of the opening by a spring 350. As a pull tab is removed from the top of the stack through opening 346, as shown in FIG. 36, the suture length 134 attached to the pull tab is drawn from between the separators 340 and out of the suture compartment 336. After the top-most pull tab is removed from section 344, the remaining pull tabs are advanced in the direction of opening 346 by spring 350, to position the next pull tab at the opening. In the example shown in FIGS. 34 and 36, six pull tabs are stacked within pull tab section 344. The number of pull tabs provided in pull tab section 344 will vary, however, depending upon the number of fasteners stacked within the needle, since there is a one-to-one correspondence between the fasteners and pull tabs.

Figure 37:
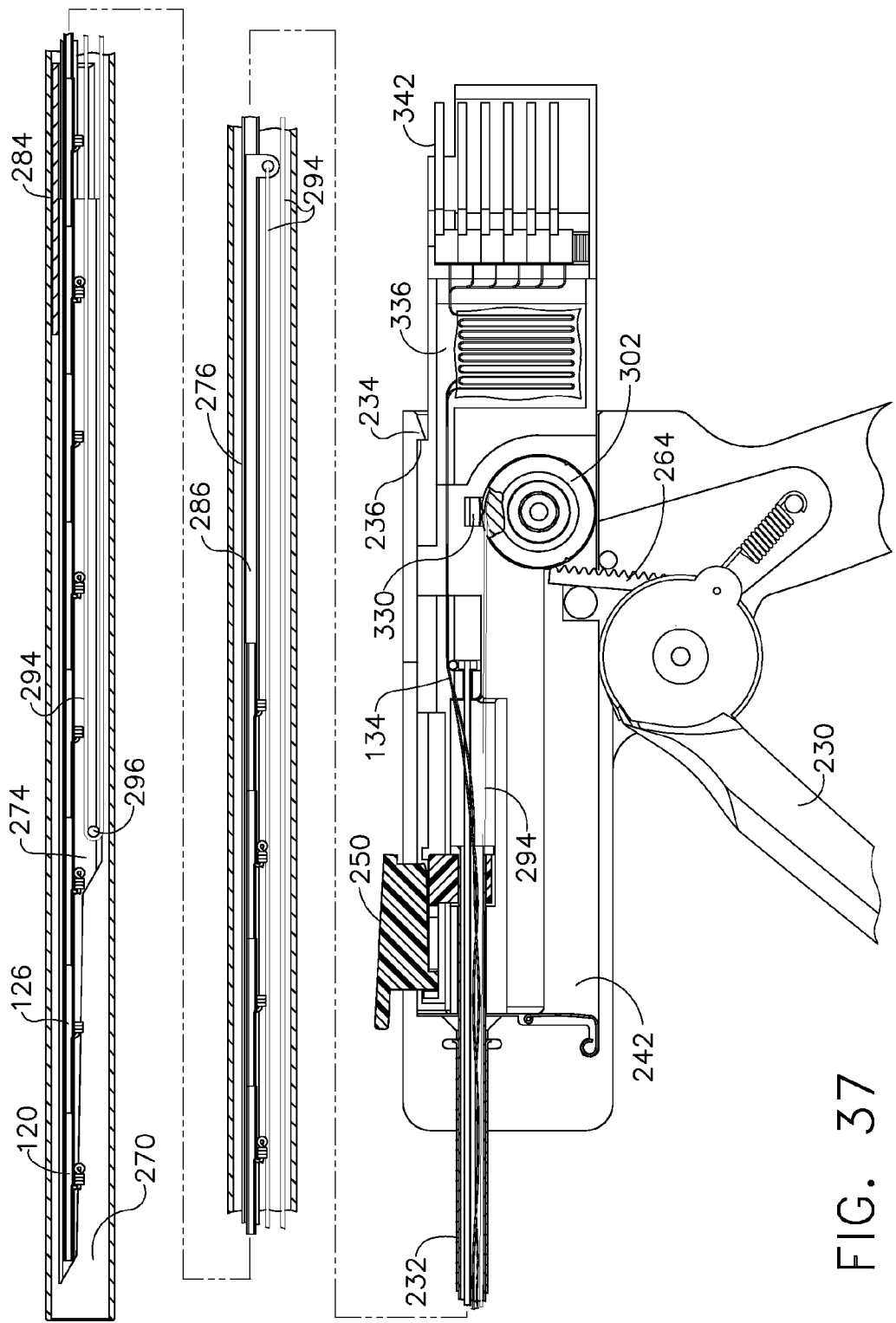
FIG. 37 is a side, sectional view of the fastener deploying device prior to deployment of a fastener.

To load a cartridge 224 onto handle 222, the distal end of protective sheath 270 is inserted through the opening at the proximal end of handle housing 240, and into and through outer tube 232, as shown in FIG. 23. Sheath 270 is longer than outer tube 232, to allow the sheath to protrude beyond the distal opening of the tube. Sheath 270 may be substantially longer than outer tube 232 to address user interface requirements. However, outer tube 232 may also be of a similar length to sheath 270 to provide additional stiffness to the system. In all cases, the distal end of outer tube 232 should not interfere with the ability to expose a desired length of piercer 274. The opening between cartridge cavity 242 and tube 232 may be angled, or funneled, as indicated by reference numeral 352 in FIG. 24, to facilitate the insertion of sheath 270 into the tube. With sheath 270 inside tube 232, cartridge 224 is advanced distally within cartridge cavity 242 until catch 234 snaps down onto stepped edge 236 of cartridge housing 300, and the distal end of the cartridge housing contacts spring clip 244. As cartridge 224 is inserted into cavity 242, button latch 316 is advanced distally towards button connecting piece 254. Spaced latching legs 322 engage opposing sides of connecting piece 254 as the cartridge is fully inserted, to attach button 250 to latch 316. Likewise, as cartridge 224 is inserted into the hollow interior of handle 222, the unattached tip of rack 264 projects into the cartridge through an opening in the lower surface of the cartridge housing. As cartridge 224 reaches the distal-most, locked position within handle 222, gear 310 advances distally so that the teeth on the gear interlock with the teeth on rack 264, as shown in FIG. 32. With button 250 connected to protective sheath 270 via latch 316, and the gear and rack teeth interlockingly mated, the cartridge 224 is fully loaded onto handle 222, and the device ready for fastener deployment, as shown in FIG. 37.

Figure 38:
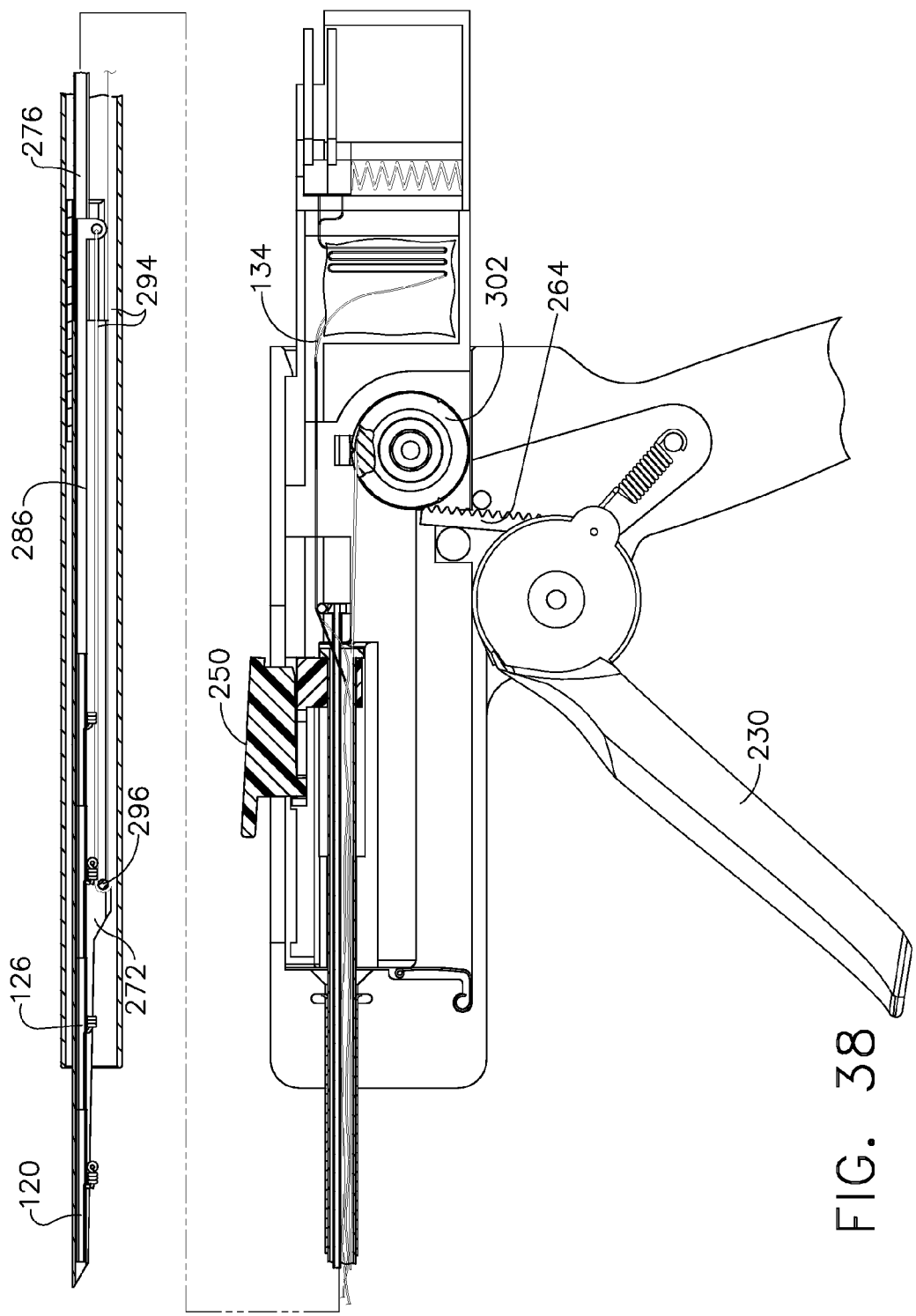
FIG. 38 is a side, sectional view of the deploying device showing the button retracted to draw the sheath proximally, exposing the distal tip of the needle.

To deploy a T-Tag anchor at a desired tissue location, button 250 is retracted proximally along the outer surface of handle 222. As button 250 retracts, the button pulls the attached latching member 316 proximally through track 320 and, in turn, protective sheath 270 proximally within cartridge channel 328. Track 320 includes a pair of axially spaced notches 354 (shown in FIG. 31) that engage latching leg tabs 324 as latch 316 is reciprocated within the track. Leg tabs 324 move between the notches in the track to lock sheath 270 in either an advanced (protective) position, (i.e. the distal notch) or a retracted, deploying position (i.e. the proximal notch). As sheath 270 moves proximally, the distal, sharpened end of piercer 274 is exposed, as shown in FIG. 38. With the tip of piercer 274 exposed, the device is ready to be inserted into body tissue.

Figure 39:
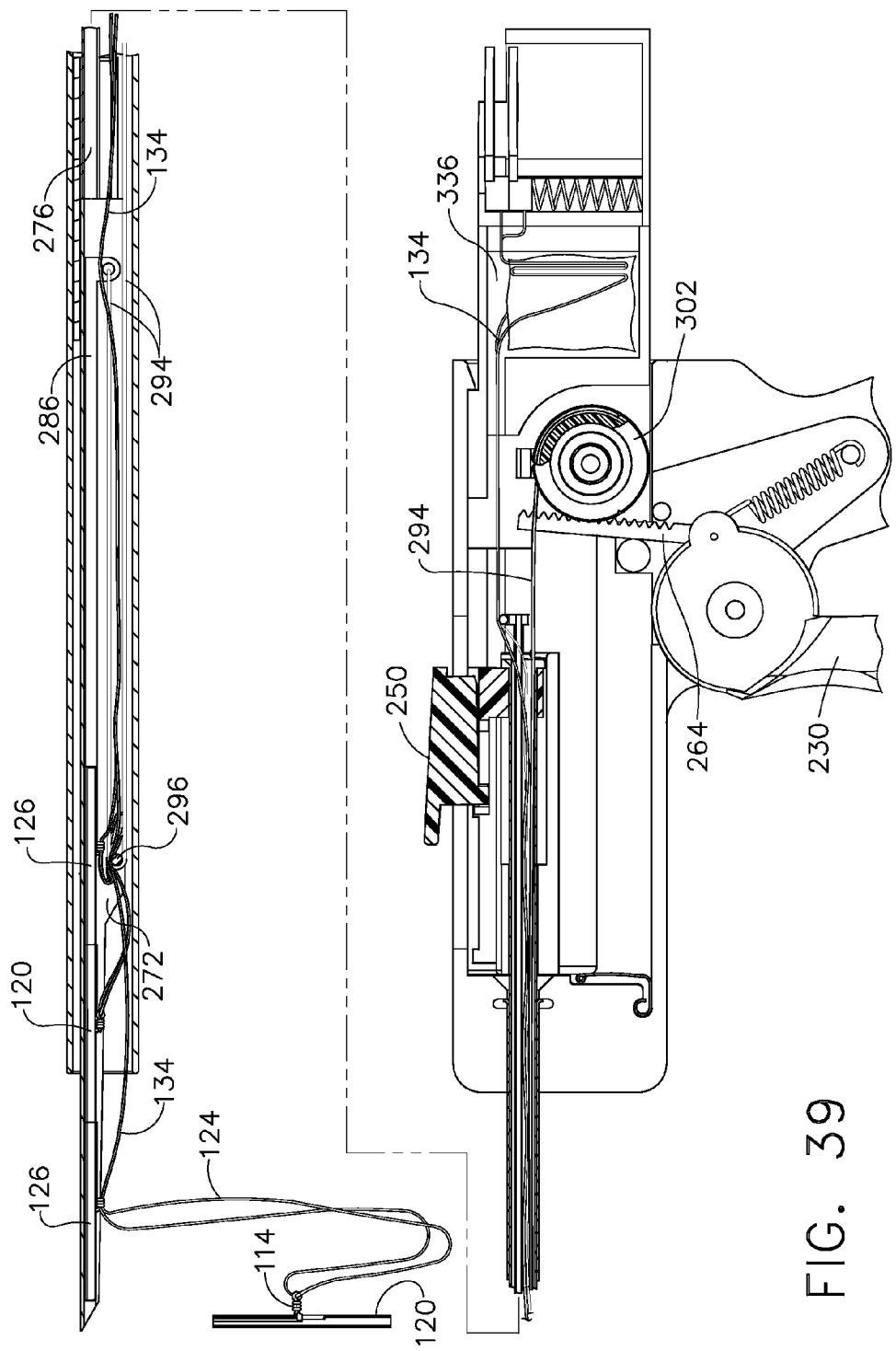
FIG. 39 is a side, sectional view of the fastener deploying device, similar to FIG. 38, showing a first T-Tag anchor deployed from the device.

After the piercer is inserted into tissue, trigger 230 is manually squeezed to deploy a T-Tag anchor from needle 272. As trigger 230 is squeezed, the pivoting action of the trigger drives rack 264 upward. As rack 264 moves upward, the interaction between the rack and gear teeth rotates gear 310. As gear 310 rotates, post 306 which is rigidly attached to gear 310 rotates as well. Post 306 is in contact with one way rollers 312 within clutch 304. The direction of the rotation of gear 310 and post 306 while trigger 230 is being squeezed is such that the one way rollers 312 do not rotate. Since clutch 304 is not permitted to rotate about post 306 due to the one-way rollers remaining stationary, clutch 304 rotates in unison with post 306 and gear 310 while trigger 230 is being squeezed. Spool 302 is rigidly attached to clutch 304. Therefore, squeezing trigger 230 results in the rotation of gear 310 which in turn rotates the attached spool 302, winding cable 294 onto the spool. As spool 302 rotates, a section of drive cable 294 corresponding in length to the length of a T-Tag anchor in needle 272 is wound onto the spool. Additionally, as spool 302 rotates, catch 332 rides along the outer circumferential rim of the spool. As trigger 230 becomes fully pivoted, catch 332 engages a notch 314 on the rim of the spool. As cable 294 is being wound onto spool 302, a pulling force is created within the cable. This pulling force is transferred distally through the cable to piercer pin 296, and around the pin proximally to fastener driver 286. The force of cable 294 on fastener driver 286 advances the driver distally against the proximal end of the T-Tag anchor stack. Fastener driver 286 pushes the anchor stack distally, thereby expelling the distal-most T-Tag anchor through the open tip of the needle, as shown in FIG. 39. As the T-Tag anchor stack is advancing distally within needle 272, the suture strands attached to the anchors are drawn out of suture retention compartment 336 and distally through the cartridge housing into sheath 270.

After a first T-Tag anchor 120 is deployed, trigger 230 is released, allowing the trigger to pivot back open under the force of return spring 256. As the trigger pivots open, rack 264 is pulled downward due to the pin connection between the trigger and the rack. The downward movement of rack 264 in turn rotates gear 310, due to the interlocking teeth between the gear and rack. This direction of rotation for gear 310 and post 306 is not coupled to the motion of the spool 302 as one way rollers 312 can freely roll in this direction. Therefore, the interaction between catch 332 and a notch 314 on spool 302, as well as the one way rollers within clutch 304, prevents spool 302 from rotating in a reverse direction along with gear 310. Thus, spool 302 is held stationary as trigger 230 springs open, maintaining tension in cable 294 and keeping fastener driver 286 in contact with the proximal end of the T-Tag anchor stack.

Figure 40:
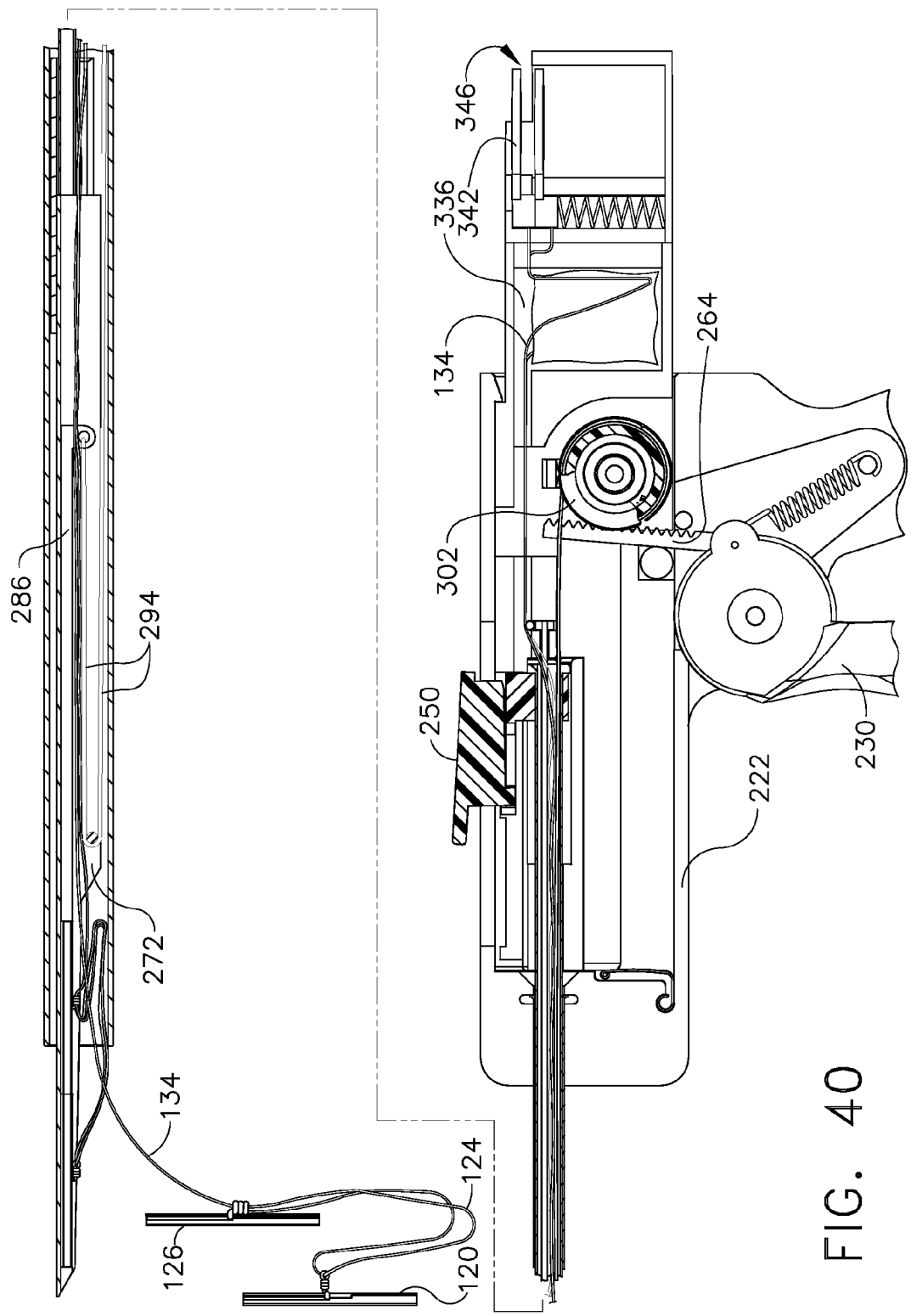
FIG. 40 is a side, sectional view of the fastener deploying device, similar to FIG. 39, showing a second T-Tag anchor deployed from the device.

Following the release of trigger 230, button 250 is advanced distally to draw sheath 270 forward over the tip of needle 272. With the needle tip concealed, the distal end of the device can be used to probe body tissue for the second T-Tag anchor location. Once the desired location is determined, button 250 is again refracted, and the exposed tip of needle 272 inserted into the tissue. With the needle inside (partial thickness deployment) or through the tissue (full thickness deployment), trigger 230 is again squeezed to drive rack 264 upward to rotate gear 310 and in turn spool 302. As spool 302 rotates, a pulling force is again created in cable 294 as the cable is wound onto the spool. This pulling force further advances fastener driver 286 against the T-Tag anchor stack, and drives the distal-most T-Tag anchor 126 through the open tip of the needle, as shown in FIG. 40. As trigger 230 is fully pivoted, spool 302 is rotated to a position in which a second one of the notches 314 is aligned with catch 332, so that the catch springs into the notch and prevents reverse rotation (and subsequent unwinding of cable 294) as the trigger returns to an open position.

Figure 41:
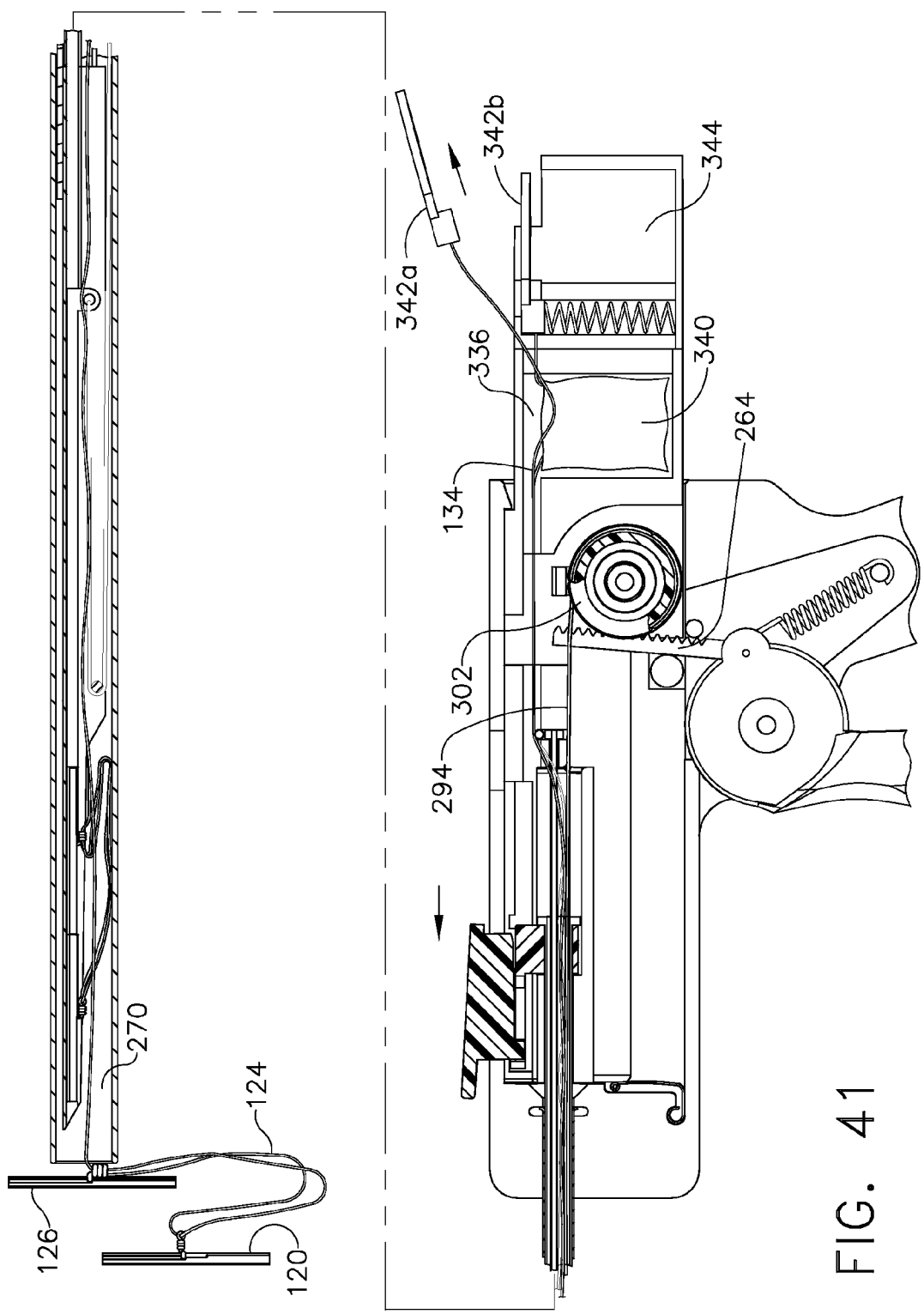
FIG. 41 is a side, sectional view of the fastener deploying device, similar to FIG. 40, showing a pull tab being withdrawn from the cartridge to tension the suture within the fastener.
Figure 42:
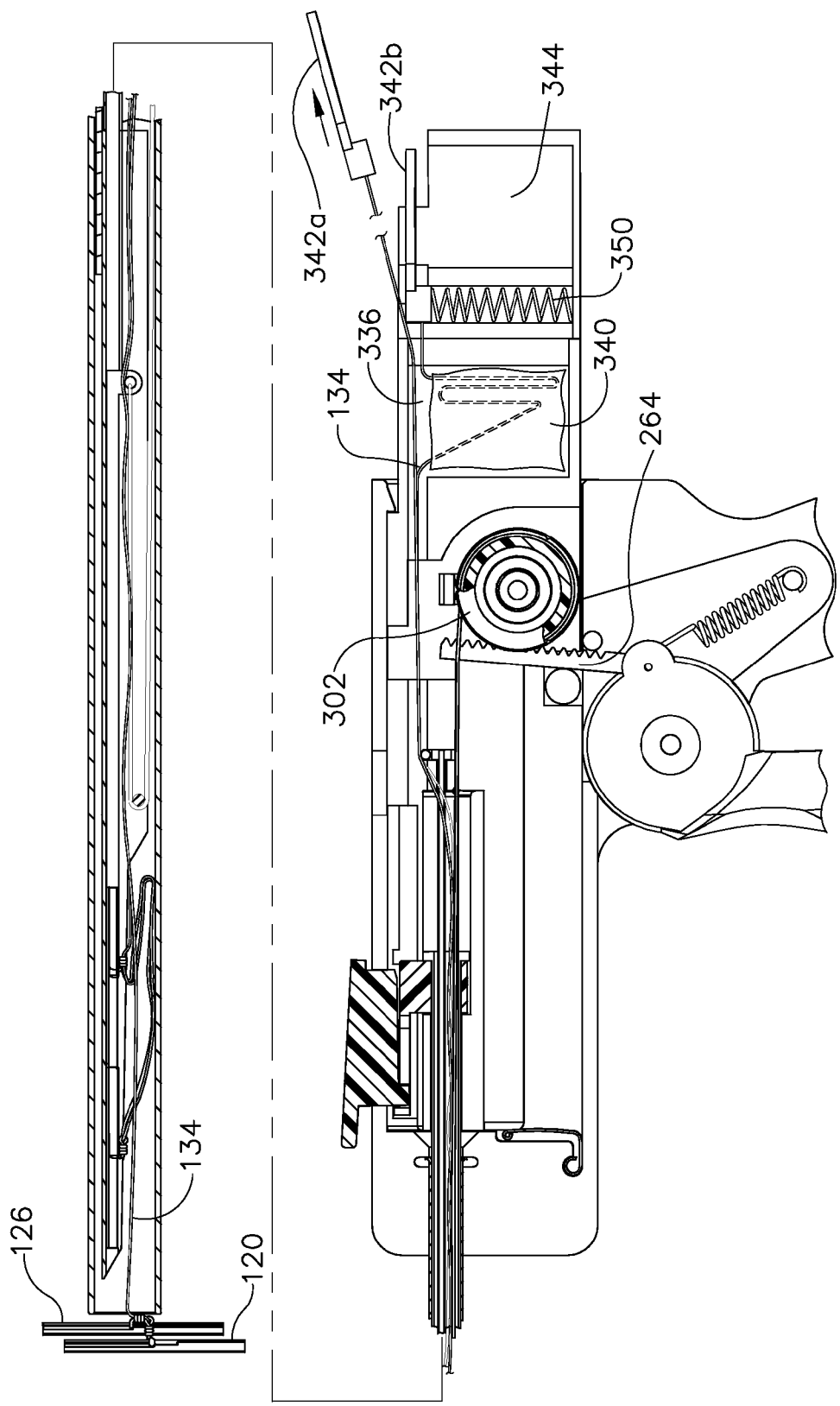
FIG. 42 is a side, sectional view of the fastener deploying device, similar to FIG. 41, showing the T-Tag anchors in the fastener cinched together.

After the second T-Tag anchor of the fastener has been deployed, button 250 is advanced to draw sheath 270 over the tip of needle 272. With the needle tip concealed, the suture attached to the deployed fastener is cinched to oppose the surrounding tissue. To cinch the suture, the pull tab 342a associated with the deployed fastener is lifted away from the top of the pull tab stack at the proximal end of cartridge 224. A proximal pulling force is applied to the pull tab to draw the tab through opening 346 and away from the back of the cartridge. As the pull tab 342a is removed from pull tab section 344, the remaining pull tabs in the stack (i.e. a single pull tab 342b is shown in FIG. 41) are pushed in the direction of opening 346 by spring 350. As the tab is pulled away from the cartridge, as shown in FIG. 41, the suture attached to the tab is drawn from between separators 340 in retention compartment 336 and out of the cartridge. After the reserved length of suture 134 is pulled from the retention compartment, tension continues to be applied to the tab 342 to draw the suture taut between the fastener and the tab. As tension continues on the suture length 134, doubled suture length 124 is pulled through suture knot 130 to bring the T-Tag anchors 120, 126 together, as shown in FIG. 42. As the T-Tag anchors are brought together, the tissue surrounding the anchors is opposed.

After the T-Tag anchors are cinched together, suture length 134 is severed, as described above, to separate the deployed fastener from the device. Following cinching and severing of the initial fastener, the sheathed needle tip may be used to probe for additional fastener locations. When these fastener locations are determined, needle 272 is inserted into or through the tissue, and trigger 230 is squeezed to rotate spool 302 and wind an additional length of cable 294. As additional cable 294 is wound onto spool 302, fastener driver 286 pushes against the T-Tag anchor stack to expel additional T-Tag anchors from the needle. With each T-Tag anchor deployment, catch 332 is indexed one notch 314 about the circumference of the spool 302. Following each anchor deployment, trigger 230 is released, pulling rack 264 back down along the side of gear 310 without unwinding spool 302, thereby enabling the fastener driver to continue advancing against the fasteners within the needle.

After the final fastener is deployed from needle 272, cartridge 224 may be removed from handle 222 and replaced with a different cartridge to enable additional fasteners to be deployed during the procedure. Cartridge 224 can be removed from handle 222 by pushing upward on handle catch 234 to deflect the catch away from stepped edge 236 of the cartridge. With catch 234 deflected out of the way, cartridge 224 can be slid out of the open proximal end of the handle. After the used cartridge is removed, a new cartridge can be attached to the handle in the manner described above. In this embodiment, as in the first embodiment, cartridge 224 is attached to the proximal end of handle 222; thereby allowing the cartridge to be released from the handle without the need to remove tube 232 from the trocar, and enabling a rapid replacement of a cartridge during a surgical procedure with minimal interruption of the procedure.

Figure 43:
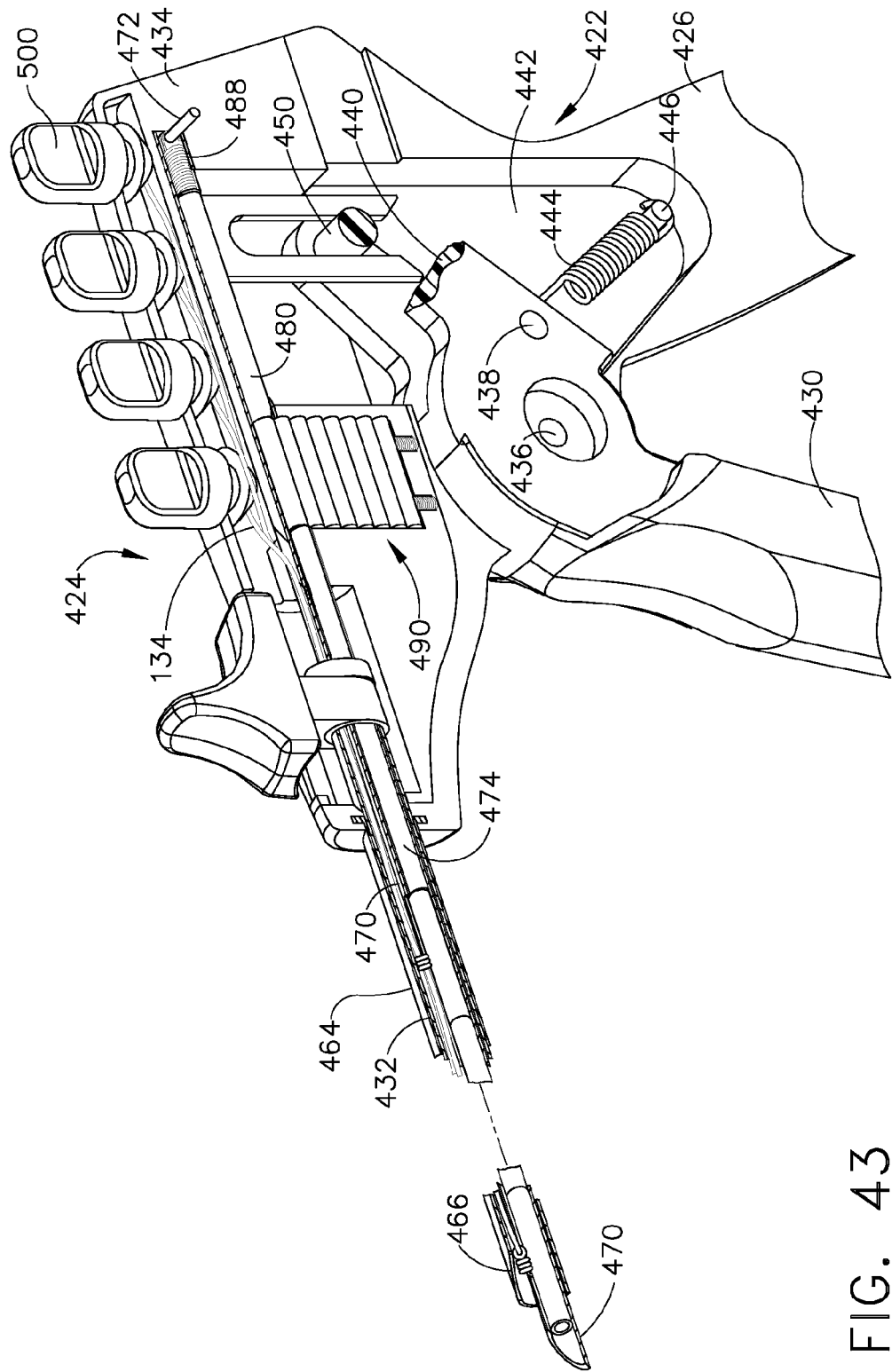
FIG. 43 is a perspective view of a third embodiment for a fastener deploying device, shown with a portion of the device removed.
Figure 44:
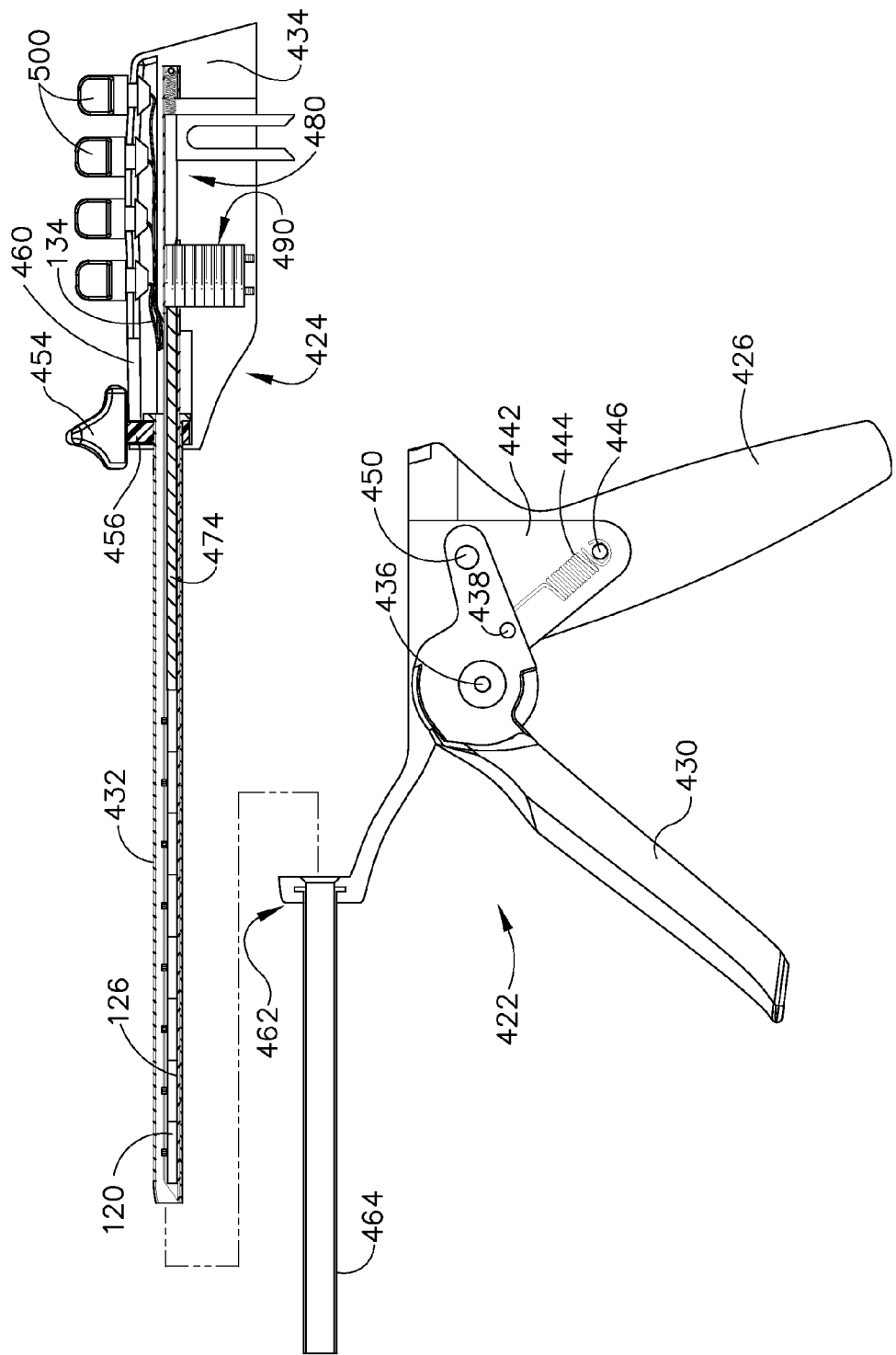
FIG. 44 is a side, sectional view of the deploying device of FIG. 43, showing the cartridge aligned for attachment to the handle.

FIG. 43 shows a third embodiment for a fastener deploying device of the present invention. As shown in FIG. 43, the device includes a handle 422 and a releasable fastener cartridge 424. As in the previous embodiments, the fastener cartridge is attachable to the proximal end of the handle. Coupling members are provided on the device for rapidly and securely removing and attaching cartridges to the handle. The coupling members can comprise any of a number of different types of apparatus, including the deflectable catch and rib/groove arrangements described in the previous embodiments. FIG. 43 shows the cartridge 424 attached to the handle 422, while FIG. 44 shows the handle and fastener cartridge separated, with the cartridge aligned for attachment to the handle.

Figure 45:
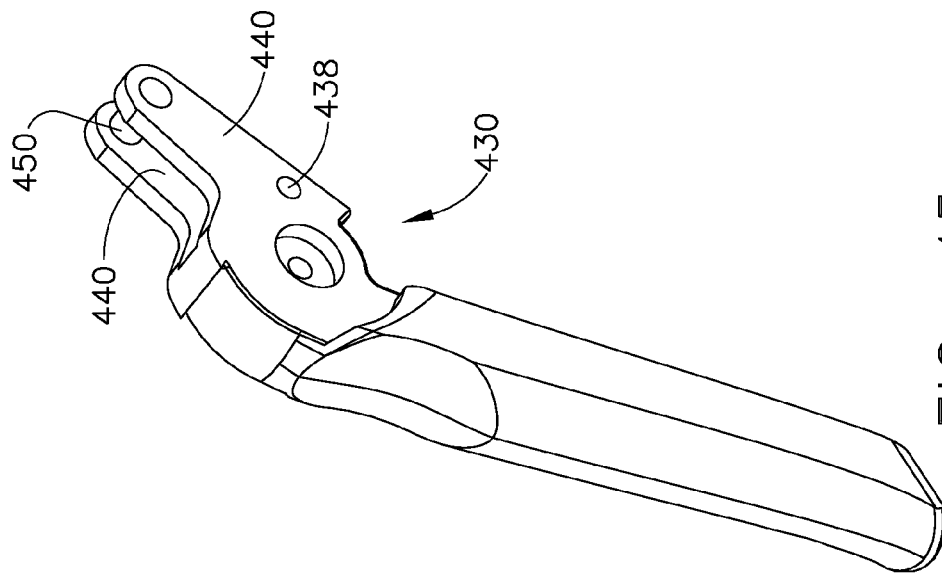
FIG. 45 is a perspective view of the trigger in isolation.

Handle 422 includes a pistol grip 426 and an actuating member, such as a manually moveable trigger 430. Trigger 430 pivots about a pin 436 that extends between sides of a handle housing 442 and through one end of the trigger. Proximal of pivot pin 436, trigger 430 is split into a pair of sidewalls 440, shown in FIGS. 43 and 45. A first spring retaining pin 438 extends perpendicularly between the sidewalls 440 to connect a return spring 444 to the trigger. The opposite end of return spring 444 is connected to the handle housing 442 by a pin 446. Return spring 444 biases trigger 430 into an open, unsqueezed position. A deploying pin 450 extends between trigger sidewalls 440, above spring retaining pin 438. When the grip of trigger 430 is squeezed, the trigger pivots about pin 436 to rotate deploying pin 450 in a distal, upward direction towards the cartridge, as will be described in more detail below. A small diameter outer tube 464 extends distally from handle 422. As in the previous embodiment, tube 464 is optimally sized to allow for passage through a small (3-5 mm) diameter trocar, although specific applications may allow for or require larger sizes.

Figure 48:
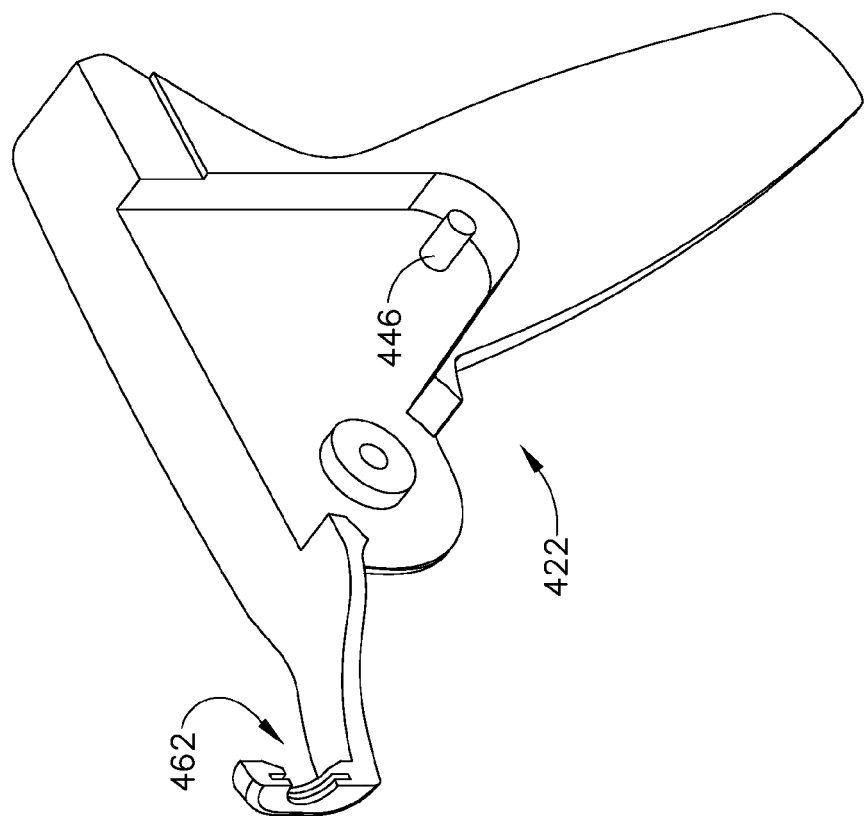
FIG. 48 is a perspective view showing a portion of the handle housing in isolation.
Figure 47:
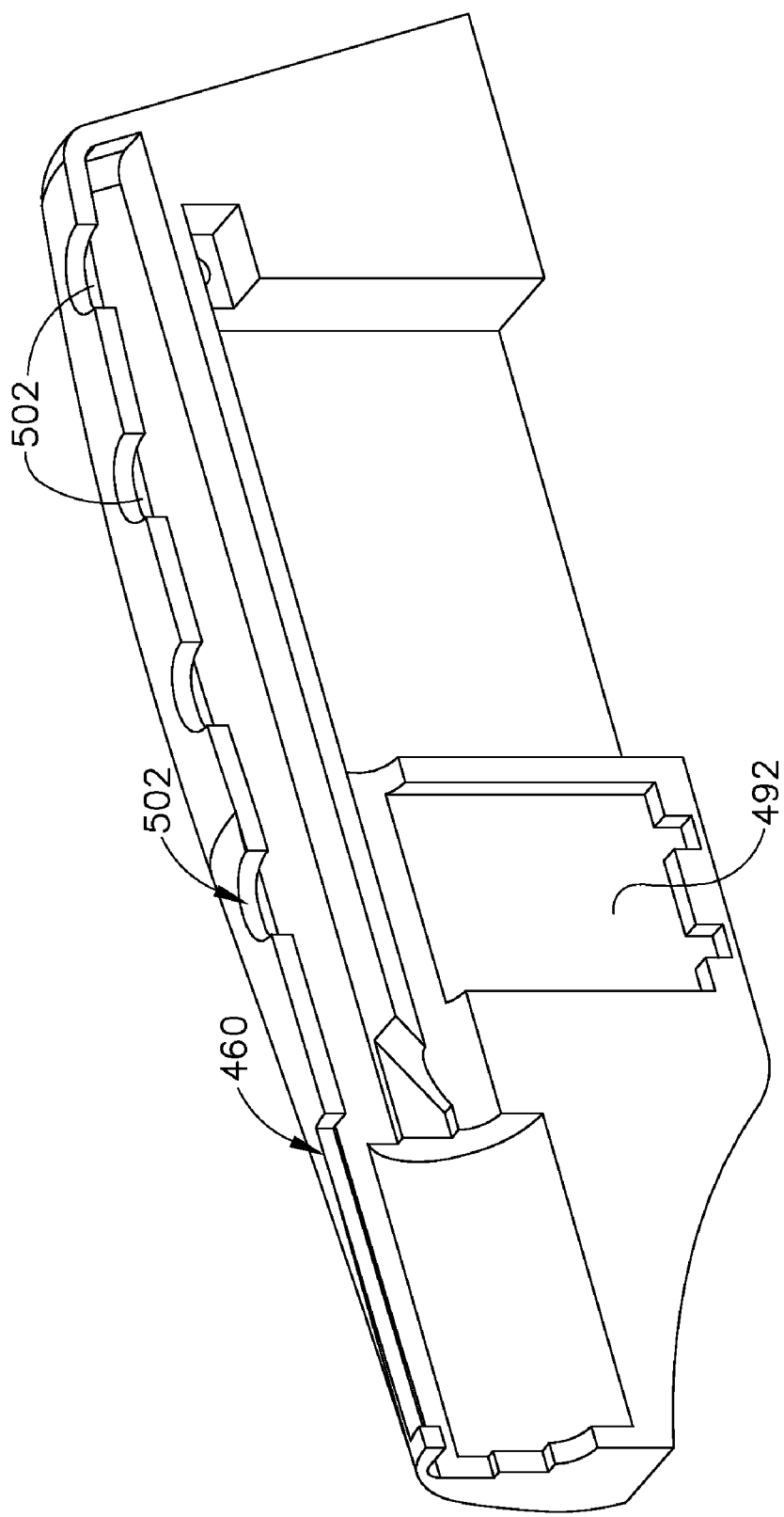
FIG. 47 is a perspective view showing a portion of the cartridge housing in isolation.

Cartridge 424 includes an elongated, distally extending protective sheath 432. As in the previous embodiments, sheath 432 is sized for passage through a small diameter trocar port, and has sufficient length to enable use within an obese patient at numerous trocar access sites. A cutting V-notch 466, as shown in FIG. 46, is formed in the distal end of sheath 432. A button 454 is mounted on the top of cartridge 424. Button 454 includes a connecting piece 456 that extends beneath the button and into a track 460 in the cartridge housing. The proximal end of sheath 432 extends through a bore in connecting piece 456 to attach the sheath to button 454. As mentioned above, numerous means may be used for attaching sheath 432 to connecting piece 456. As button 454 is slid along the surface of cartridge 424, connecting piece 456 reciprocates within track 460 (also shown in FIG. 47) to retract and advance sheath 432. As shown in FIG. 48, an opening 462 is formed at the distal end of handle 422 for connecting outer tube 464, so that sheath 432 can pass through the handle and outer tube during loading of a cartridge.

Figure 49:
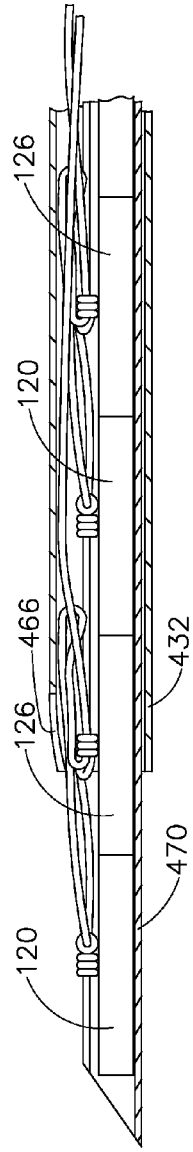
FIG. 49 is a side, sectional view of the distal end of the device, showing a stack of T-Tag anchors in the needle lumen.

Housed within sheath 432 are at least one fastener and a tissue penetrating member for inserting the fastener into or through tissue, such as a gastric cavity wall. As described above, the penetrating member can be a needle having a slotted lumen that extends proximally from a sharpened tip, through the length of the needle. The needle can have a number of different shapes and configurations, and can be formed from injection molded plastic, be extruded in a plastic or ceramic material, or fabricated from sheet metal in a progressive die operation. Various treatments, coatings, and mechanical alterations can be used to enhance and/or prolong the sharpness of the needle while minimizing the size of the resulting defect. Also as described in the previous embodiments, the cartridge needle at least partially retains and deploys one or more tissue fasteners, such as, for example, pairs of pre-tied T-Tag anchors. As shown in FIGS. 44 and 49, a plurality of the pre-tied anchor pairs are loaded into the needle lumen, such that the first "looped" T-Tag anchor 120 deploys initially, followed by the second "attached" T-Tag anchor 126, although the order may be reversed. The anchor pairs are stacked one against another within the needle lumen, and each anchor is positioned so that the suture from the anchor passes approximately normal to the anchor axis through the needle slot. Features such as described above, may be incorporated into the needle embodiments to prevent the unintentional release of the fastener components.

FIG. 43 shows an exemplary needle 470 in which the proximal end of the needle is attached to the cartridge housing 434 by a pin 472. Pin 472 extends perpendicular to the needle axis, through a hole in the needle, to hold the needle stationary during fastener deployment. A pushrod 474 is disposed within the needle lumen, with the distal end of the pushrod in contact with the proximal end of the T-Tag anchor stack. Proximal of pushrod 474, within the needle lumen, is a force transferring member 480. As shown in greater detail in FIG. 50, force transferring member 480 includes a longitudinally extending shaft 482 and axially spaced legs 484, 486 that extend downward from the proximal end of the shaft. Legs 484, 486 are spaced apart a distance to accommodate deploying pin 450 on trigger 430 when the pin is rotated upward into the cartridge. As shown in FIG. 51, needle 470 includes a slotted opening 476 adjacent the proximal needle end, through which transferring member legs 484, 486 extend outside of the needle lumen. A spring 488, shown in FIG. 43, is attached to the proximal end of force transferring member 480 to maintain the member in a proximal, stationary position prior to deployment of the fasteners.

Figure 52:
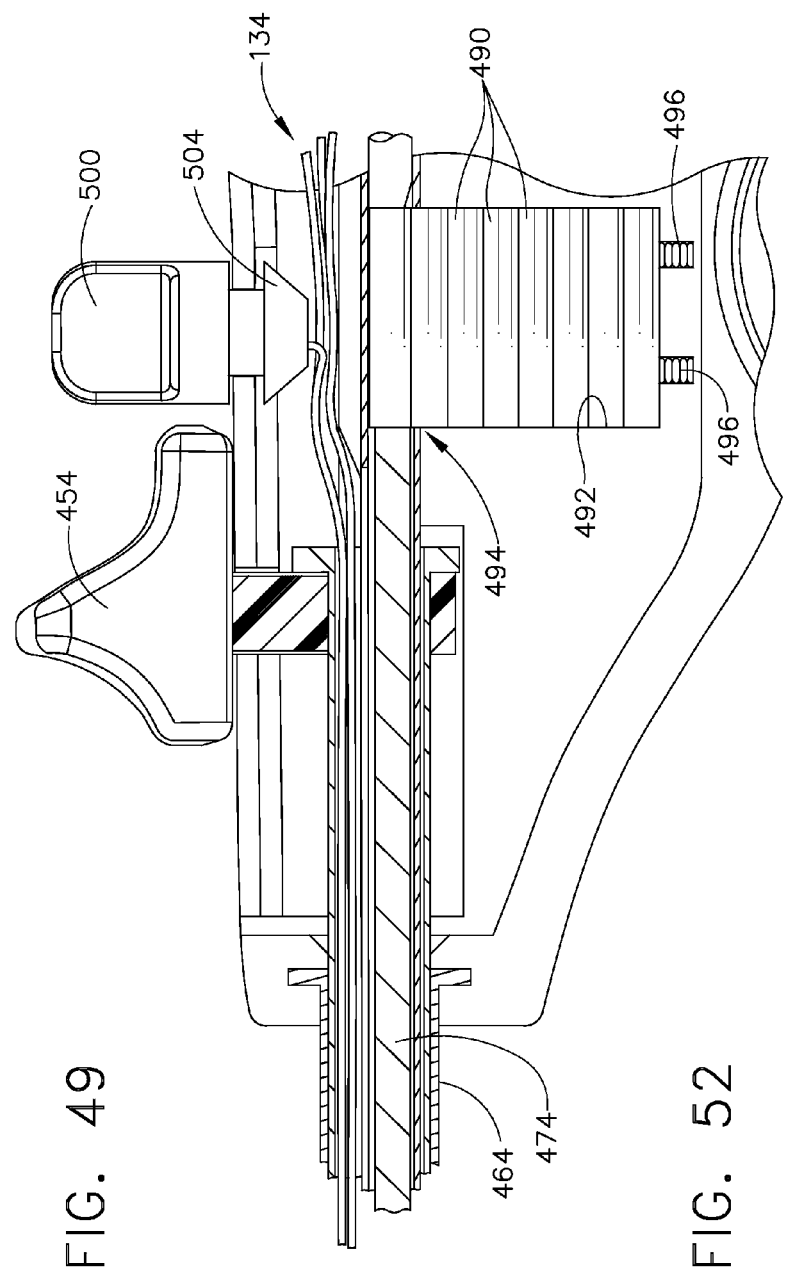
FIG. 52 is a sectional view of a mid-section of the fastener deploying device, showing the extender stack in greater detail.

Distal of force transferring member 480, cartridge 424 includes a plurality of pushrod extenders 490. As shown in FIG. 52, extenders 490 are vertically stacked within a cavity 492 in the cartridge. Multiple stacking patterns can be used to optimize the number of spacers placed in the space allotted. Exemplary examples include offset vertical stacks, revolver style stacks, etc. Each of the extenders 490 has a diameter that is less than the inner diameter of the needle lumen, and a length substantially equal to the length of a T-Tag anchor. As shown in FIGS. 51 and 52, needle 470 includes a side opening 494 that is axially aligned with the stack of extenders 490. The extenders are biased in the direction of needle opening 494 by springs 496. Prior to the initial T-Tag anchor deployment, force transferring member 480 may be in direct contact with pushrod 474, and extenders 490 stacked beneath the pushrod. In this scenario, the top extender in the stack would advance into the needle lumen following the deployment of the initial T-Tag anchor. Alternatively, as shown in FIG. 44, an extender may initially be located between pushrod 474 and force transferring member 480 prior to deployment of the first T-Tag anchor. In this scenario, the initial extender is advanced forward by the force transferring member during deployment of the first T-Tag anchor, to create an opening for the next extender in the stack to advance upward into the needle after the anchor is deployed. In either scenario, the extender stack includes at least enough extenders to allow all of the T-Tag anchors within the needle lumen to be pushed out of the open needle tip, and contact to be maintained between each of the driving parts within the needle lumen (i.e. pushrod, extenders and transferring member), so that a driving force on transferring member 480 can be passed through the needle lumen to the T-Tag anchor stack.

As shown in FIGS. 43 and 44, a plurality of pull tabs 500 protrude from the outer surface of cartridge 424. Each of the pull tabs 500 is attached to a loose end of the suture lengths 134, which extend from the fasteners in the needle lumen. Cartridge housing 434 includes openings 502 (shown in FIG. 47) through which the pull tabs 500 extend into the body of the cartridge. Plugs 504, shown in FIG. 52, are located at the base of each pull tab 500 for holding the tab within the cartridge, and preventing the unintentional release of the pull tab prior to deployment of the attached fastener. As mentioned above, various different types of identifying criteria may be used to distinguish between the pull tabs 500, in order to discern the order in which the tabs are to be removed to cinch the attached fasteners.

Figure 53:
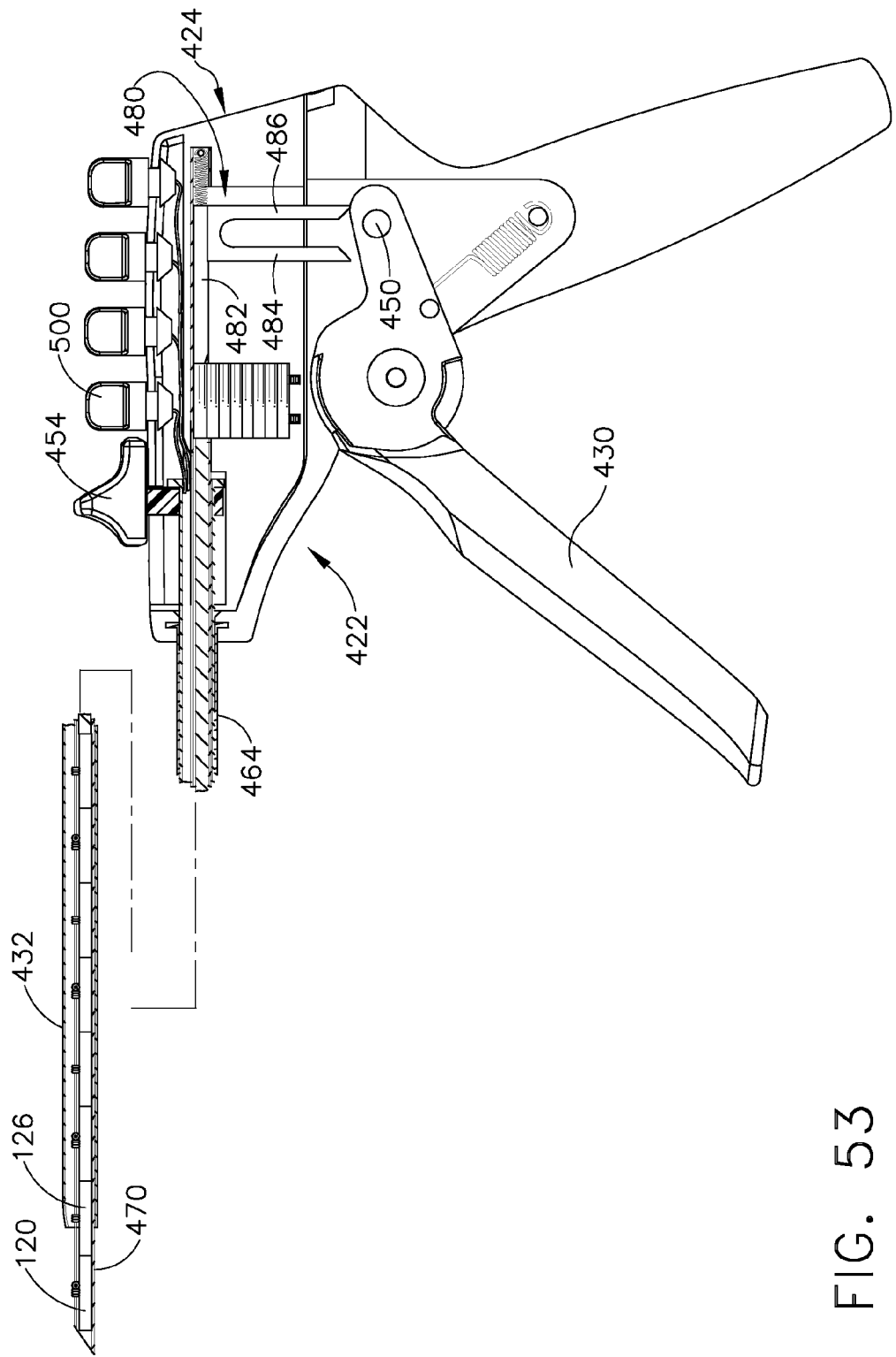
FIG. 53 is a side, sectional view of the device, showing the sheath retracted from the needle tip.

To load a cartridge 424 onto handle 422, the distal end of sheath 432 is inserted through handle opening 462 and outer tube 464. Handle opening 462 may be angled, or funneled, to facilitate the insertion of sheath 432. As cartridge 424 is slid onto handle 422, transferring member legs 484, 486, which extend beneath the cartridge, are advanced through the proximal open end of the handle to a position above deploying pin 450. To deploy a T-Tag anchor at a desired tissue location, button 454 is drawn proximally along the outer surface of cartridge 424, as shown in FIG. 53. As button 454 retracts, the attached sheath 432 is retracted away from the sharpened distal tip of needle 470. With the tip of needle 470 exposed, the device is ready to be inserted into body tissue.

Figure 54:
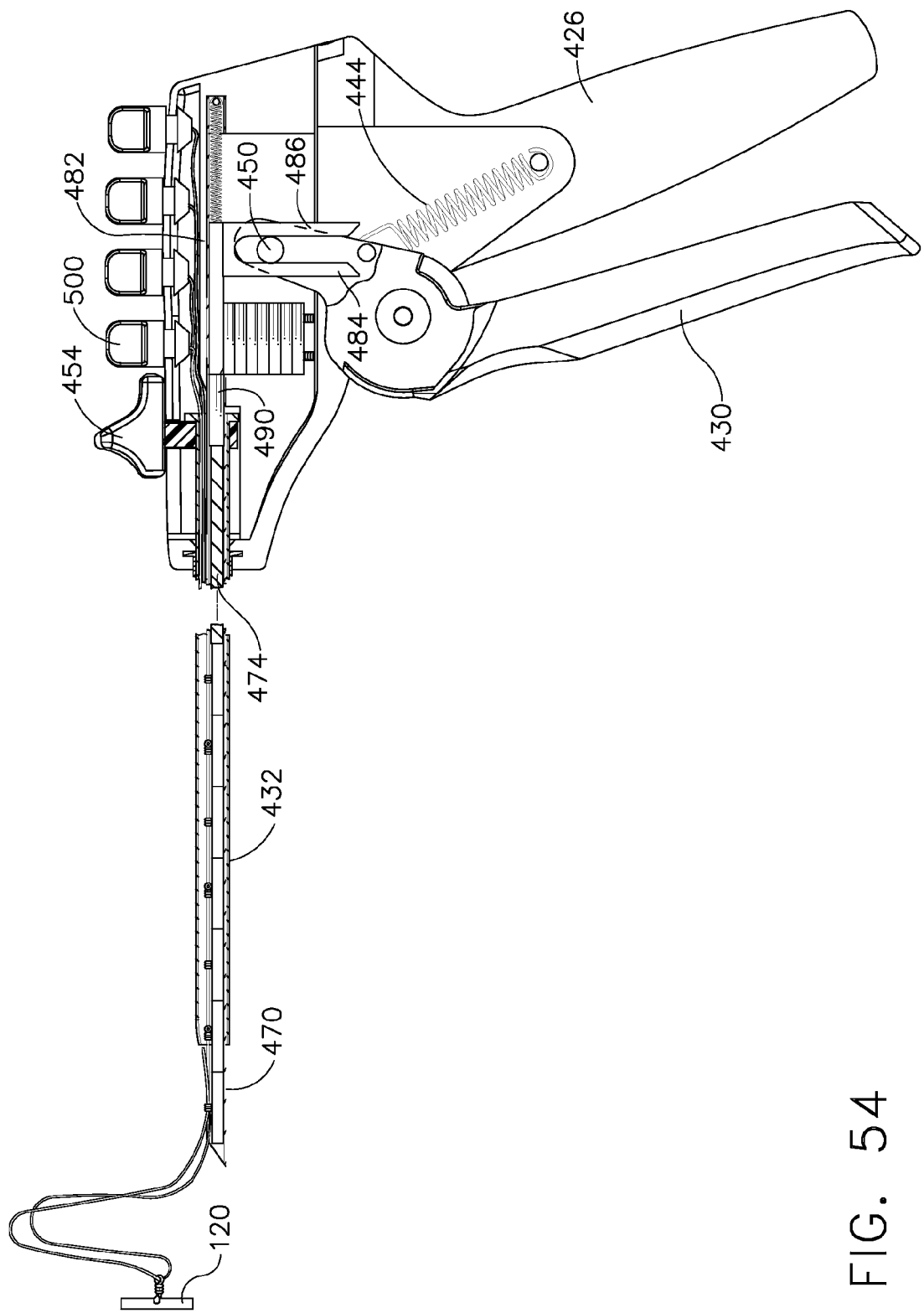
FIG. 54 is a side, sectional view of the device showing deployment of an initial T-Tag anchor.

After needle 470 is inserted into or through the body tissue, trigger 430 is manually squeezed to deploy a T-Tag anchor. As trigger 430 is squeezed, the pivoting action of the trigger drives deploying pin 450 upward and into force transferring member 480. The tips of transferring member legs 484, 486 may be tapered to facilitate movement of the pin into the channel between the spaced legs. The transferring member legs 484, 486 may also be of different lengths to facilitate this movement. As pin 450 engages force transferring member 480, the pin is simultaneously being driven distally by the pivoting of trigger 430, causing pin 450 to push against distal transferring member leg 484, and thereby drive shaft 482 of the transferring member distally within needle 470. The distal force of transferring member shaft 482 in turn drives the extender 490 (if present) and pushrod 474, to apply a distal force against the proximal end of the T-Tag anchor stack. The advancing force of pushrod 474 drives the distal-most T-Tag anchor through the open needle tip and out of the device, as shown in FIG. 54.

As the distal-most T-Tag anchor is deployed, trigger 430 reaches the fully pivoted position, providing feedback to the surgeon to release the trigger grip. As trigger 430 is released, the trigger pivots back open under the force of return spring 444. As the trigger pivots open, deploying pin 450 pushes against the proximal transferring member leg 486, thereby driving the force transferring member 480 back proximally within the cartridge. As force transferring member 480 retracts, push rod 474 remains distal, leaving a void within the needle lumen above the stack of extenders 490. As force transferring member 480 retracts just proximal of needle opening 494, the top extender in the stack advances under the force of springs 496 to fill the void in the needle lumen. The extender 490 pops into the needle lumen between the proximal end of the push rod 474 and the distal end of the transferring member shaft 482. With the extender 490 now positioned within the needle lumen, the length of pushrod 474 has effectively been increased a distance equal to the length of the deployed T-Tag anchor, thereby maintaining continuous contact between the driving components, and enabling the force transferring member and push rod to again be advanced the same distance on a subsequent squeeze of the trigger to deploy an additional T-Tag anchor.

After needle 470 is inserted into or through the body tissue in a separate location, trigger 430 is again squeezed and the force transferring member 480 is again driven distally under the force of the pivoting deploying pin 450. The force transferring member advances against the extender 490 a distance equal to a single T-Tag anchor in the needle stack. The extender 490 in turn pushes against push rod 474, which drives the stack forward to deploy the distal-most T-Tag anchor 126. After the second T-Tag anchor 126 of the fastener has been deployed, trigger 430 is released to pivot back to an open position. As trigger 430 pivots open, force transferring member 480 is drawn proximally within the needle lumen, again leaving a void in the lumen above the extender stack. The next extender, therefore, moves up into the needle lumen, to further increase the effective length of the pushrod within the needle. After the trigger is released, button 454 may be advanced to draw sheath 432 back over the tip of needle 470. With the needle tip covered, the pull tab 500 associated with the first deployed fastener can be drawn out of the cartridge, and a force applied to the tab to tension the attached suture length 134, as described in the previous embodiments. As the suture length 134 is tensioned, the deployed T-Tag anchors are drawn together to oppose the surrounding tissue.

After the initial fastener has been deployed and cinched together, the suture extending from the fastener can be severed using the V-notch 466 or other appropriate means, and the device moved to a different location to continue deploying fasteners. After all of the fasteners in the cartridge have been deployed, the cartridge may be removed from the proximal end of the handle, as in the previous embodiments, and a new cartridge loaded onto the handle in order to continue the procedure.

Figure 55:
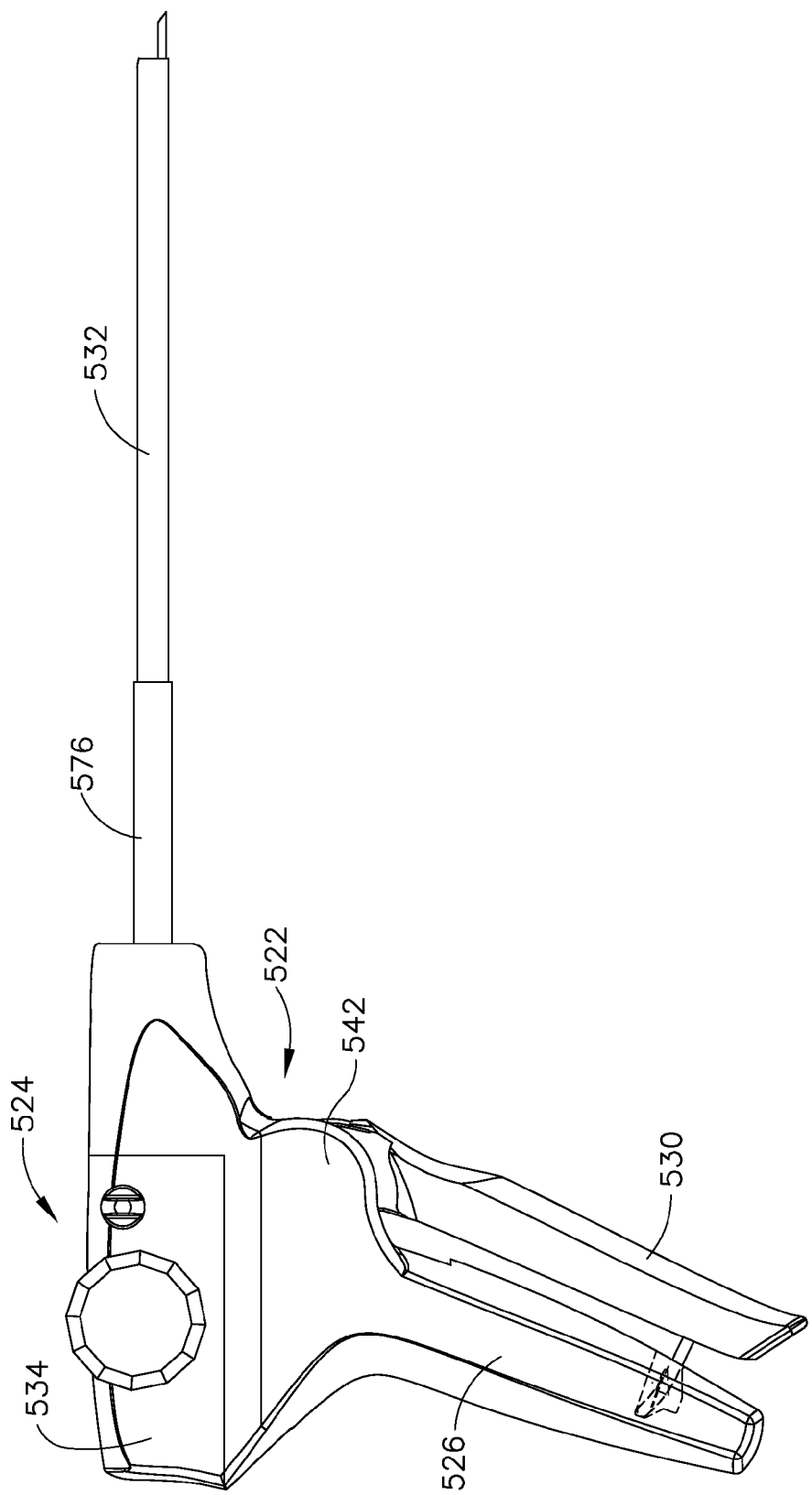
FIG. 55 is a side view of a fourth embodiment for a fastener deploying device of the invention.
Figure 56:
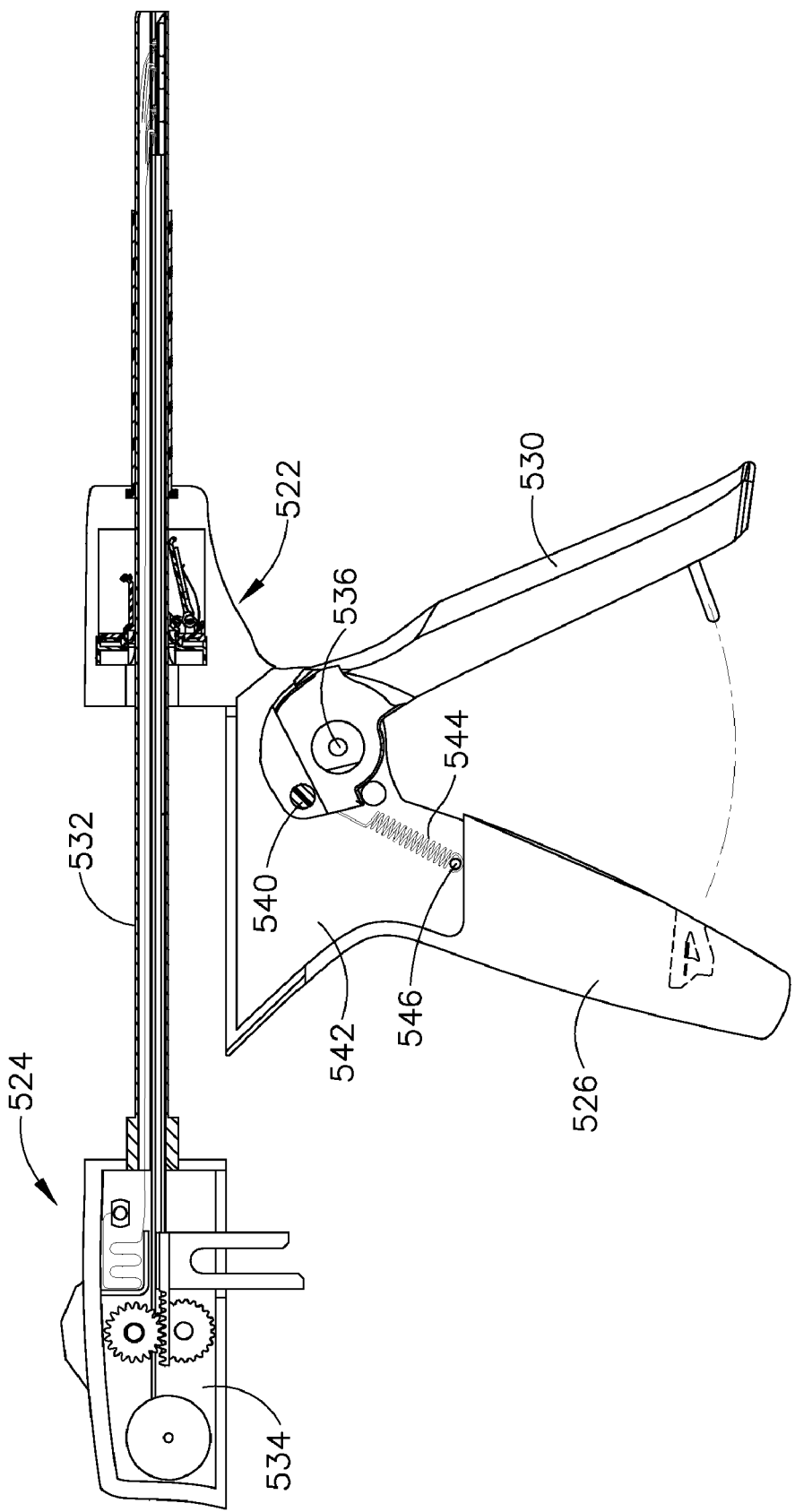
FIG. 56 is a side, sectional view of the fastener deploying device of FIG. 55, showing a cartridge being loaded onto a handle.

Turning now to FIGS. 55 and 56, which show a fourth embodiment for a fastener deploying device of the present invention. In the fourth embodiment, the device again includes a handle 522 and a releasable fastener cartridge 524 attachable to the proximal end of the handle. Cartridge 524 includes an elongated, protective sheath 532 extending distally from a housing 534. As in the previous embodiments, sheath 532 has sufficient length (on the order of 18") to enable use within an obese patient at numerous trocar access sites. Likewise, sheath 532 is sized to allow for passage through a small (3-5 mm) diameter trocar. Coupling members are provided on the device for rapidly and securely removing and attaching cartridges to the handle. The coupling members can comprise any of a number of different types of apparatus, including the deflectable catch and rib/groove arrangements described in the previous embodiments. FIG. 56 shows a cartridge 524 being attached onto a handle 522.

Handle 522 includes a pistol grip 526 and an actuating member, such as a manually moveable trigger 530. Trigger 530 pivots about a pin 536 that extends between sides of a handle housing 542 and through one end of the trigger. Above pivot pin 536, trigger 530 is split into a pair of sidewalls similar to those described in previous embodiments. A deploying pin 540 extends between the sidewalls and connects a return spring 544 to the trigger. The opposite end of return spring 544 is connected to the handle housing 542 by a second pin 546. Return spring 544 biases trigger 530 into an open, unsqueezed position. When the grip of trigger 530 is squeezed, the trigger pivots about pin 536 to rotate deploying pin 540 in a distal, upward direction towards the cartridge, as will be described in more detail below.

Figure 57:
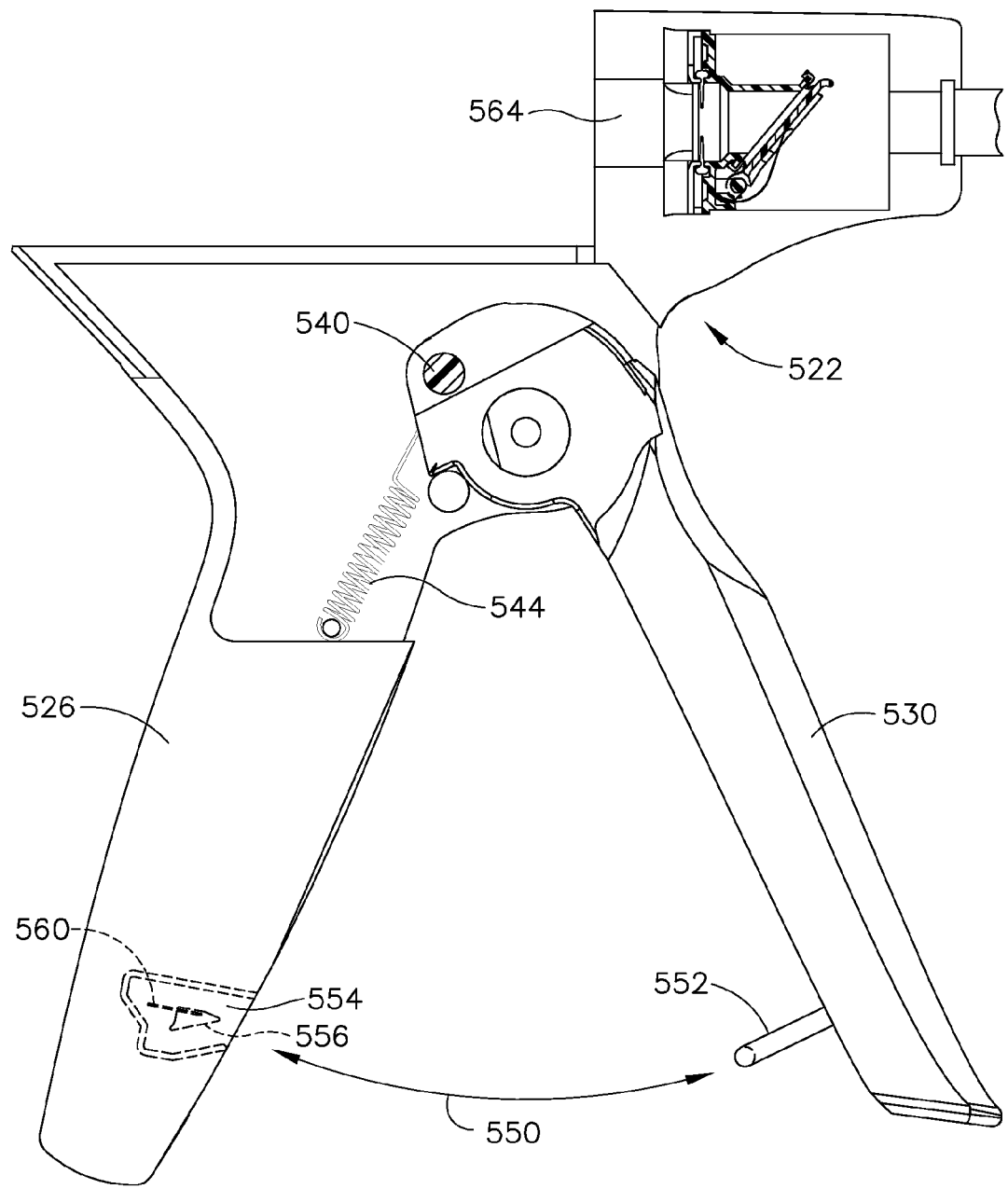
FIG. 57 is a side view, partially in section, of the handle.
Figure 60:
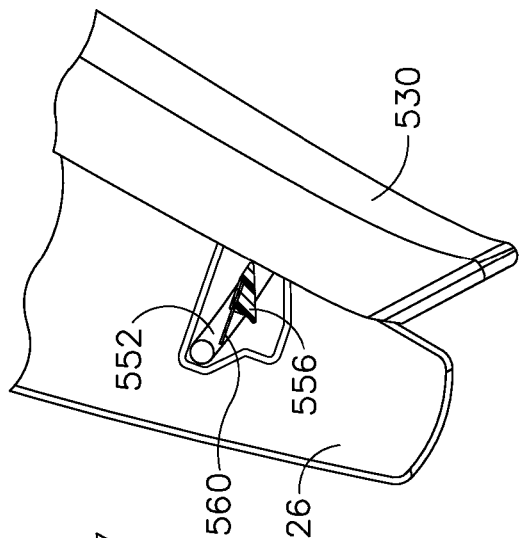
FIG. 60 is a side view, similar to FIG. 58, showing the trigger fully squeezed to release the latching mechanism.
Figure 59:
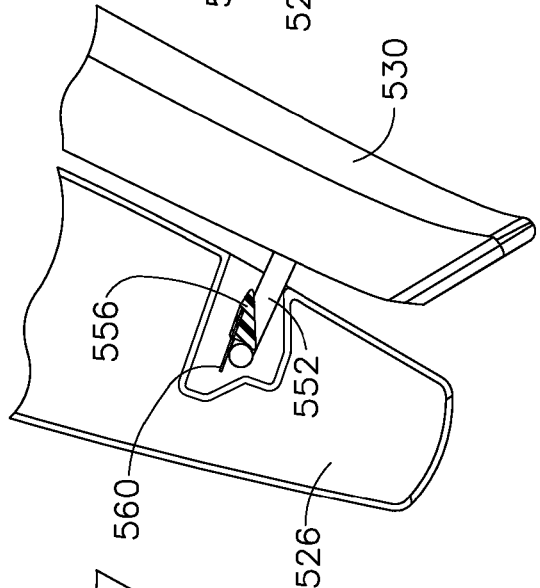
FIG. 59 is a side view, similar to FIG. 58, showing the trigger latched to the pistol grip.
Figure 58:
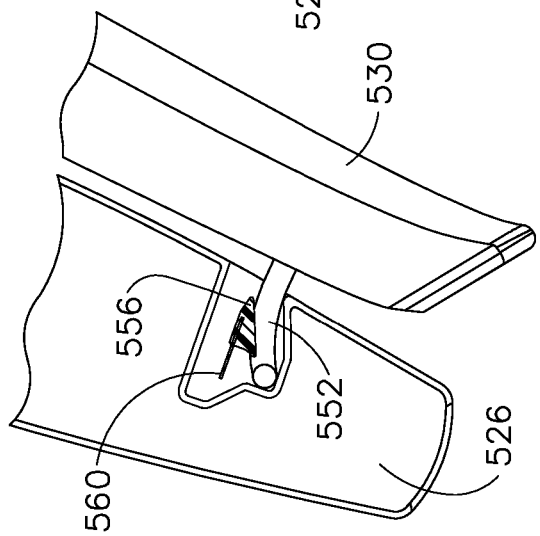
FIG. 58 is a side view, partially in section, showing a latching mechanism during an initial squeezing of the trigger.

As shown in FIG. 57, a latching mechanism 550 is provided at the base of trigger 530 and pistol grip 526. Latching mechanism 550 includes a proximally-projecting, deflectable piece 552 on trigger 530. A cavity 554 is formed into pistol grip 526 on the side facing trigger 530. A catch 556, having a deflectable strip 560, is located inside cavity 554. Latching piece 552 is drawn into cavity 554 during squeezing of trigger 530, as shown in FIG. 58. As piece 552 enters cavity 554, the piece deflects up so that an angled end of the piece contacts the proximal face of catch 556, as shown in FIG. 59. Catch 556 retains piece 552 inside of cavity 554, thereby holding trigger 530 in a pivoted position. To release trigger 530, latching piece 552 is disengaged from catch 556 by fully squeezing the trigger until the trigger contacts the pistol grip. As trigger 530 is fully squeezed, latching piece 552 is pushed proximally within cavity 554, deflecting strip 560 and releasing the angled end of the piece from catch 556, as shown in FIG. 60. After latching piece 552 is released from catch 556, trigger 530 pivots back to its initial, unsqueezed position under the force of return spring 544.

Figure 61:
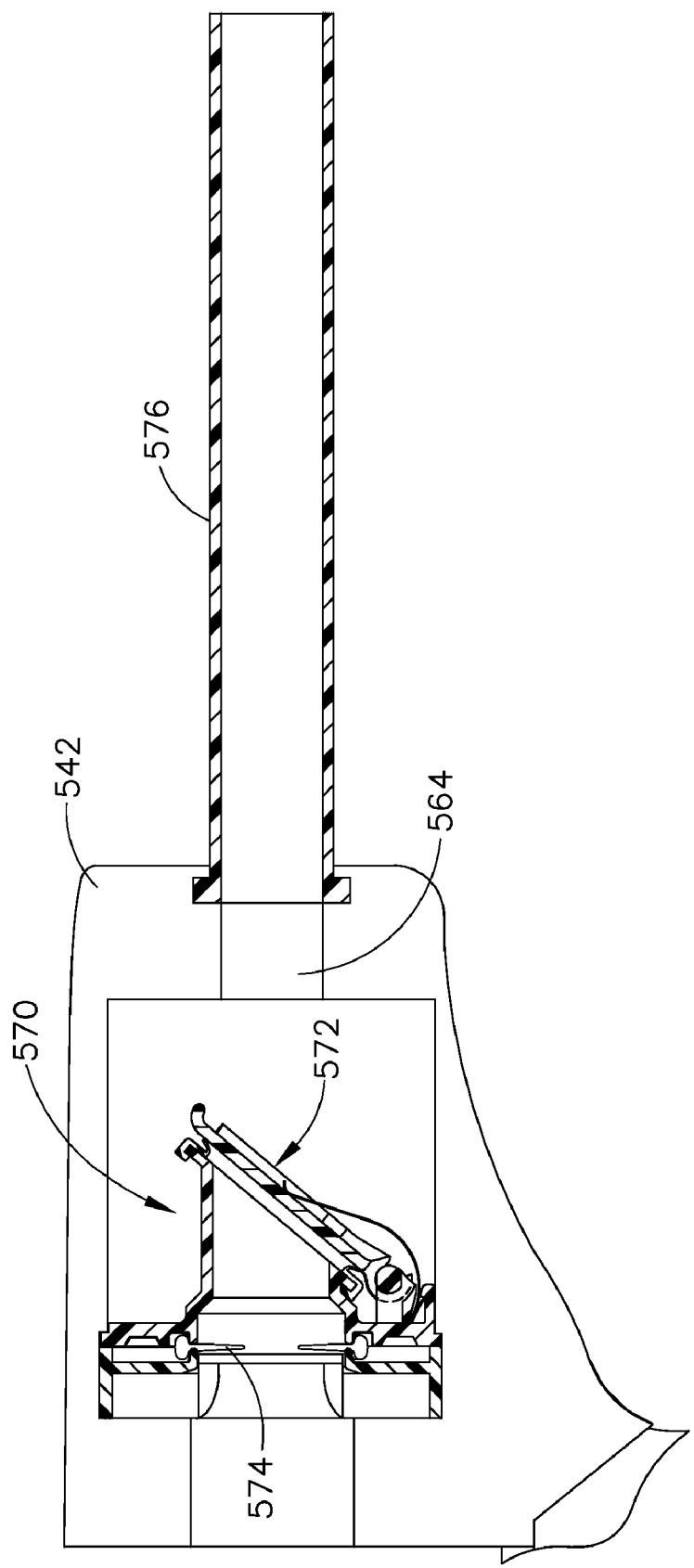
FIG. 61 is a side, sectional view showing a sealing assembly and outer tube of the handle in isolation.
Figure 62:
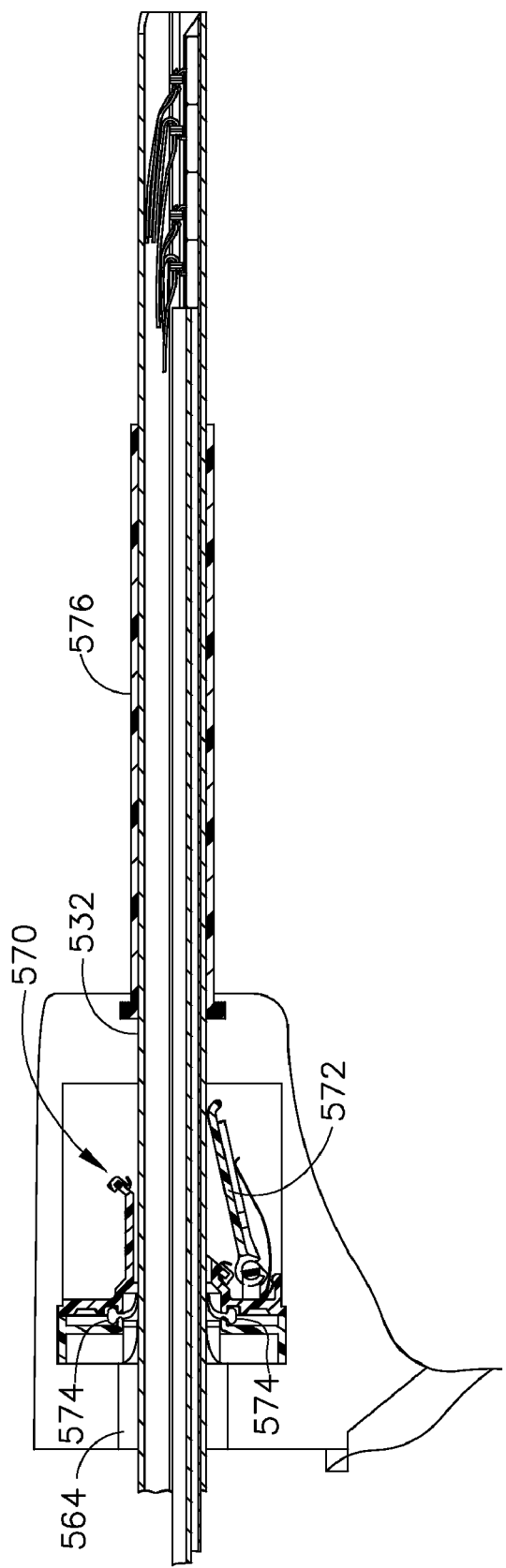
FIG. 62 is a side, sectional view, similar to FIG. 61, showing a cartridge sheath inserted through the sealing assembly and outer tube.

Returning now to FIG. 57, handle 522 includes a channel 564 through which sheath 532 passes during attachment of a cartridge to the handle. A sealing assembly is preferably provided within channel 564 to allow the cartridge sheath to pass in and out of the handle, while maintaining sealed integrity about the handle. The sealing assembly prevents the release of insufflation gas and body fluids through the handle. FIGS. 61 and 62 show detailed views of a representative sealing assembly 570 comprising a pair of axially spaced seals. The distal seal 572, typically called a duckbill valve, prevents gases and fluids from escaping through channel 564 when a cartridge is not inserted into the handle. Duckbill valve 572 includes a hinged flap that is deflected open by the distal tip of sheath 532 upon insertion of the sheath into handle channel 564. The more proximal seal is a flexible ring seal 574 that extends radially inward from a wider access opening. Ring seal 574 can be deflected open, as shown in FIG. 62, to accommodate sheath 532 when a cartridge is attached to the handle. As a cartridge is loaded, ring seal 574 conforms to the perimeter of sheath 532, to form a lock about the sheath, and prevent fluids from passing around the exterior of the sheath and out of the abdominal cavity. Such sealing assemblies, typically on commercially available trocars, are well known in the art. The sealing assembly shown herein is only representative of the types of sealing means which may be utilized with the fastener deploying devices of the present invention. Numerous other sealing devices and methods may be utilized to maintain pneumostasis during use of the fastener deploying device without departing from the scope of the invention. A small diameter outer tube 576 is connected to handle 522 distal of sealing assembly 570. Tube 576 is optimally sized to allow for passage through a small (3-5 mm) diameter trocar, although specific applications may allow for or require larger sizes.

Figure 63:
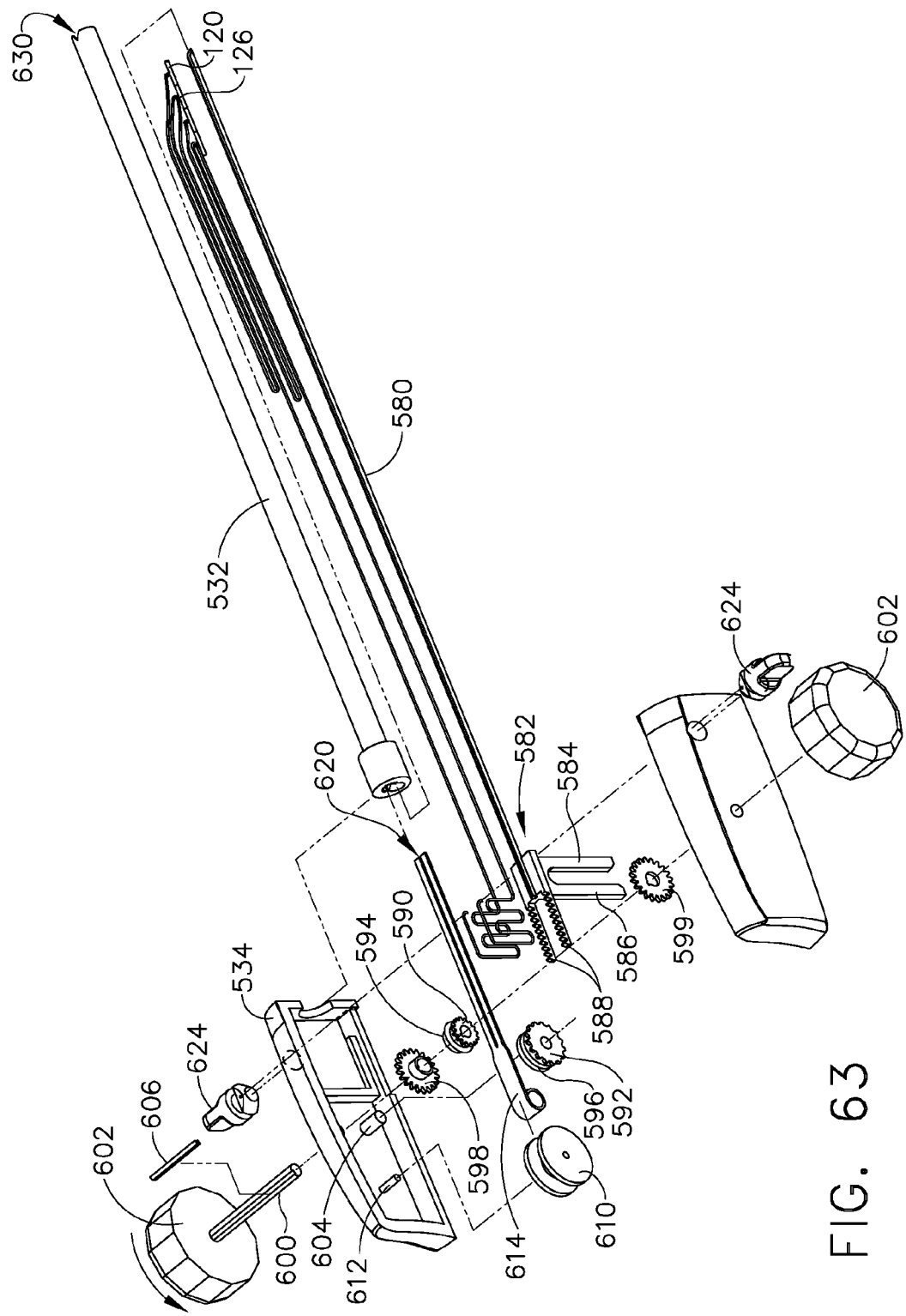
FIG. 63 is an exploded view of the cartridge shown in FIG. 56.

As shown in FIG. 63, the proximal end of sheath 532 is fixed within an opening in the distal side of cartridge housing 534. Housed within sheath 532 are at least one fastener and a tissue penetrating member for inserting the fastener into tissue, such as a gastric cavity wall. As described above, the penetrating member can be a needle having a number of different shapes and configurations, with a slotted lumen that extends proximally from a sharpened tip through the length of the needle. Likewise, as described above, the needle at least partially retains and deploys one or more tissue fasteners comprising, for example, pairs of pre-tied T-Tag anchors. A plurality of the pre-tied anchor pairs are loaded into the needle lumen, such that the first "looped" T-Tag anchor 120 deploys initially, followed by the second "attached" T-Tag anchor 126, although the order may be reversed. The anchor pairs are stacked one against another within the needle lumen, and each anchor is positioned so that the suture from the anchor passes normal to the anchor axis through the needle slot. Features, such as described above, may be incorporated into the needle embodiments to prevent the unintentional release of the fastener components.

Figure 64:
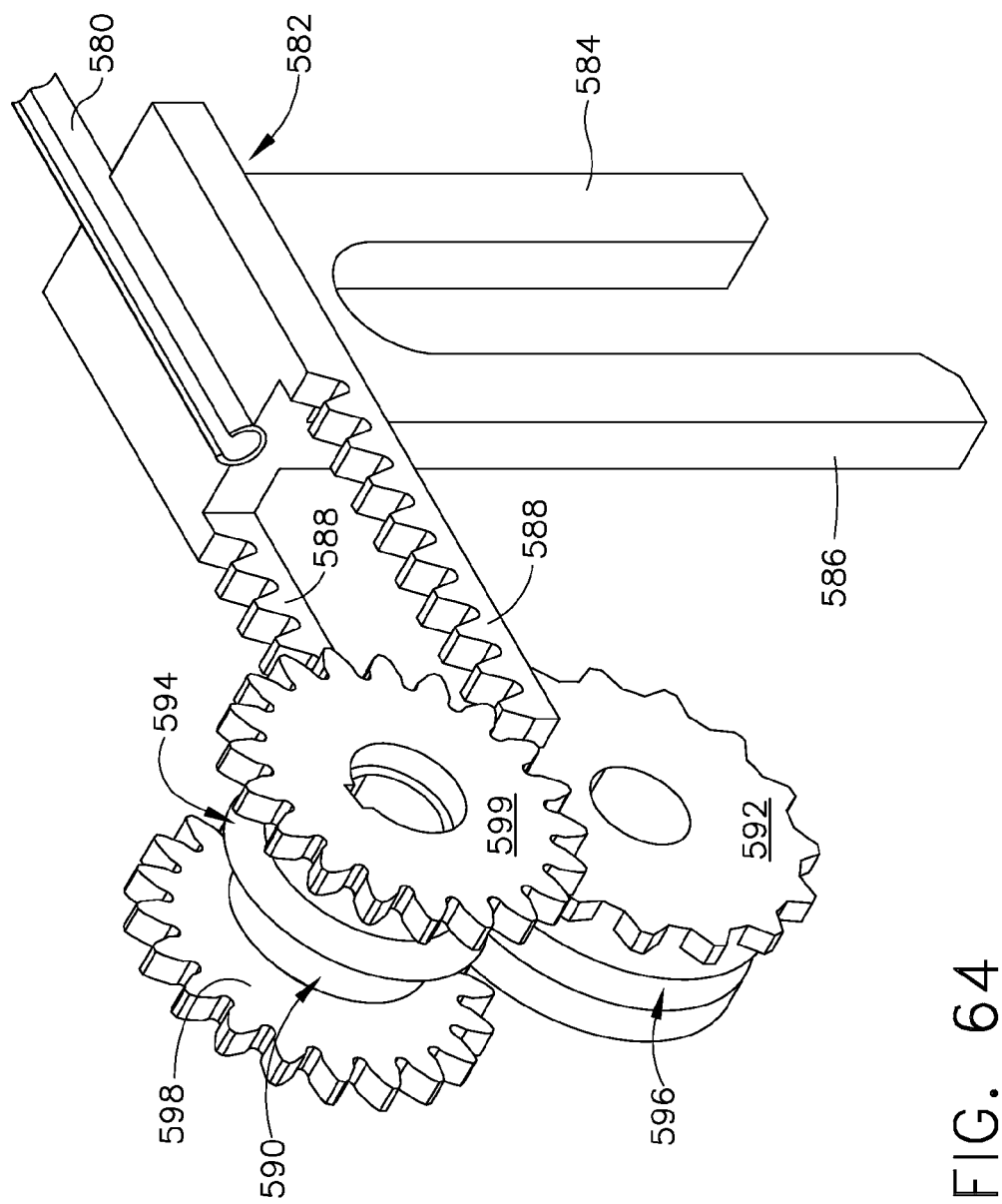
FIG. 64 is an isolated perspective view showing the force transfer member, nip rollers and gear assembly.

FIG. 63 shows an exemplary slotted needle 580 in which the proximal end of the needle is affixed to a force transferring member 582. Transferring member 582 includes a pair of spaced legs 584, 586. When cartridge 524 is attached to handle 522, transferring member legs 584, 586 extend above opposite sides of deploying pin 540. The proximal end of transferring member 582 includes parallel racks 588. Proximal of force transferring member 582, within cartridge housing 534, is a pair of nip rollers 590, 592. The upper roller 590 has a triangular projection 594 extending from the circumference of the roller, while the lower roller 592 has a triangular groove 596 formed into the circumference of the roller. As shown in FIG. 64, nip rollers 590, 592 are mounted so that projection 594 mates with and rotates within groove 596 as the nip rollers revolve within the cartridge. The upper, driving nip roller 590 includes gear teeth (shown in FIG. 63) which interlock with corresponding gear teeth on the lower, driven roller 592. Additional gears 598, 599 are located on the sides of driving roller 590. Gears 598, 599 engage racks 588 when transferring member 582 moves axially. As shown in FIG. 63, a shaft 600 extends perpendicular to the needle axis and through the center of driving roller 590 and gears 598, 599. Shaft 600 includes a slot having a key 606 disposed therein. The ends of shaft 600 are attached to knobs 602 on the outside of cartridge housing 534. Key 606 fits inside notches in the center bore of gears 598, 599, to rotate the gears when knobs 602 are rotated. A rod 604 extends between the sides of cartridge housing 534 and through the center of the second, driven nip roller 592. Nip roller 592 rotates about rod 604 in response to rotation of the driving roller 590, due to the interlocking gear teeth on the rollers. Although not shown, systems providing mechanical advantage (e.g. gears, etc.) may be employed to reduce the torque required to rotate knobs 602.

Proximal of nip rollers 590, 592 is a spool 610 which rotates about a shaft 612. A length of rigid, yet deformable, material 614 is wound on spool 610. Material 614 can, for example, comprise a metal, plastic, or other similar substance that can be advanced via friction between the nip rollers 590, 592, while simultaneously being deformed by the rollers. Material 614 should be resistant to changes in its length when placed under compressive loads, but should allow bending about the spool when wound when appropriate geometries are chosen. Material 614 is unwound from spool 610 and pulled distally between the nip rollers by the frictional contact with the rollers. As material 614 is pulled between rollers 590, 592, the material is bent into a "V" configuration by the mating triangular projection 594 and groove 596 on the rollers. The "V" depression in material 614 forms a pusher tip 620 for advancing T-Tag anchors within needle 580.

Figure 65:
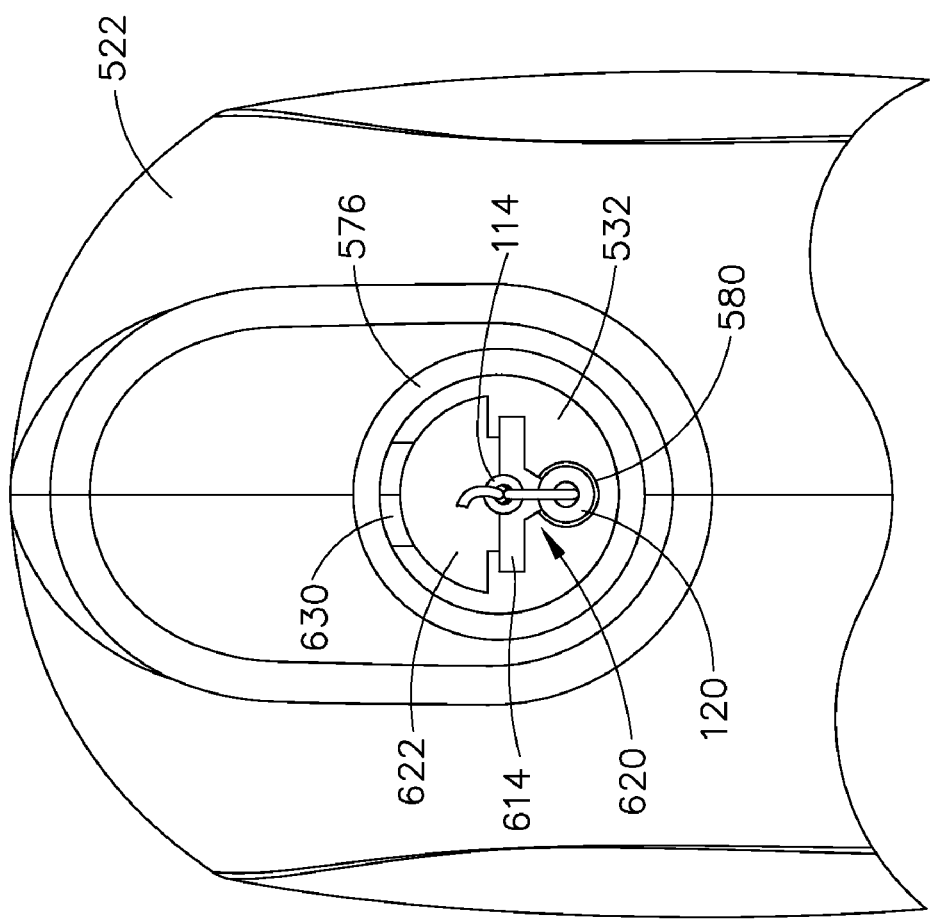
FIG. 65 is an end view of the fourth deploying device embodiment, looking in a proximal direction from the tip of the needle and sheath.

As shown in FIG. 65, sheath 532 is shaped to accommodate material 614 and "V"-shaped pusher tip 620 distal of nip rollers 590, 592. Needle 580 is oriented within sheath 532 so that the needle slot is aligned with "V" pusher tip 620 to enable the pusher tip to extend through the needle slot and into the needle lumen. Within the needle lumen, pusher tip 620 contacts the proximal end of the T-Tag anchor stack. Sheath 532 includes a passageway 622 above material 614 through which suture lengths 134 extend from the fasteners back into the cartridge housing. Within cartridge housing 534, suture lengths 134 may be individually encircled and separately stored, using any of the methods described above, to prevent the strands from becoming entangled prior to cinching of the suture.

One or more pull tabs 624, shown in FIG. 63, extend through openings in cartridge housing 534. Each of the pull tabs 624 is attached to the loose end of a suture length 134 extending from a fastener in the needle lumen. Plugs may be located at the base of each pull tab 624, for retaining the tab within the cartridge housing, and preventing the unintentional release of the pull tab prior to deployment of the attached fastener. As mentioned above, various different types of identifying criteria may be used to distinguish between the pull tabs 624, in order to discern the order in which the tabs are to be removed to cinch the attached fasteners.

Figure 66:
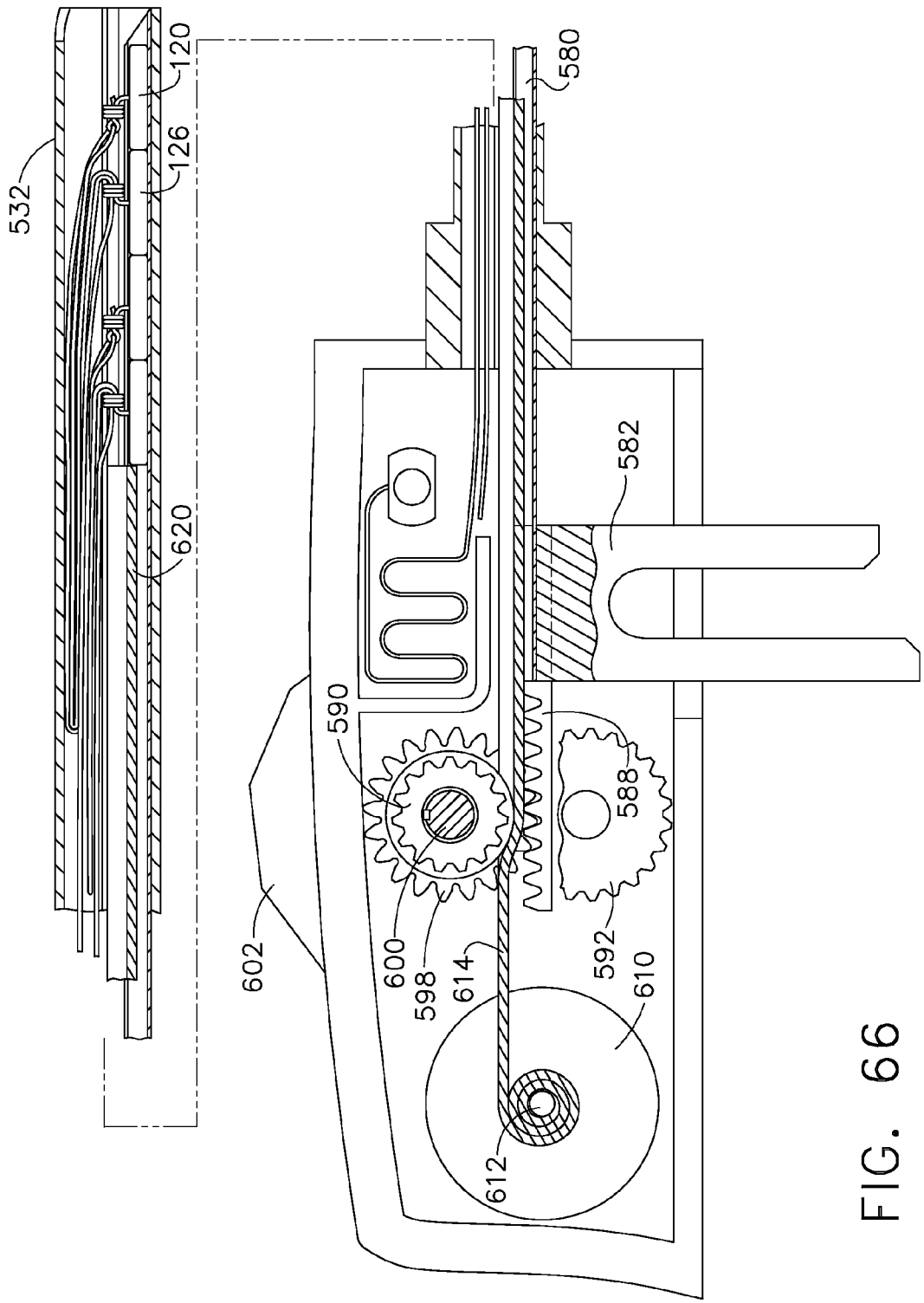
FIG. 66 is a side view, partially in section, of the proximal end of the cartridge, with a first gear removed to show the upper nip roller and the other gear engaging the force transferring member rack.
Figure 67:
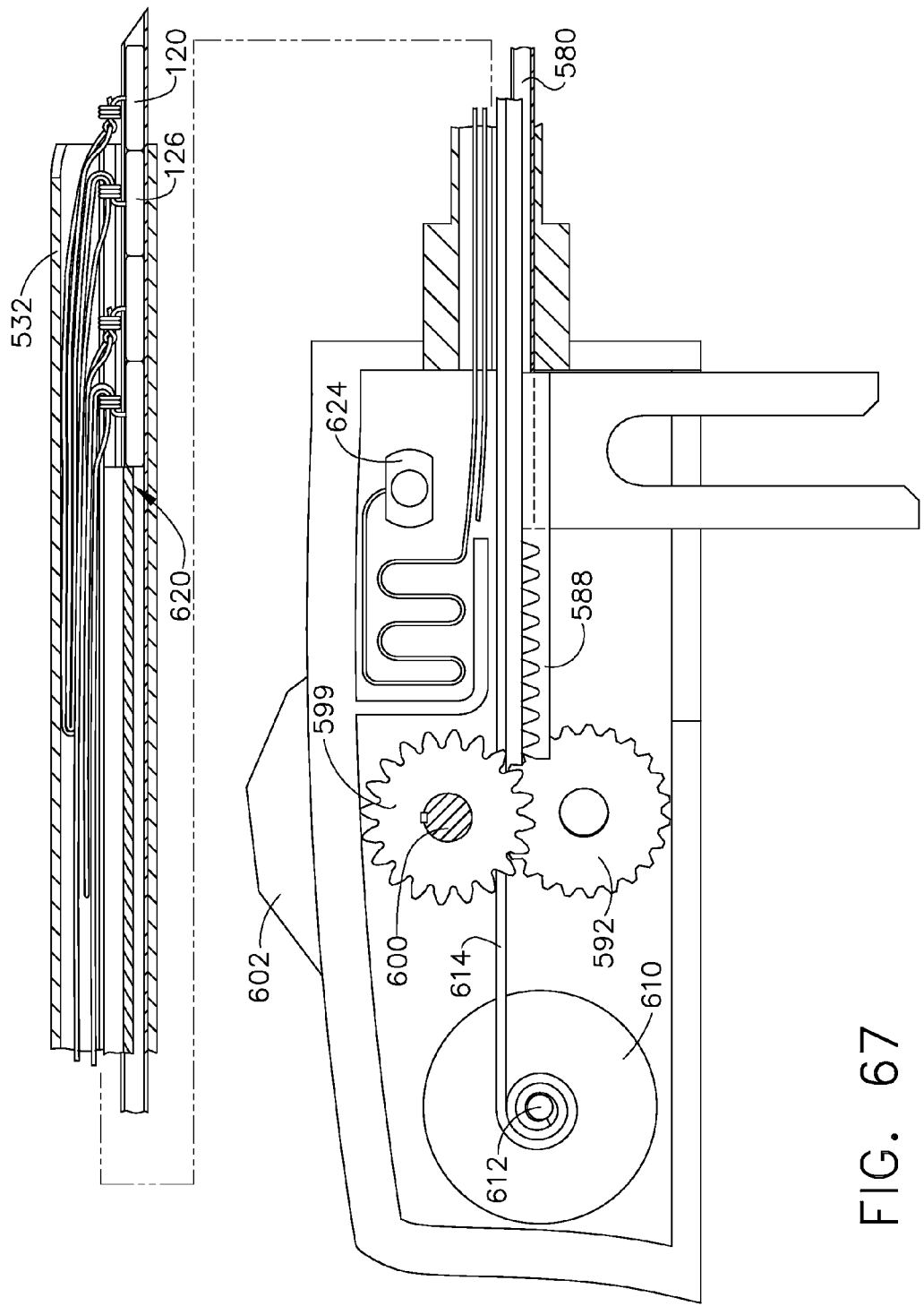
FIG. 67 is a side view, partially in section, of the proximal end of the cartridge, showing the rack advanced distally out of engagement with the gears following advancement of the needle.

To load a cartridge 524 onto handle 522, the distal end of sheath 532 is inserted into channel 564 and through sealing assembly 570. The opening to handle channel 564 may be angled, or funneled, to facilitate the insertion of sheath 532. As sheath 532 passes through sealing assembly 570, the distal tip of the sheath expands ring seal 574 and deflects open duck bill valve 572. Sheath 532 is passed through outer tube 576 and beyond the distal end of the handle. As cartridge 524 is slid onto handle 522, transferring member legs 584, 586, which extend beneath the cartridge, are advanced through the proximal open end of the handle to a position above deploying pin 540. To deploy a T-Tag anchor at a targeted tissue location, trigger 530 is squeezed to pivot the trigger. As trigger 530 pivots, deploying pin 540 rotates distally upward into the opening in force transferring member 582. The tips of transferring member legs 584, 586 may be tapered, or of differing lengths, to guide pin 540 into the force transferring member. As deploying pin 540 engages force transferring member 582, the pin applies force against the distal leg 584 to drive the transferring member and attached needle 580 in a distal direction. The distal movement of transferring member 582 advances racks 588, turning gears 598, 599, as shown in FIG. 66, by the interaction of the gear and rack teeth. The rotation of gears 598, 599 draws a section of material 614 through nip rollers 590, 592, so that the material advances distally along with needle 580 inside sheath 532. As the tip of needle 580 advances outside the end of sheath 532, latching piece 552 engages catch 556 within cavity 554, to latch trigger 530 in the pivoted position, and lock needle 580 in an outward, exposed position. At the end of the trigger stroke, gears 598, 599 disengage from the proximal end of racks 588, as shown in FIG. 67. With the tip of needle 580 exposed, the device is ready to be inserted into tissue to deploy a fastener.

Figure 68:
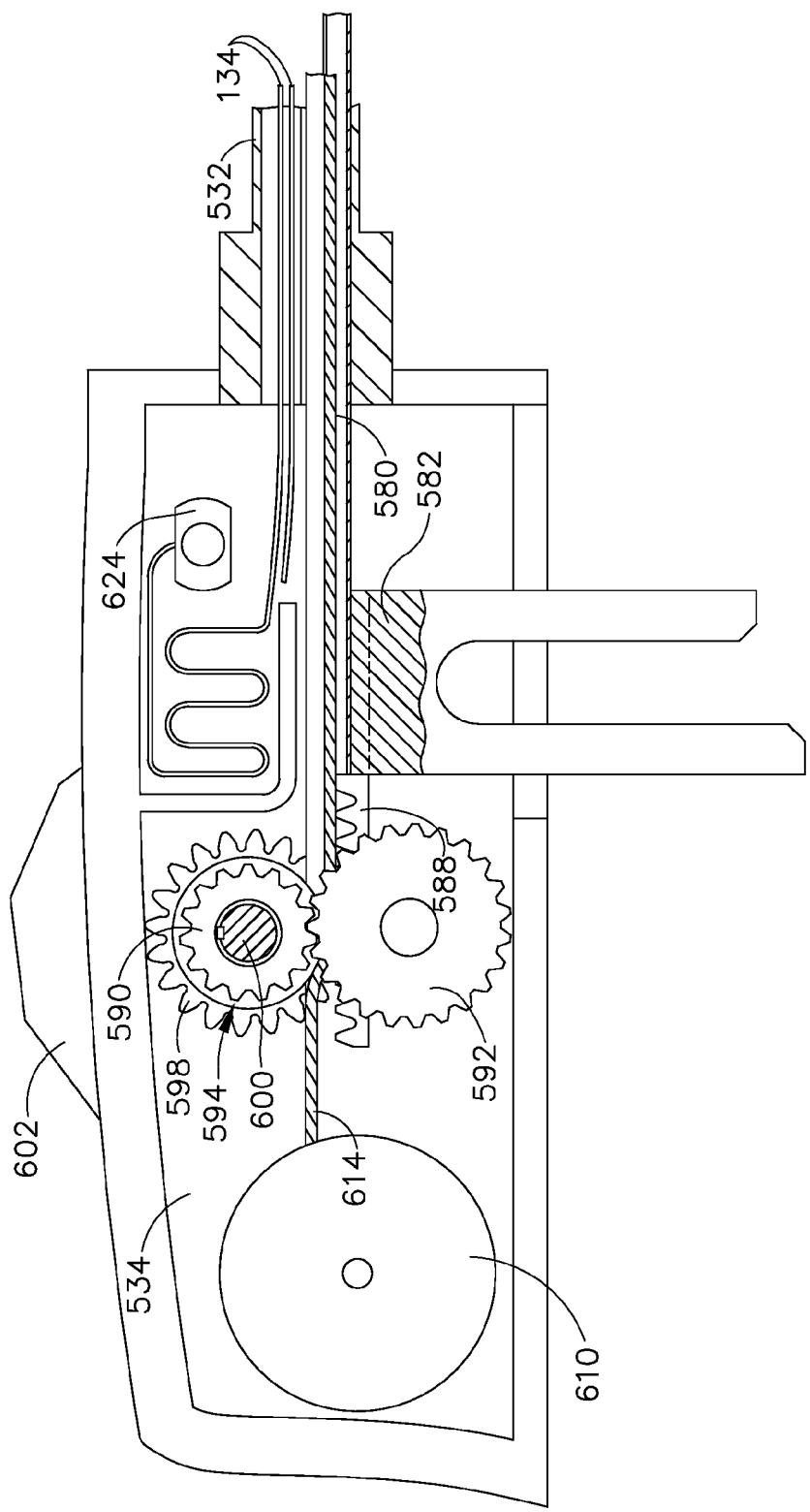
FIG. 68 is a side view, partially in section, of the proximal end of the cartridge, showing the meshing of the nip rollers and the formation of the V-shaped pusher tip.

After needle 580 is inserted into or through a section of tissue, knobs 602 are rotated to deploy a T-Tag anchor. As knobs 602 are rotated, the rotating force is transferred to driving nip roller 590, which in turn rotates lower roller 592 through the interlocking gear teeth. The rotation of nip rollers 590, 592 draws a section of material 614 from spool 610 and between the mating surfaces of the rollers. As material 614 is drawn between the roller surfaces, the material is deformed into "V" shaped pusher 620, as shown in FIG. 68. Following deformation, material 614 is advanced distally from between rollers 590, 592 by the frictional contact with the rollers. As material 614 advances distally, the material moves over needle 580, with pusher tip 620 extending into the needle lumen through the needle slot. As pusher tip 620 advances within the needle lumen, the pusher tip applies a force against the proximal end of the T-Tag anchor stack. The advancing force of pusher tip 620 drives the distal-most T-Tag anchor through the open needle tip and out of the device.

After the distal-most T-Tag anchor is deployed, feedback of the deployment is provided to the surgeon, enabling the surgeon to cease rotation of knobs 602. Latching mechanism 550 can then be released to allow trigger 530 to spring back to an open position. As trigger 530 springs open, deploying pin 540 pushes against the proximal leg 586 of force transferring member 582, drawing the transferring member and attached needle 580 back proximally within sheath 532. As transferring member 582 is pulled proximally, racks 588 reengage with gears 598, 599 to rotate shaft 600 and draw material 614 back proximally through nip rollers 590, 592. As needle 580 retracts, a section of material 614 approximately equal in length to a T-Tag anchor is drawn back through nip rollers 590, 592.

When a second T-Tag anchor location is selected, trigger 530 is again squeezed and latched to expose the tip of needle 580 outside the distal end of sheath 532. Pivoting trigger 530 also again advances the section of material 614 that was drawn proximally at the end of the previous trigger stroke. Material 614 is advanced during squeezing of trigger 530 so that the pusher tip 620 remains in contact with the proximal end of the T-Tag anchor stack as the needle is advanced. After the exposed needle tip is inserted into or through the tissue, knobs 602 are again rotated to advance an additional segment of material 614 through nip rollers 590, 592. This additional segment of material 614 forces the distal-most T-Tag anchor through the open tip of needle 580, thereby deploying the anchor. After the second T-Tag anchor 126 of the fastener has been deployed, trigger 530 is unlatched, as described previously, to pivot the trigger back to an open position and retract needle 580 and material 614. With the needle tip covered, the pull tab 624 associated with the first deployed fastener can be drawn out of the cartridge, and a force applied to the tab to tension the attached suture length 134, as described in the previous embodiments. As the suture length is tensioned, the deployed T-Tag anchors are drawn together to oppose the surrounding tissue.

After the initial fastener has been deployed and cinched, the suture extending from the fastener can be severed. A V-notch 630, shown in FIG. 63, may be provided at the distal end of sheath 532 for severing the cinched suture. Handle 522 may be manually maneuvered in order to draw suture length 134 against a sharpened, cutting edge of V-notch 630 in order to sever the suture. Alternatively, other types of known cutting methods or devices may be utilized for severing a suture length following cinching of the attached fastener. After the suture is severed, the fastener deploying device can be moved to a different location to continue deploying fasteners. After all of the fasteners in the cartridge have been deployed, the cartridge may be removed from the proximal end of the handle, as in the previous embodiments, and a new cartridge loaded onto the handle in order to continue deploying fasteners.

Figure 69:
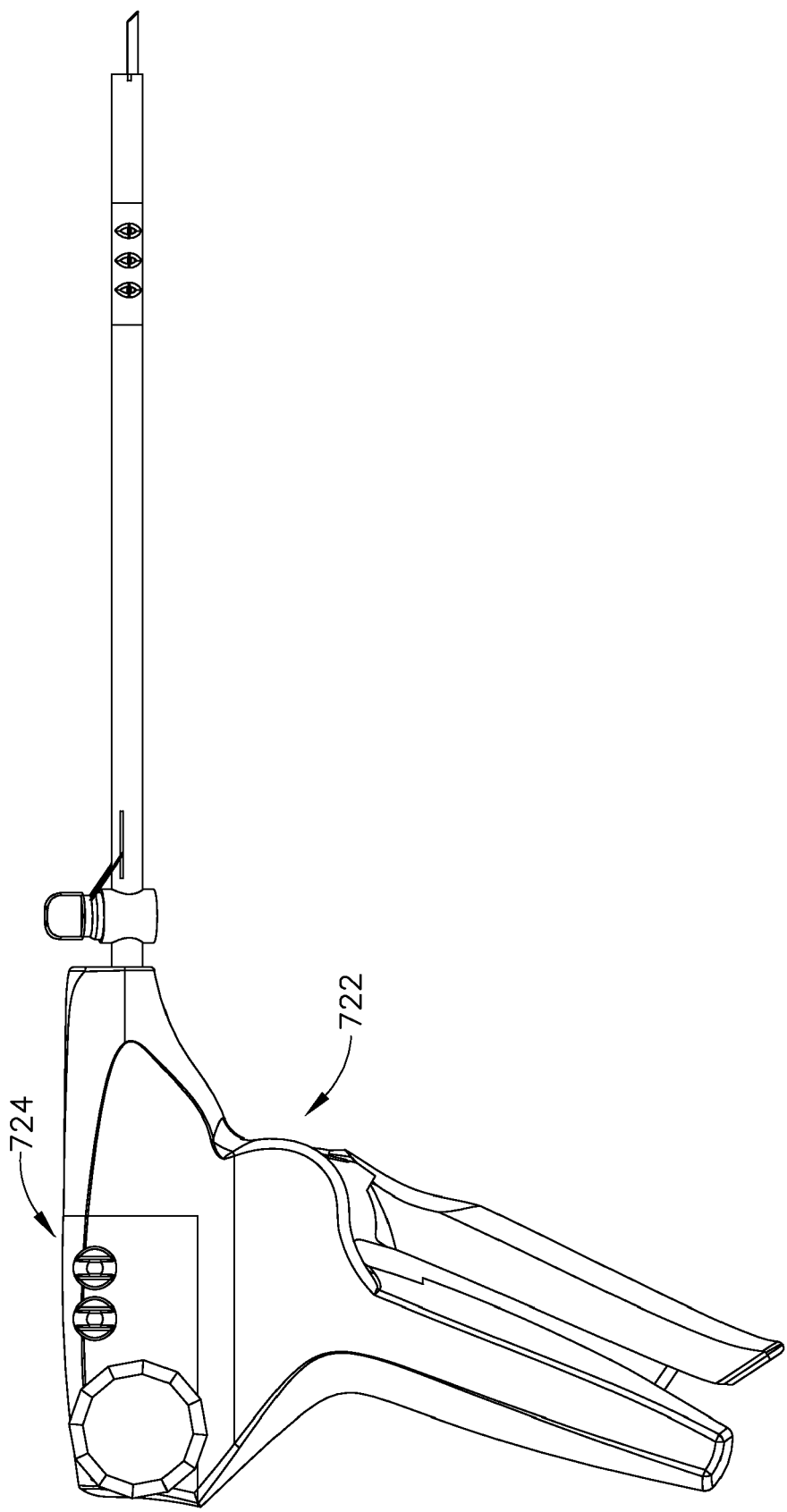
FIG. 69 is a side view of a fifth embodiment for a fastener deploying device of the invention.
Figure 70:
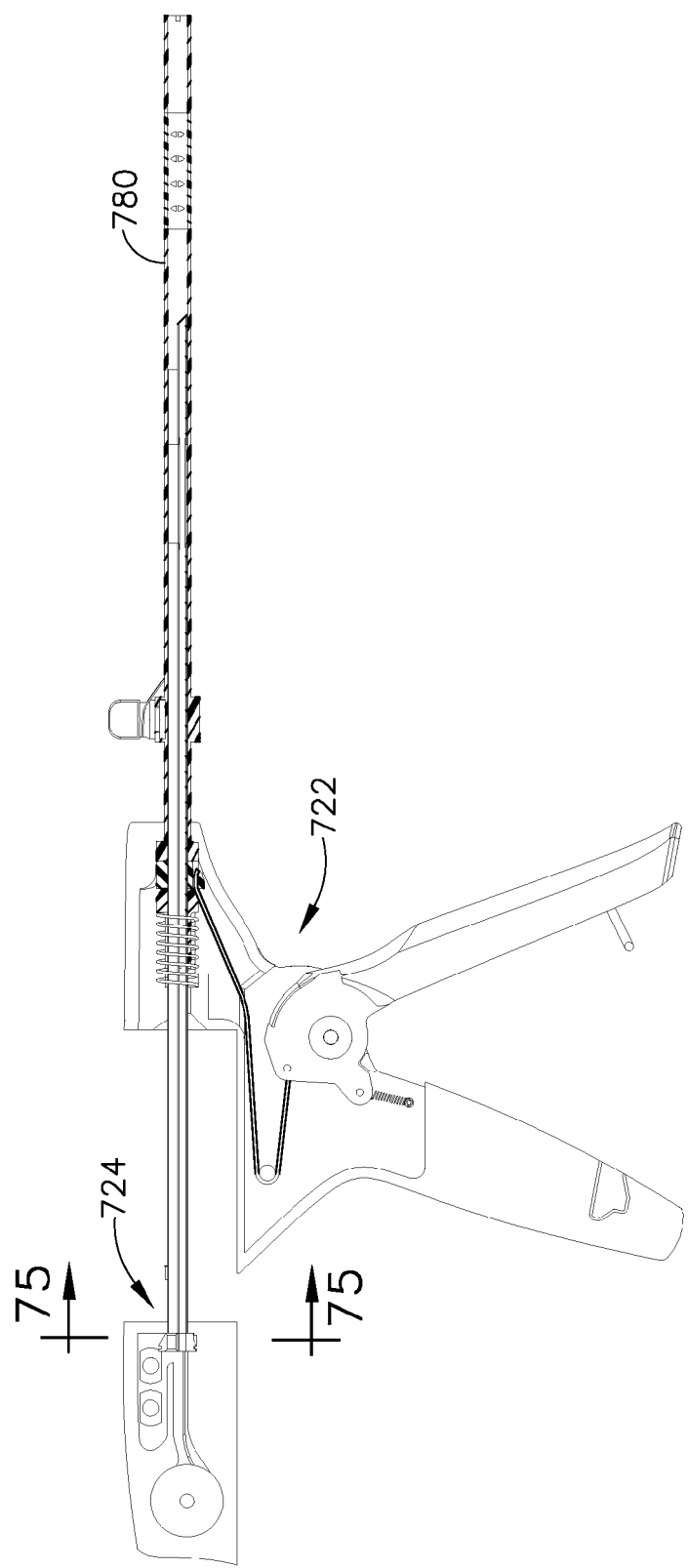
FIG. 70 is a side, sectional view of the fastener deploying device of FIG. 69, showing a cartridge being loaded onto a handle.

FIGS. 69 and 70 show a fifth embodiment for the fastener deploying device of the present invention. In this embodiment, the device again includes a handle 722 and a replaceable cartridge 724 attached to the proximal end of the handle. Coupling members are provided on the device for rapidly and securely removing and attaching cartridges to the handle. The coupling members can comprise any of a number of different types of apparatus, including the deflectable catch and rib/groove arrangements described in the previous embodiments.

Figure 71:
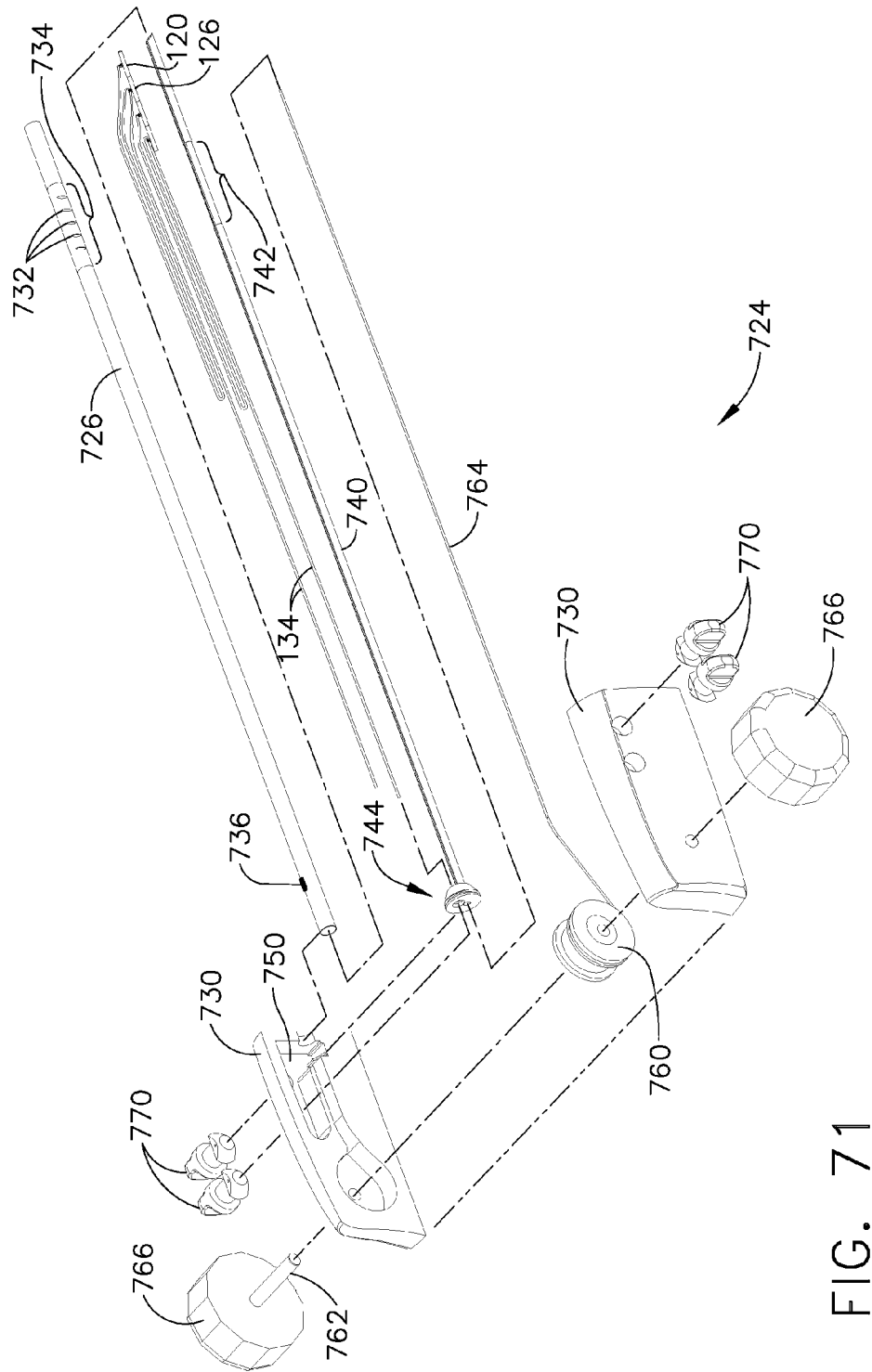
FIG. 71 is an exploded view of the cartridge shown in FIG. 69.
Figure 72:
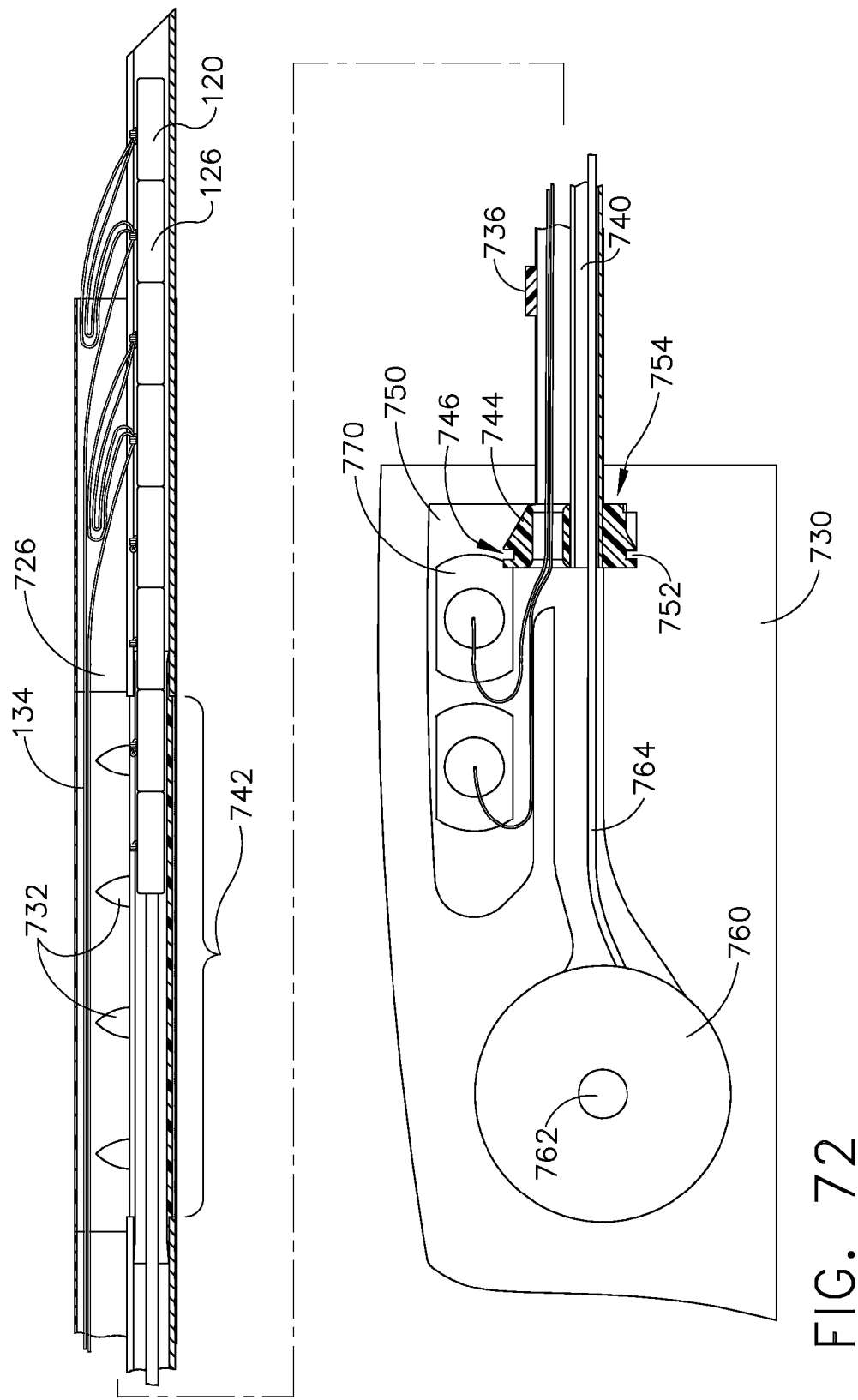
FIG. 72 is a side, sectional view of a cartridge for the fifth deploying device embodiment.

As shown in more detail in FIGS. 71 and 72, cartridge 724 includes an elongated cylindrical shaft 726 extending distally from an opening in the cartridge housing 730. Shaft 726 includes a plurality of openings 732 through the shaft wall near an open distal end. Shaft openings 732 are included within a flexible region 734 in which the shaft wall is comprised of a less rigid material than the remaining shaft length. A key 736 protrudes from the outer surface of shaft 726 adjacent the proximal shaft end. Housed within shaft 726 are at least one fastener and a tissue penetrating member for inserting the fastener into or through tissue, such as a gastric cavity wall. As described above, the penetrating member can be a needle having a slotted lumen that extends proximally from a sharpened tip through the length of the needle. Also as described in the previous embodiments, the cartridge needle at least partially retains and deploys one or more tissue fasteners, such as, for example, pairs of pre-tied T-Tag anchors. A plurality of the pre-tied anchor pairs are loaded into the needle lumen, such that the first "looped" T-Tag anchor deploys initially, followed by the second "attached" T-Tag anchor, although the order may be reversed. The anchor pairs are stacked one against another within the needle lumen, and each anchor is positioned so that the suture opening is aligned with the needle lumen slot. Features such as described above, may be incorporated into the needle embodiments to prevent the unintentional release of the fastener components.

FIG. 71 shows an exemplary needle 740 extending through shaft 726. Needle 740 is preferably attached to the inner wall of shaft 726 proximal and distal of flexible region 734 to prevent relative movement between the needle and the shaft. Needle 740 may be attached to shaft 726 by welding or adhesives, or the shaft and needle may be extruded together during the manufacturing process and assembled with the flexible region separately. Alternatively, needle 740 may be fixed within a channel (not shown) that is attached to the inner wall of shaft 726. Needle 740 is not attached to flexible region 734 of the shaft, in order to allow relative motion between the needle and the shaft as the distal end of the device is articulated, as will described in more detail below. Needle 740 includes a reduced diameter length of flexible material 742 that is inset into the needle proximal of the sharpened tip. Inset 742 is comprised of a less rigid material than the remaining length of the needle. Needle inset 742 is axially aligned with flexible region 732 of shaft 726 to allow the needle to flex along with the shaft within this region.

Figure 75:
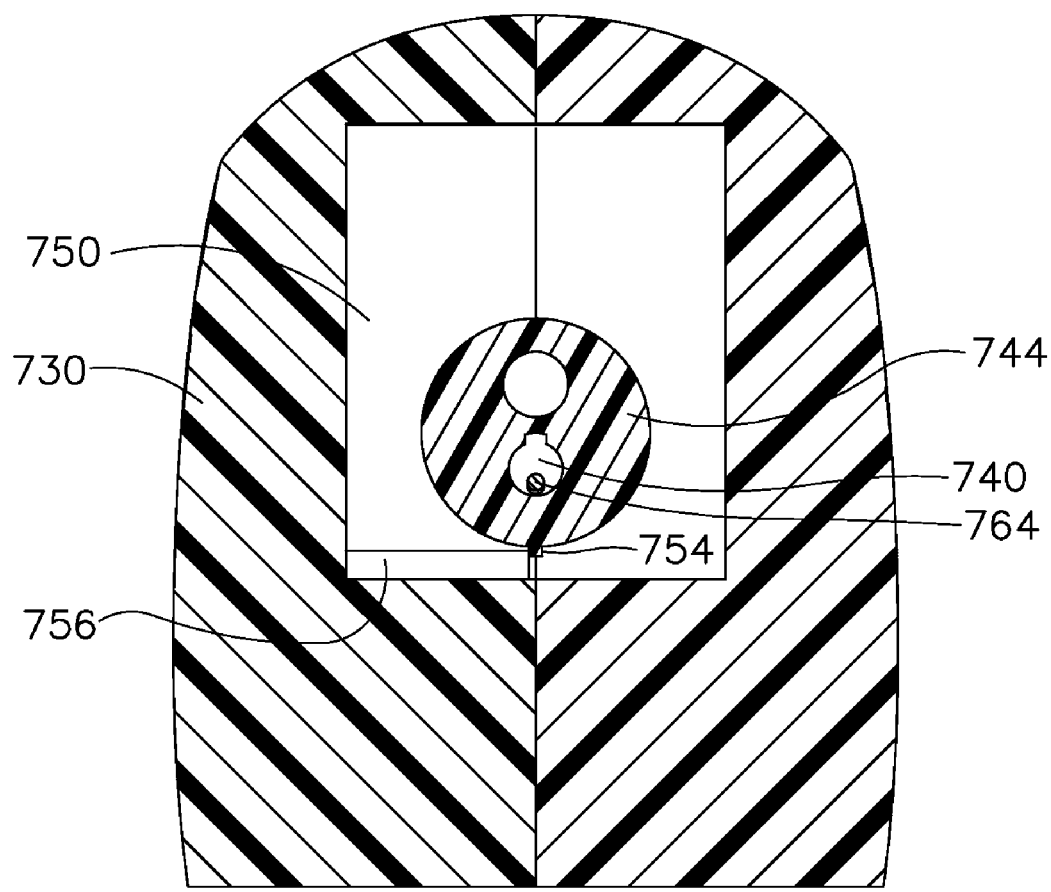
FIG. 75 is a cross-sectional view taken along line 75-75 in FIG. 70.

The proximal end of needle 740 is attached within a rotatable base 744. Base 744 includes a pair of holes, one for needle 740, and the other for suture lengths 134 extending from the retained fasteners in the needle. Base 744 has a circular configuration with a decreasing diameter in the distal direction. A slot 746, shown in FIG. 72, extends around base 744. Base 744 is retained within a cavity 750 in cartridge housing 730. A rim 752 within cavity 750 engages slot 746, as shown in FIGS. 73 and 74. Rim 752 enables base 744 to rotate within cartridge cavity 750, while preventing movement of the base in the direction of the needle axis. Rotation of base 744 in turn rotates the attached needle 740, enabling the sharpened tip of the needle to be repositioned within a circular area without needing to move the entire handle. A fin 754 extends outwardly from the surface of base 744. Fin 754 is axially aligned with a bar 756 in cavity 750. Bar 756 projects out from the wall of cavity 750, as shown in FIG. 75, and into the rotation path of fin 754. Contact between bar 756 and fin 754 during rotation of base 744 blocks the base from making a full 360° revolution within cavity 750.

Proximal of base 744 is a spool 760 which rotates about a fixed shaft 762. As shown in FIGS. 71-74, a length of wire 764 is wound onto spool 760. Wire 764 is preferably comprised of a shape memory alloy that can be deformed for winding onto spool 760, yet returns to a linear shape as the material is unwound from the spool. An example of a suitable shape memory alloy for this application is a nickel-titanium (NiTi) alloy commonly known by the trade name Nitinol. From spool 760, wire 764 passes into the proximal end of needle 740 through base 744. Wire 764 extends through the needle lumen, with the distal end of the wire in contact with the proximal end of the T-Tag anchor stack. Shaft 762 extends through the center of spool 760 and the sides of cartridge housing 730. Outside of cartridge housing 730, shaft 762 is attached at opposite ends to knobs 766. Knobs 766 can be turned to rotate spool 760 and advance an additional section of wire 764 from the spool distally into needle 740 to deploy a fastener.

One or more pull tabs 770 extend through openings in cartridge housing 730. Each of the pull tabs 770 is attached to the loose end of a suture length 134 extending from a fastener in the needle lumen. Suture lengths 134 pass through shaft 726 and base 744 prior to connecting to pull tabs 770. Plugs are located at the base of each pull tab 770 for retaining the tab within the cartridge housing, and preventing the unintentional release of the pull tab prior to deployment of the attached fastener. As mentioned above, various different types of identifying criteria may be used to distinguish between the pull tabs 770 in order to discern the order in which the tabs are to be removed to cinch the attached fasteners.

Figure 76:
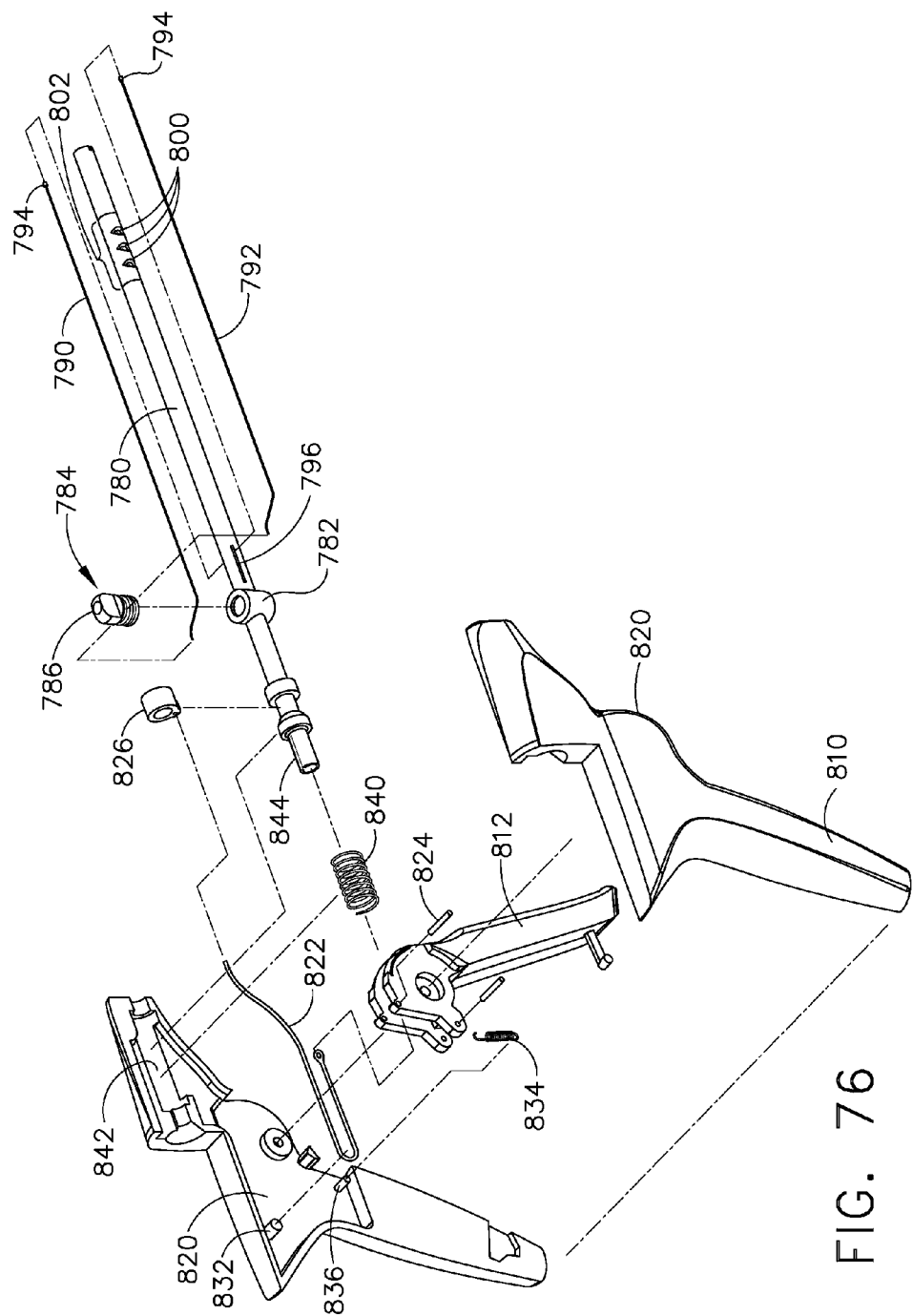
FIG. 76 is an exploded view of the handle shown in FIG. 69.

As shown in FIG. 76, handle 722 includes a distally-extending, protective outer sheath 780. As in the previous embodiments, sheath 780 has sufficient length (on the order of 18") to enable use within an obese patient at numerous trocar access sites. Likewise, sheath 780 is sized to allow for passage through a small (3-5 mm) diameter trocar. The inner diameter of sheath 780 is sized to allow the shaft 726 of a cartridge to pass through the sheath when a cartridge is loaded onto the handle. A collar 782, having a grooved bore formed therein, is attached along the axial length of sheath 780. A flexing controller 784 is mounted within the bore of collar 782. The mounted end of controller 784 is grooved to engage the groove in the collar bore, to allow the controller to turn relative to the collar without dislodging from the collar. A ratchet (not shown) can be included within the collar bore to control movement of the controller within the collar. The exposed end of controller 784 is shaped into a grip 786 for turning the controller.

Figure 78:
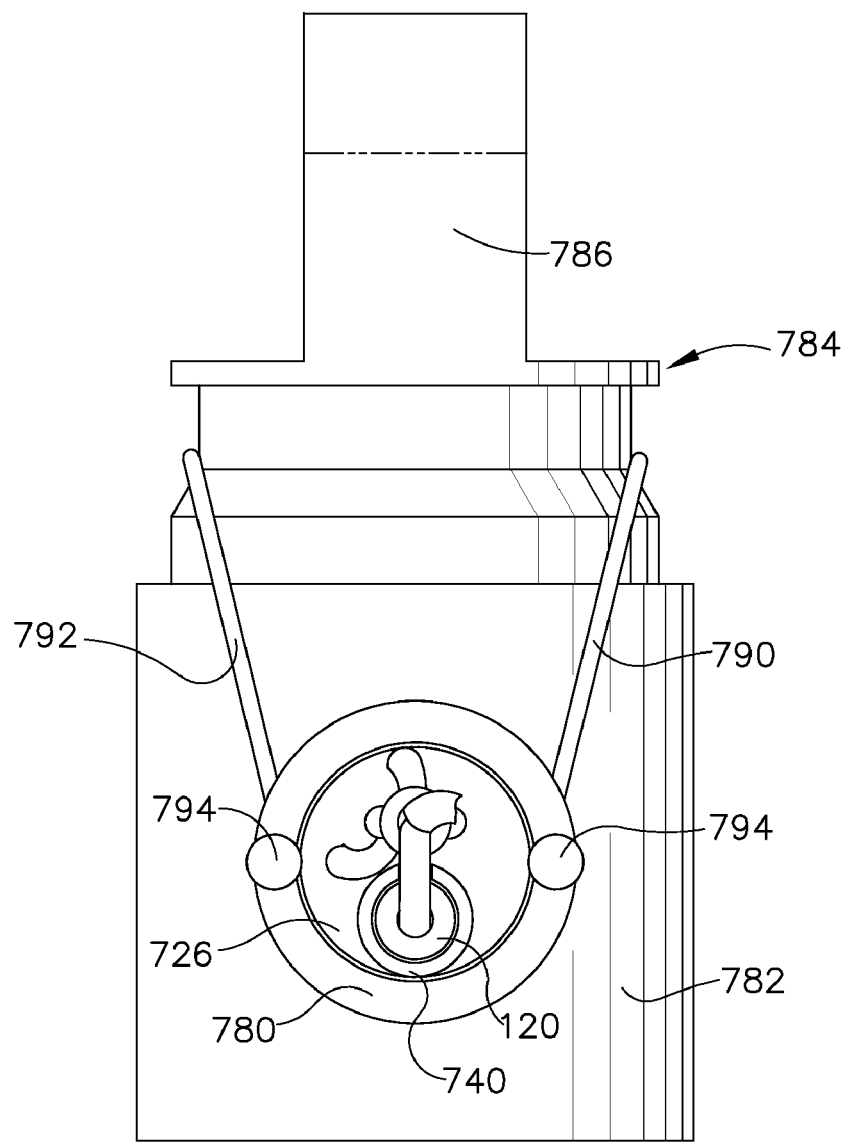
FIG. 78 is an end view looking proximally from the distal end of the device.

Flexing members 790, 792 extend through sheath 780, from controller 784 to the distal tip of the sheath. As shown in FIGS. 77 and 78, the proximal ends of flexing members 790, 792 are attached to controller 784 and extend distally from diametrically opposite sides of the controller. The distal ends of flexing members 790, 792 are attached at diametrically opposite positions to the distal sheath end. Alternatively, a single flexing member can be used, in which case a midsection of the member is wrapped around the circumference of controller 784, with opposite ends of the flexing member then running distally to the end of the sheath. A knot or other size-enhancing element 794 is placed in the distal ends of the flexing members to secure the members within notches at the sheath end. Flexing members 790, 792 pass inside of sheath 780 through slots 796 in the sheath wall. Inside sheath 780, flexing members 790, 792 run in parallel between the inner wall of the sheath and the outer wall of shaft 726. Although shown with a round cross-sectional area, it is envisioned that flexing members 790, 792 may be of numerous configurations (e.g., rectangular, etc.) that allow ease of bending in at least one direction.

Rows of slits or openings 800 are made through the wall of sheath 780. Sheath openings 800 are included within a flexible region 802 in which the sheath wall is comprised of a less rigid material than the remaining sheath length. Each of the rows of openings 800 is radially aligned with one of the flexing members 790, 792, so that the members run next to the openings. The sheath openings 800 are also axially and radially aligned with the openings 732 in shaft 726, and the flexible inset 742 of needle 740. The combination of openings 800, 732, as well as the flexible regions in sheath 780, shaft 726 and needle 740, creates an articulation zone near the distal end of the deploying device. This articulation zone bends in response to the pulling force of the flexing members at the distal tip of the device, to enable the distal end of the device to be turned and maneuvered separately from the rest of the device.

To articulate the device tip, controller 784 is twisted relative to fixed sheath collar 782. Controller 784 may be turned in either a clockwise or a counterclockwise direction depending upon the location of the targeted tissue relative to the distal sheath tip. As controller 784 turns, one of the flexing members 790, 792 is drawn back proximally within sheath 780. As the member is drawn proximally, the member applies a pulling force to the distal end of sheath 780, due to the connection of the member to the sheath tip. Openings 800 in the wall of sheath 780, as well as the less rigid composition of the surrounding portion of the sheath wall, enable the sheath to bend in response to the pulling force at the distal tip. As sheath 780 bends, the sheath contacts the enclosed shaft 726 to also bend the shaft and needle 740 at their flexible regions, due to the small differential between the diameters of the shaft and sheath. Accordingly, the entire tip of the deploying device arcs away from the straight line of the needle axis. The range of articulation for the deploying device tip is up to 45° in either direction from the needle axis. To straighten the device tip back into alignment with the needle axis, the ratchet is released within collar 782 to allow controller 784 to be twisted back to a neutral position. As the controller turns, flexing members 790, 792 move in opposing direction to apply a pulling force to the opposite side of the sheath tip to pull the sheath back into a straight line with the needle axis.

FIG. 77 shows the distal end of the deploying device with controller 784 in a neutral position, so that the distal ends of sheath 780 and needle 740 are aligned with the needle axis. FIG. 79 shows the distal end of the device with controller 784 twisted in a counterclockwise direction to bend the distal end of sheath 780 and the tip of needle 740 in the direction of the controller. As shown in these figures, turning controller 784 counterclockwise pulls flexing member 790 proximally, while advancing the other flexing member 792 distally, due to the connections between the flexing members, controller, and sheath tip. The openings 800, 732 in the sheath and needle shaft, as well as flexible insets in the needle, shaft and sheath, enable the sheath, shaft and needle to flex in response to the pulling of flexing members 790, 792. To flex needle 740 in the opposite direction from that shown in FIG. 79, controller 784 can be turned in a clockwise direction, to pull flexing member 792 proximally, and allow flexing member 790 to be pulled distally by sheath 780. This results in flexing member 792 creating a proximal pulling force on the sheath tip that bends the sheath and needle tip away from the longitudinal needle axis. The flexing apparatus shown and described herein are only representative of the flexing features which may be incorporated within the fastener deploying devices of the present invention. Articulating endoscopic surgical staplers are well known in the art and are commercially available.

Figure 80:
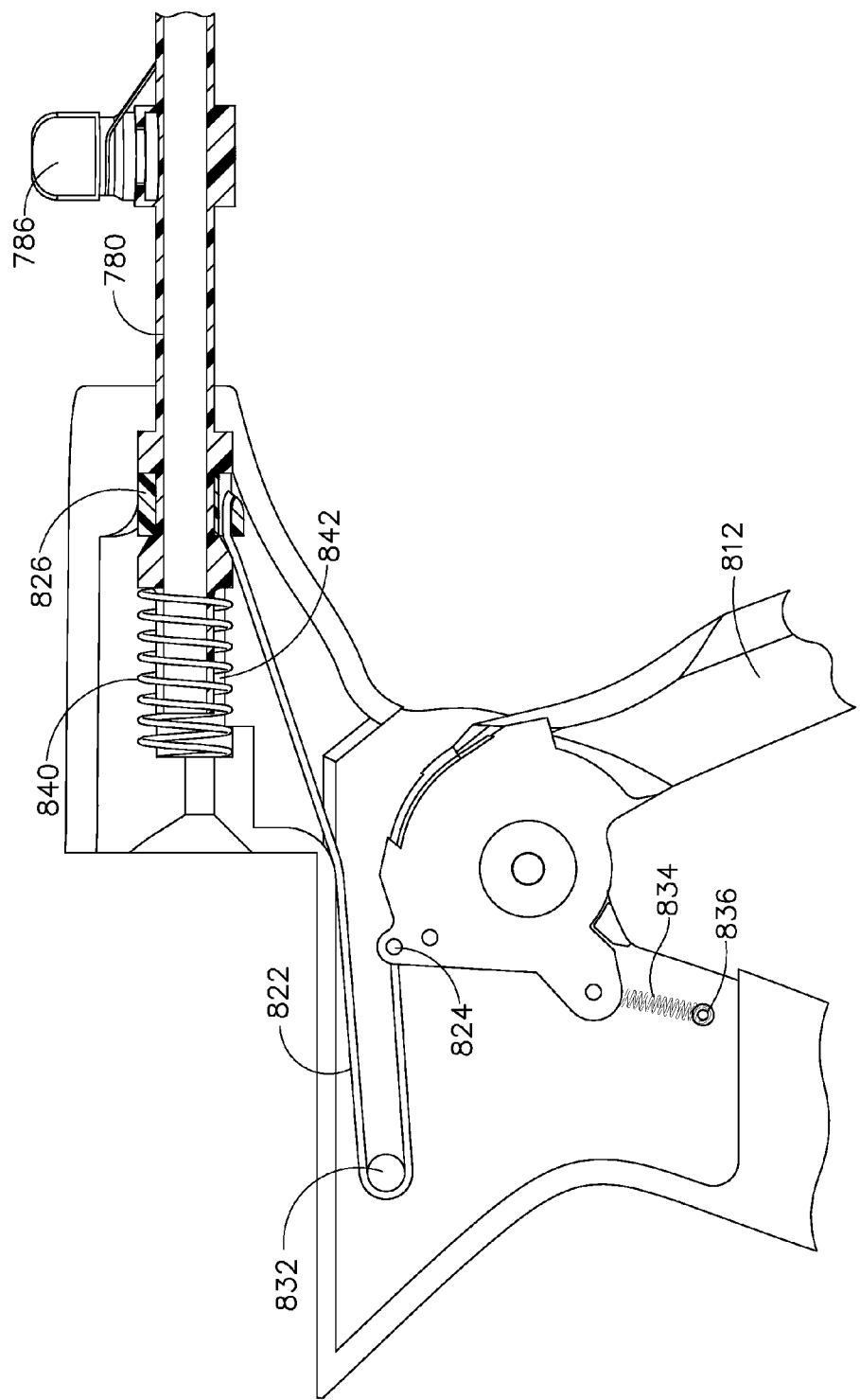
FIG. 80 is a side view of the proximal end of the handle, partially in section, with a portion of the handle housing removed.

Returning now to FIG. 76, handle 722 also includes a pistol grip 810 and an actuating member, such as a manually moveable trigger 812. Trigger 812 pivots about a pin (not shown) extending between sides of handle housing 820. A length of string (or other tension bearing member) is attached to trigger 812 by a toggle 824 which passes through the trigger above the pivot point. As shown in greater detail in FIG. 80, the distal end of string 822 is attached to a ring 826 that extends about sheath 780. Ring 826 is fixed axially along sheath 780 by wider width sections of sheath 780, both distal and proximal of the ring, so that the ring moves axially in conjunction with the sheath. Between trigger 812 and ring 826, string 822 wraps around the proximal side of a pin 832 to form a pulley for advancing and retracting the ring and, thus, sheath 780, with the trigger. A return spring 834 is connected at one end to the trigger 812. The opposite end of the return spring 834 is connected to the handle housing 820 by an additional pin 836. Return spring 834 biases trigger 812 into an open, unsqueezed position in which sheath 780 is in an advanced position covering the needle tip.

A second spring 840 encircles the proximal end of sheath 780 within a channel 842 in handle housing 820. Sheath spring 840 extends between the handle housing 820 at the proximal end, and the widened width of sheath 780 at the distal end, to bias the sheath into a distal, advanced position.

Figure 81:
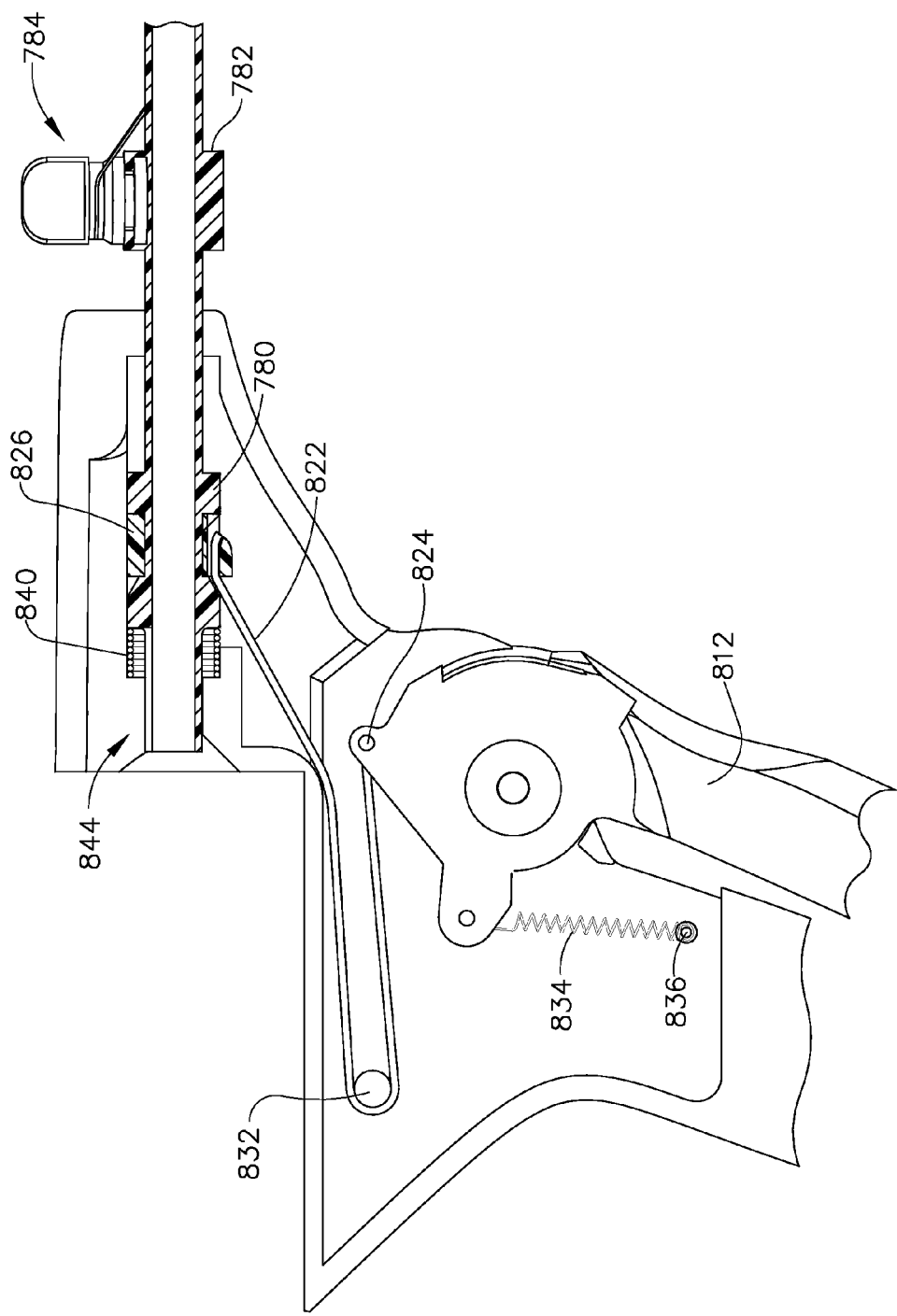
FIG. 81 is a side view of the handle, similar to FIG. 80, showing the trigger pivoted closed to retract the sheath proximally.

When trigger 812 is squeezed, the trigger pivots so as to rotate toggle 824 in a distal direction. As toggle 824 rotates, the toggle pulls the attached end of string 822 distally within handle 722. As the one end of string 822 moves distally, the other end of the string is pulled back proximally, due to the wrapping of the string about pulley pin 832. The proximal movement of the second end of string 822 draws ring 826, as well as sheath 780, proximally due to the pulling force of the ring on the wider width section of the sheath. As shown in FIG. 81, retracting sheath 780 proximally compresses spring 840 against the proximal wall of handle channel 842. A latching mechanism, similar to that described in the previous embodiment, is provided at the base of trigger 812 and pistol grip 810 for locking the trigger in a pivoted position, in order to maintain sheath 780 retracted back from the needle tip.

An axially-extending slot 844 is formed in the proximal end of sheath 780 beneath spring 840. Slot 844 is circumferentially aligned within housing channel 842 so that key 736 on cartridge shaft 726 engages the slot when a cartridge is loaded onto the handle. The linking of key 736 with slot 844 locks cartridge shaft 726 to sheath 780 in a direction normal to the longitudinal axis of the device, to cause the shaft (and needle 740 retained therein) to rotate about the axis when the sheath is rotated.

To load a cartridge 724 onto handle 722, the distal end of shaft 726 is inserted through handle channel 842 and into the proximal end of sheath 780, as shown in FIG. 70. The opening into handle channel 842 may be angled, or funneled, to facilitate the insertion of shaft 726. Cartridge 724 is advanced distally through handle 722 until the cartridge housing locks onto the handle housing. As cartridge 724 is locking onto handle 722, key 736 is fully advanced within sheath slot 844. When fully loaded, the tip of needle 740 is just inside of the open distal end of sheath 780. With the cartridge secured to the handle, the distal end of the device may be articulated to reach different points in the surrounding tissue. To articulate the device tip, controller 784 is turned to bend sheath 780 under the pulling force of flexing members 790, 792, in the manner described above. Controller 784 may be repeatedly turned back and forth until the desired degree of flexing of the device tip is obtained.

Along with bending, sheath 780 (and the shaft and needle retained therein) may be rotated in order to change the location of the needle tip. To rotate sheath 780, grip 786 on controller 784 may be used to pull the controller in either a clockwise or a counterclockwise direction relative to the longitudinal axis of the device. Due to the connection between controller 784 and sheath 780, turning the controller relative to the sheath axis causes the entire sheath to rotate. As sheath 780 rotates, shaft 726 also rotates, due to the connection between key 736 and slot 844. Likewise, needle 740 rotates with shaft 726, with the proximal end of the needle rotating base 744 about rim 752 in cavity 750. Contact between fin 754 on rotatable base 744 and bar 756 in cavity 750 limits the range of rotation for the sheath and needle, and provides feedback when the angular boundaries for rotation have been reached.

With sheath 780 flexed and rotated to the intended location for the T-Tag anchor, trigger 812 is squeezed to pivot the trigger. As trigger 812 pivots, toggle 824 pulls the attached end of string 822 distally, retracting sheath 780 back proximally within the handle and compressing spring 840, as shown in FIG. 81. As sheath 780 retracts, the tip of needle 740 is exposed outside of the open end of the sheath. As the needle tip is exposed, trigger 812 latches against pistol grip 810 to hold the sheath 780 in a retracted position, back from the needle tip.

With the needle tip exposed, the device is inserted into tissue at the intended fastener location. Inside of the tissue, one or both of knobs 766 is turned to deploy a T-Tag anchor. As knobs 766 are turned, the force is transferred through shaft 762 to rotate spool 760, and unwind a portion of wire 764 from the spool. As wire 764 is unwound from spool 760, the wire is advanced into the needle lumen. The wire assumes a linear shape that is coaxial with the needle lumen as the wire unwinds, due to the shape memory characteristics of the wire. Within needle 740, the advancing section of wire 764 applies force against the proximal end of the T-Tag anchor stack. The force of wire 764 against the T-Tag anchor stack drives the distal-most T-Tag anchor through the open needle tip and out of the device.

After deployment of the distal-most T-Tag anchor, feedback is provided to the surgeon of the deployment, enabling the surgeon to cease rotation of knobs 766. Trigger 812 is unlatched from pistol grip 810, returning the trigger to its initial position under the force of return spring 834. As trigger 812 pivots open, the tension in string 822 is released, allowing the string to slide around pin 832 and release the hold on ring 826. As ring 826 is released, sheath 780 is advanced distally over the tip of needle 740 by the force of sheath spring 840. With the needle tip concealed within sheath 780, the distal end of the sheath may again be maneuvered via flexing controller 784 to move the device tip to the site for the second T-Tag anchor. At the second T-Tag anchor location, trigger 812 is again squeezed and latched to retract sheath 780 and expose the needle tip. After the exposed needle tip is inserted into tissue, knobs 766 are again rotated to advance an additional segment of wire 764 into needle 740. As wire 764 is advanced distally into needle 740, the wire again forces the distal-most T-Tag anchor through the open tip of the needle. After the second T-Tag anchor of the fastener has been deployed, trigger 812 is unlatched, as described previously, to allow spring 840 to drive sheath 780 forward over the needle tip. With the needle tip covered, the pull tab 770 associated with the first deployed fastener can be drawn out of the cartridge, and a force applied to the tab to tension the attached suture length 134, as described in the previous embodiments. As the suture length 134 is tensioned, the deployed T-Tag anchors are drawn together to oppose the surrounding tissue.

After the initial fastener has been deployed and cinched, the suture extending from the fastener can be severed. A V-notch, such as described above, may be provided at the distal end of the sheath for severing the cinched suture. Controller 784 may be used to maneuver the position of the V-notch (either by flexing side-to-side or by rotating the V-notch) to assist in drawing the suture into the V-notch to sever the suture. Alternatively, other known cutting methods or devices may be utilized for severing the suture following cinching of the attached fastener. After the suture is severed, the fastener deploying device can be moved to a different location or, alternatively, the handle can be maintained in the same position, and the end of the device manipulated via flexing controller 784 to reach a different tissue location to continue deploying fasteners. After all of the fasteners in the cartridge have been deployed, the cartridge may be removed from the proximal end of the handle, as in the previous embodiments, and a new cartridge loaded onto the handle in order to continue deploying fasteners.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, steam.

What is claimed:

1. A method for deploying fasteners comprising:
   a. providing a device comprising a handle and at least one actuator, said handle connected to an elongated hollow housing having distal and proximal ends, a first cartridge containing at least one fastener releasably connectable to said handle, an elongated pusher movable through said hollow housing from said distal to said proximal end for deploying said fastener from said distal end;
   b. increasing the stiffness of said pusher at a distal end thereof;
   c. advancing said pusher through said elongated housing to deploy said fasteners.

2. The method of claim 1 wherein the step of increasing the stiffness of said pusher comprises the step of deforming said pusher.

3. The method of claim 2 wherein the step of increasing the stiffness of said pusher comprises the step of deforming said pusher into a V-shape.

4. A method of deploying fasteners within a body comprising the steps of:
   a. providing a device comprising a handle and at least one actuator, said handle connected to an elongated hollow housing having distal and proximal ends, and a needle within said hollow housing, a first cartridge containing at least one fastener releasably connectable to said distal end of said hollow housing, said fastener, at least partially housed within said needle, said fastener comprising at least two anchors connected together by a non-resilient flexible suture which does not resist deformation under compressible loads;
   b. inserting said distal end of said hollow housing to a target site within a body
   c. increasing the stiffness of said pusher at a distal end thereof;
   d. attaching tissue together within the body advancing said pusher through said elongated housing to deploy said fasteners.

5. The method of claim 4 wherein the step of increasing the stiffness of said pusher comprises the step of deforming said pusher.

6. The method of claim 5 wherein the step of increasing the stiffness of said pusher comprises the step of deforming said pusher into a V-shape.

7. The device of claim 5 wherein said needle has a slot extending from a distal end at least partially back towards a proximal end of said needle.

* * * * *